US006489095B2

(12) United States Patent
Herrnstadt et al.

(10) Patent No.: US 6,489,095 B2
(45) Date of Patent: *Dec. 3, 2002

(54) DIAGNOSTIC METHOD BASED ON QUANTIFICATION OF EXTRAMITOCHONDRIAL DNA

(75) Inventors: Corinna Herrnstadt; Soumitra S. Ghosh, both of San Diego; William Clevenger, Vista; Eoin D. Fahy; Robert E. Davis, both of San Diego, all of CA (US)

(73) Assignee: Mitokor, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/098,079

(22) Filed: Jun. 15, 1998

(65) Prior Publication Data

US 2002/0064773 A1 May 30, 2002

(51) Int. Cl.$^7$ .......................... C12Q 1/68; C12P 19/34; C07H 21/02; C07H 21/04
(52) U.S. Cl. ....................... 435/6; 435/91.1; 435/91.2; 435/91.5; 536/23.1; 536/24.3; 536/24.31; 536/24.32; 536/24.33
(58) Field of Search .................... 435/6, 91.1, 91.2, 435/91.5; 536/23.1, 24.3, 24.31, 24.32, 24.33

(56) References Cited

U.S. PATENT DOCUMENTS

| | | | | |
|---|---|---|---|---|
| 4,683,202 A | * | 7/1987 | Mullis | 435/91 |
| 5,508,167 A | * | 4/1996 | Roses et al. | 435/6 |
| 5,840,493 A | | 11/1998 | Davis et al. | 435/6 |
| 6,140,067 A | | 10/2000 | Anderson et al. | 435/26 |
| 6,232,078 B1 | | 5/2001 | Lee et al. | 435/6 |

FOREIGN PATENT DOCUMENTS

| | | |
|---|---|---|
| EP | 0 594 959 A1 | 5/1994 |
| WO | WO 93/21339 | 10/1993 |
| WO | WO 95/26973 | 10/1995 |
| WO | WO 98/27227 | 6/1998 |

OTHER PUBLICATIONS

Hadler et al, "Mitochondrial DNA and nuclear DNA from normal rat liver have a common sequence", Proc. Natl. Acad. Sci. (1983) 80:6495–6499.*

Shay et al, "Mitochondrial DNA copy number is proportional to total cell DNA under a variety of growth conditions", J. Biol. Chem. (Sep. 5, 1990) 265(25):14802–14807.*

Poulton et al, "Variation in mitochondrial DNA levels in muscle from normal controls. Is depletion of mtDNA in patients with mitochondrial myopathy a distinct clinical syndrome?", J. Inher. Metab. Dis. (1995) 18:4–20.*

Davis II et al., "Evidence That Two Reports of mtDNA Cytochrome c Oxidase 'Mutations' in Alzheimer's Disease Are Based on nDNA Pseudogenes of Recent Evolutionary Origin," *Biochemical and Biophysical Research Communications* 244:877–883, 1998.

du Manoir et al., "Quantitative Analysis of Comparative Genomic Hybridization," *Cytometry* 19:27–41, 1995.

Ghosh et al., "Longitudinal Study of a Heteroplasmic 3460 Leber Hereditary Optic Neuropathy Family by Multiplexed Primer–Extension Analysis and Nucleotide Sequencing," *Am. J. Hum. Genet.* 58:325–334, 1996.

Hadler et al., "Genomic Mitochondrial DNA–Like Sequences in Normal and Tumor Tissue of Mouse and Rat," *The FASEB Journal* 4(3):A764, 1990.

Parfait et al., "Coamplification of Nuclear Pseudogenes and Assessment of Heteroplasmy of Mitochondrial DNA Mutations," *Biochemical and Biophysical Research Communications* 247:57–59, 1998.

Suzuki et al., "Diabetes with Mitochondrial Gene tRNA$^{LYS}$ Mutation," *Diabetes Care*, US, American Diabetes Association, Alexandria, VA, 17(2):1428–1432, 1994.

Wallace, "Mitochondrial Genetics: A Paradigm for Aging and Degenerative Diseases?," *Science* 256:628–632, May 1, 1992.

Antonetti et al., "Increased Expression Of Mitochondrial–Encoded Genes In Skeletal Muscle Of Humans With Diabetes Mellitus," *J. Clin. Invest.* 95: 1383–1388, 1995.

Boultwood et al., "Amplification Of Mitochondrial DNA In Acute Myeloid Leukaemia," *British Journal Of Haematology* 95: 426–431, 1996.

Gerbitz et al., "Mitochondria and Diabetes. Genetic, Biochemical, And Clinical Implications Of The Cellular Energy Circuit," *Diabetes* 45: 113–126, 1996.

Lightowlers et al., "Mammalian Mitochondrial Genetics: Heredity, Heteroplasmy And Disease," *TIG* 13(11): 450–455, 1997.

Moraes et al., "mtDNA Depletion With Variable Tissue Expression: A Novel Genetic Abnormality In Mitochondrial Diseases," *Am. J. Hum. Genet.* 48: 492–501, 1991.

Swerdlow et al., "Origin And Functional Consequences Of The Complex I Defect In Parkinson's Disease," *Ann. Neurol.* 40:663–671, 1996.

Williams, "Mitochondrial Gene Expression In Mammalian Striated Muscle," *The Journal Of Biological Chemistry* 261(26): 12390–12394, 1986.

(List continued on next page.)

Primary Examiner—Jeffrey Fredman
(74) *Attorney, Agent, or Firm*—Seed Intellectual Property Law Group PLLC

(57) ABSTRACT

Compositions and methods based on quantification of extra-mitochondrial DNA (exmtDNA) sequences are provided that are useful for detecting the presence of or risk for having a disease associated with altered mitochondrial function, and for identifying agents suitable for treating such diseases. The exmtDNA sequences have strong homology to authentic mitochondrial DNA (mtDNA) sequences.

20 Claims, 35 Drawing Sheets

OTHER PUBLICATIONS

Williams et al., "Regulation Of Nuclear And Mitochondrial Gene Expression by Contractile Activity In Skeletal Muscle," *The Journal Of Biological Chemistry 261*(1): 376–380, 1986.

Anderson et al., "Sequence and organization of the human mitochondrial genome," *Nature 290*: 457–465, 1981.

Cannizzaro and Shi, *Methods in Molecular Biology*, vol. 75: Basic Cell Culture Protocols, Humana Press Inc., Totowa, New Jersey, 1997, Chapter 26, "Fluorescent in Situ Hybridization (FISH) for DNA Probes in the Interphase and Metaphase Stages of the Cell Cycle," pp. 313–322.

Corder et al., "Gene Dose of Apolipoprotein E Type 4 Allele and the Risk of Alzheimer's Disease in late Onset Families," *Science 261*: 921–923, 1993.

Davis et al., "Mutations in mitochondrial cytochrome c oxidase genes segregate with late–onset Alzheimer disease," *Proc. Natl. Acad. Sci. USA 94*: 4526–4531, 1997.

DeKosky and Scheff, "Synapse Loss in Frontal Cortex Biopsies in Alzheimer's Disease: Correlation with Cognitive Severity," *Annals of Neurology 27*(5): 457–464, 1990.

Fahy et al., "Multiplex fluorescence–based primer extension method for quantitive mutation analysis of mitochondrial DNA and its diagnostic application for Alzheimer's disease," *Nucleic Acids Research 25*(15): 3102–3109, 1997.

Fossel, "Telomerase and the Aging Cell," *JAMA The Journal of the American Medical Association 279*(21): 1673–1760, 1998.

Gómez–Diaz et al., "Ascorbate Stabilization Is Stimulated in $\rho°$HL–60 Cells by $CoQ_{10}$ Increase at the Plasma Membrane," *Biochemical And Biophysical Research Communications 234*: 79–81, 1997.

Hirano et al., "Apparent mtDNA heteroplasmy in Alzheimer's disease patients and in normals due to PCR amplification of nucleus–embedded mtDNA pseudogenes," *Proc. Natl. Acad. Sci. USA 94*: 14894–14899, 1997.

Iwama et al., "Telomeric length and telomerase activity vary with age in peripheral blood cells obtained from normal individuals," *Human Genetics 102*(4): 397–402, 1998.

LaBranche et al., "Telomere elongation by hnRNP A1 and a derivative that interacts with telomeric repeats and telomerase," *Nature Genetics 19*(2): 199–202, 1998.

Larm et al., "Up–regulation of the Plasma Membrane Oxidoreductase as a Prerequisite for the Viability of Human Namalwa $\rho°$ Cells," *The Journal Of Biological Chemistry 269*(48): 30097–30100, 1994.

Lopez et al., "Numt, a Recent Transfer and Tandem Amplification of Mitochondrial DNA to the Nuclear Genome of the Domestic Cat," *Journal Of Molecular Evolution 39*: 174–190, 1994.

Marchetti et al., "Apoptosis–associated Derangement of Mitochondrial Function in Cells Lacking Mitochondrial DNA," *Cancer Research 56*(9): 2033–2038, 1996.

National Institute on Aging/Alzheimer's Association Working Group, "Apoliprotein E genotyping in Alzheimer's disease," *The Lancet 347*: 1091–1095, 1996.

Nowak et al., "Regulation of Telomerase Activity in Normal and Malignant Human Cells," *The Cancer Journal from Scientific American 4*(3): 148–154, 1998.

Parnetti et al., "Increased cerebrospinal fluid pyruvate levels in Alzheimer's disease," *Neuroscience Letters 199*: 231–233, 1995.

Parker, Jr. et al., "Abnormalities of the Electron Transport Chain in Idiopathic Parkinson's Disease," *Ann. Neurol. 26*: 719–723, 1989.

Shay, "Telomerase in Cancer: Diagnostic, Prognostic, and Therapeutic Implications," *The Cancer Journal from Scientific American 4*(Supplement 1): S26–S34, 1998.

Wallace et al., "Ancient mtDNA sequences in the human nuclear genome: A potential source of errors in identifying pathogenic mutations," *Proc. Natl. Acad. Sci. USA 94*: 14900–14905, 1997.

* cited by examiner

Contig 1 (1,6803)
    Contig Length:              6803 bases
    Average Length/Sequence:     620 bases
    Total Sequence Length:     16133 bases
    Top Strand:                   17 sequences
    Bottom Strand:                 9 sequences
    Total:                        26 sequences

```
CCTACGGGCT ACTACAACCC TTCGCTGACG CCATAAAACT CTTCACCAAA   50
GAGCCCCTAA AACCCGCCAC ATCTACCATC ACCCTCTACA TCACCGCCCC  100
GACCTTAGCT CTCACCATCG CTCTTCTACT ATGAACCCCC CTCCCCATAC  150
CCAACCCCCT GGTCAACCTC AACCTAGGCC TCCTATTTAT TCTAGCCACC  200
TCTAGCCTAG CCGTTTACTC AATCCTCTGA TCAGGGTGAG CATCAAACTC  250

AAACTACGCC CTGATCGGCG CACTGCGAGC AGTAGCCCAA ACAATCTCAT  300
ATGAAGTCAC CCTAGCCATC ATTCTACTAT CAACATTACT AATAAGTGGC  350
TCCTTTAACC TCTCCACCCT TATCACAACA CAAGAACACC TCTGATTACT  400
CCTGCCATCA TGACCCTTGG CCATAATATG ATTTATCTCC ACACTAGCAG  450
AGACCAACCG AACCCCCTTC GACCTTGCCG AAGGGGAGTC CGAACTAGTC  500

TCAGGCTTCA ACATCGAATA CGCCGCAGGC CCCTTCGCCC TATTCTTCAT  550
AGCCGAATAC ACAAACATTA TTATAATAAA CACCCTCACC ACTACAATCT  600
TCCTAGGAAC AACATATRAC GCACTCTCCC CTGAACTCTA CACAACATAT  650
TTTGTCACCA AGACCCTACT TCTRACCTCC CTGTTCTTAT GAATTCGAAC  700
AGCATACCCC CGATTCCGCT ACGACCAACT CATACACCTC CTATGAAAAA  750

ACTTCCTACC ACTCACCCTA GCATTACTTA TATGATATGT CTCCATACCC  800
ATTACAATCT CCAGCATTCC CCCTCAAACC TAAGAAATAT GTCTGATAAA  850
AGAGTTACTT TGATAGAGTA AATAATAGGA RYTTAAAYCC CCTTATTTCT  900
AGGACTATGA GAATCGAACC CATCCCTGAG AATCCAAAAT TCTCCGTGCC  950
ACCTATCACA CCCCATCCTA AAGTAAGGTC AGCTAAATAA GCTATCGGGC 1000
```

*Fig. 1A*

```
CCATACCCCG AAAATGTTGG TTATACCCTT CCCGTACTAA TTAATCCCCT  1050
GGCCCAACCC GTCATCTACT CTACCATCTT TGCAGGCACA CTCATCACAG  1100
CGCTAAGCTC GCACTGATTT TTTACCTGAG TAGGCCTAGA AATAAACATG  1150
CTAGCTTTTA TTCCAGTTCT AACCAAAAAA ATAAACCCTC GTTCCACAGA  1200
AGCTGCCATC AAGTATTTCC TCACGCAAGC AACCGCATCC ATAATCCTTC  1250

TAATAGCTAT CCTCTTCAAC AATATACTCT CCGGACAATG WRMCATWACC  1300
AATACYAYCA ATCAATACTC ATCATTAATA ATCATAATRG CTATAGCAAT  1350
AAAACTAGGA ATAGCCCCCT TCACTTCTG AGTCCCAGAG GTTACCCAAG    1400
GGCACCCCTC TGACATCCGG CCTGCTYCTT CTCACATGAC AAAAACTAGC  1450
CCCCATCTCA ATCATATACC AAATYTCTCC CTCAYTAAAC GTAAGCCTTC  1500

TCCTCACTCT YTCAATCTTA TCCATCATRG CAGGCAGTTG AGGTGGATTA  1550
AACCARACCC ARCTACGCAA AATCTTAGCA TACTCCTCAA TTACCCACAT  1600
AGGATGAATA AYAGCAGTTC TACCGTACAA CCCTAACATA ACCATTCTTA  1650
ATTTAACTAT TTATATTATC CTAACTACTA CCGCATTCCT ACTACTCAAC  1700
TTAAACTCCA GCACCACAAC CCTACTACTA TCTCGCACCT GAAACAAGCT  1750

AACATGACTA ACACCCTTAA TTCCATCCAC CCTCCTCTCC CTAGGAGGCC  1800
TGCCCCCGCT AACCGGCTTT TTGCCCAAAT GGGCCATTAT CGAAGAATTC  1850
ACAAAAAACA ATAGCCTCAT CATCCCCACC ATCATAGCCA YCATCACCCT  1900
CCTTAACCTC TACTTCTACC TRCGCCTAAT CTACTCCACC TCAATCACAC  1950
TACTCCCYAT ATCTAACAAC GTAAAAATAA AATGACAGTT TGAACAYACA  2000

AAACCCACCC CATTCCTCCC CACACTCATC GCCCTTACCA CRCTRCTCCT  2050
ACCTATCTCC CCTTTTATRC TAATAATCTT ATAGAAATTT AGGTTAAATA  2100
CAGACCAAGA GCCTTCAAAG CCCTCAGTAA GTTGCAATAC TTAATTTCTG  2150
YAACAGCTAA GGACTGCAAA ACCCCACTCT GCATCAACTG NAACGCAAAT  2200
CAGCCACTTT AATTAAGCTT AAGCCCTTAC TAGACCAATG GGAACTTAAA  2250
```

*Fig. 1B*

```
CCCACAAACA CTTAGTTAAC AGCTAAGCAC CCTAATCAAC TGGCTTCAAT    2300
CTACTTCTCC CGCCGCCGGG AAAAAAGGCG GGAGAAGCCC CGGCAGGTTT    2350
GAAGCTGCTT CTTCGAATTT GCAATTCAAT ATGAAAATCA CCTCRGAGCT    2400
GGTAAAAAGA GGCYTAACCC CTGTCTTTAG ATTTACAGTC CAATGCTTCA    2450
CTCAGCCATT TTACCTCACC CCCACKGATG TTCGCCGACC GTTGACTATT    2500

CTCTACAAAC CACAAAGACA TTGGAACACT ATACCTATTA TTCGGCGCAT    2550
GAGCTGGAGT CCTAGGCACA GCTCTAAGCC TCCTTATTCG AGCCGARCTG    2600
GGCCAGCCAG GCAACCTTCT AGGTAACGAC CACATCTACA ACGTTATCGT    2650
CACAGCCCAT GCATTTGTAA TAATCTTCTT CATAGTAATA CCCATCATAA    2700
TCGGAGGCTT TGGCAACTGA CTAGTTCCCC TAATAATCGG TGCCCCCGAT    2750

ATGGCGTTTC CCCGCATAAA CAACATAAGC TTMTGACTCT TACCYCCCTC    2800
TCTCMTACTC CTGYTYGCAT CTGCTATAGT GGAGGCCGGM GCAGGAACAG    2850
GTTGAACAGT MTACCCTCCC TTRGCAGGGA ACTACTCCCA CCMTGGAGCC    2900
TCCGTAGACS TAACCATCTT STCCTTACAC YTAGCAGGTR TCTCCTTCTA    2950
TCTTAGGGGC CATCAATTTC ATCACAACAA TTATYAATAT AAAACCCCCT    3000

GCCATAACCC AATACCAAAC GCCCCTYTTC GTCTGATCCG TCCTAATCAC    3050
AGCAGTCYTA CTTCTCCTAT CTCTCCCAGT CCTAGCYGCT GGCATCACTA    3100
TACTACTAAC AGACCGYAMC YTCAACACCA CCTTYTTYGA CCCMGCCGGA    3150
GGAGGAGACC CCATTCTATA CCAACACCTA TTCTGATTTT TCGGTCACCC    3200
TGAAGTTTAT ATTCTYATCC TACCAGGCTT CGGAATAATC TCCCATATTG    3250

TAACTTACTA CTCCGGAAAA AAAGAACCAT TTGGATACAT AGGTATGGTC    3300
TGAGCTATGA TATCAATTGG CTTCCTAGGG TTTATCGTGT GAGCACACCA    3350
TATATTTACA GTAGGAATAG ACGTAGACAC ACGAGCATAT TTCACCTCCG    3400
CTACCATAAT CATCGCTATC CCCACCGGCG TCAAAGTATT TAGCTGACTC    3450
GCCACACTCC ACGGAAGCAA TATGAAATGA TCTGCTGCAG TGCTCTGAGC    3500
```

*Fig. 1C*

```
CCTAGGATTT ATTTTTCTTT TCACCGTAGG TGGCCTGACT GGCATTGTAT  3550
TAGCAAACTC ATCACTAGAC ATCGTACTAC ACGACACGTA CTACGTTGTA  3600
GCCCACTTCC ACTATGTCCT ATCAATAGGA GCTGTATTTG CCATCATAGG  3650
AGGCTTCATT CACTGATTTC CCCTATTCTC AGGGTACACC CTAGACCAAA  3700
CCTACGCCAA AATCCATTTC GCTATCATAT TCATCGGCGT AAATCTAACT  3750

TTCTTCCCAC AACACTTTCT CGGCCTATCC GGAATGCCCC GACGTTACTC  3800
GGACTAYCCC GATGCATACA CCACATGAAA YATCCTATCA TCTGTAGGCT  3850
CATTCATTTC TCTAACAGCA GTAATATTAA TAATTTTCAT AATTTGAGAA  3900
GCCTTCGCTT CGAAGCGAAA AGTCCTAATA GTAGAAGAAC CTCCATAAA  3950
CCTGGAGTGA CTATATGGAT GCCCCCCACC CTACCACACA TTCGAAGAAC  4000

CCGTATACAT AAAATCTAGA CAAAAAGGA AGGAATCGAA CCCCCCCAAA  4050
GCTGGTTTCA AGCCAACCCC ATGGCCTCCA TGACTTTTTC AAAAAGATAT  4100
TAGAAAAACC ATTTCATAAC TTTGTCAAAG TTAAATTATA GGCTAAATCC  4150
TATATATCTT AATGGCACAT GCAGCGCAAG TAGGTCTACA AGACGCTACT  4200
TCCCCTATCA TAGAAGAGCT TATCATCTTT CATGATCACG CCCTCATAAT  4250

CATTTTCCTT ATCTGCTTCC TAGTCCTGTA CGCCCTTTTC CTAACACTCA  4300
CAACAAAACT AACTAATACT AACATCTCAG ACGCTCAGGA AATAGAAACC  4350
GTCTGAACTA TCCTGCCCGC CATCATCCTA GTCCTYATCG CCCTCCCATY  4400
CCTACGCATC CTTTACATAA CAGACGAGGT CAACGATCCC TCCYTTACCA  4450
TCAAATCAAT TGGCCAYCAA TGGTACTGAA CCTACGARTA CACCGACTAC  4500

GGCGGACTAA TCTTCAACTC CTACATACTT CCCCCATTAT TCCTAGAACC  4550
AGGCGACCTG CGACTCCTTG ACGTTGACAA TCGAGTAGTA CTCCCGRTTG  4600
AAGCCCCCAT TCGTATAATA ATTACATCAC AAGACGTCTT ACACTCATGA  4650
GCTGTCCCCA CATTAGGCTT AAAAACAGAT GCAATTCCCG GACGTCTAAA  4700
CCAAACCACT TTCACTGCTA CACGACCAGG GGTATACTAC GGCCAATGCT  4750
```

*Fig. 1D*

```
CTGAAATCTG TGGAGCAAAC CAGTTTTATG CCCATCGTCC TAGAATTAAT   4800
TCCCCTAAAA ATCTTTGAAA TAGGGCCCGT ATTTACCCTA TAGCACCCCC   4850
TCTACCCCCT CTAGAGCCCA CTGTAAAGCT AACTTAGCAT TAACCTTTTA   4900
AGTTAAAGAT TAAGAGAACC AACACCTCTT TACAGTGAAA TGCCCCAACT   4950
AAATACTACC GTATGACCCA CCATAATTAC CCCCATACTC CTTACACTAT   5000

TCCTCATCAC CCAACTAAAA ATATTAAAYA CAAAYTACCA CCTACCTCCC   5050
TCACCAAAGC CCATAAAAAT AAAAAAYTAT AACAAACCCT GAGAACCAAA   5100
ATGAACGAAA ATCTGTTCRC TTCATTCATT GCCCCCACAA TCCTAGGCCT   5150
ACCCGCCGCA GTACTGATCA TTCTATTTCC CCCTCTATTG ATCCCCACCT   5200
CCAAATATCT CATCAACAAC CGACTAATTA CCACCCAACA ATGACTAATC   5250

MAACTAACCT CAAAACAAAT GATARCCATA CACAACACTA ARGGACGAAC   5300
CTGATCTCTT ATACTAGTAT CCTTAATCAT TTTTATTGCC ACAACTAACC   5350
TCCTCGGACT CCTGCCTCAC TCATTTACAC CAACCACCCA ACTATCTATA   5400
AACCTAGCCA TGGCCATCCC CTTATGAGCG GGCRCAGTGA TTATAGGCTT   5450
TCGCTCTAAG ATTAAAAATG CCCTAGCCCA CTTCTTACCA CAAGGCACAC   5500

CTACACCCCT TATCCCYATA CTAGTTATTA TCGAAACCAT CAGSCTAMTC   5550
ATTCAACCAA TAGCCCTGGC CGTAMGSCTA ACCGCTAACA TTACTGCAGG   5600
CCACCTAACT CATGMACCTA ATTGGAAGCG CCACMACTAG CAATATCAAS   5650
YATTAACCTT CCCTTCTACA CTTATCATYT TCACAATTCT AATTCTACTG   5700
ACTATCCTAG AAATCGCTGT CGCCTTAATC CAAGCCTACG TTTTYACACT   5750

TYTAGTAAGC CTCTACCTGC ACGACAACAC ATAATGACCC ACCAATCACA   5800
TGCCTATCAT ATAGTAAAAC CCAGCCCATG RCCCCTAACA GGGGCCCTCT   5850
CAGCCCTCCT AATGACCTCC GGCCTAGCCA TGTGATTTCA CTTCCACTCC   5900
AYAACSCTCC TYATACTAGG CCTACTAACC AACACACTAA CCATATACCA   5950
ATGATGGCGC GATGCTAACA CGAGTAAAGT CACATACCAA GGCCACCACA   6000
```

*Fig. 1E*

```
CACCACCTGT CCARAAAGGC CTTCGATACG GGATAATCCT ATTTATTACC 6050
TCAGAAGTTT TTTTCTTCGC AGGATTTTTC TGAGCCTTTT ACCACTCCAG 6100
CCTAGCTCCC TACCCCCCAA YTAGGRGGRC ACTGGCCCCS AACAGGCATC 6150
ACCCCGCTAA ATCCCCTAGA AGTCCCACTC CTAAACACAT CCGTATTACT 6200
CGCATCAGGR GTATCAATCA CCTGAGCTCA CCATAGTCTA ATAGAAAAAC 6250

AACCGAAACC AAATAATTCA AGCACTGCTT ATTACAATTT TACTGGGTCT 6300
CTATTTTACC CTCCTACAAG CCTCAGAGTA CTTCGAGGTT AAAATATTAG 6350
ATATTTCCCC TGATACAGGG CTCAATCTTT TTCTTTTTAA AGCAATATTT 6400
CTCAAAGTAC TTTTCACAGA ACTTAAGTTT CATTAAGCAC TTCACTAAAA 6450
GNAAAAGTCT GTGATCTAAT AAATTTGGAA AATATTGAGA ATTAGAGCCC 6500

CCTCTTAGAT ATGTACTGTA GCTACTCAGC TTGTTACAGA TGGAAGTAAA 6550
CATTGTAATA TTCACCCAGC TTTTGAGTGG ATGTCTATTA ACATCACCCA 6600
AATGAGTATT CCATGGAATG CACTTGCAA AAACCTATTA TTCAAGAAAA 6650
ATTCTGGAGC ATGGAAAGCT ATTAATGGAT AAACCCATTC ACAAAATCAC 6700
ACCAAATATC TAAAATCATG TTTAAAATCT CCTAGAAATG GGTT         6744
```

*Fig. 1F*

```
GATCACAGGTCTATCACCCTATTAACCACTCACGGGAGCTCTCCATGCATTTGGTATTTT
        10        20        30        40        50        60

CGTCTGGGGGGTATGCACGCGATAGCATTGCGAGACGCTGGAGCCGGAGCACCCTATGTC
        70        80        90       100       110       120

GCAGTATCTGTCTTTGATTCCTGCCTCATCCTATTATTTATCGCACCTACGTTCAATATT
       130       140       150       160       170       180

Origin of H strand
D Loop ──── replication
ACAGGCGAACATACTTACTAAAGTGTGTTAATTAATTAATGCTTGTAGGACATAATAATA
       190       200       210       220       230       240

ACAATTGAATGTCTGCACAGCCACTTTCCACACAGACATCATAACAAAAAATTTCCACCA
       250       260       270       280       290       300

AACCCCCCCTCCCCCGCTTCTGGCCACAGCACTTAAACACATCTCTGCCAAACCCCAAAA
       310       320       330       340       350       360

ACAAAGAACCCTAACACCAGCCTAACCAGATTTCAAATTTTATCTTTTGGCGGTATGCAC
       370       380       390       400       410       420

TTTTAACAGTCACCCCCCAACTAACACATTATTTTCCCCTCCCACTCCCATACTACTAAT
       430       440       450       460       470       480

CTCATCAATACAACCCCCGCCCATCCTACCCAGCACACACACACCGCTGCTAACCCCATA
       490       500       510       520       530       540

Phe
                                                    tRNA ───→
CCCCGAACCAACCAAACCCCAAAGACACCCCCCACAGTTTATGTAGCTTACCTCCTCAAA
       550       560       570       580       590       600

12S rRNA
GCAATACACTGAAAATGTTTAGACGGGCTCACATCACCCCATAAACAAATAGGTTTGGTC
       610       620       630       640       650       660
──→
CTAGCCTTTCTATTAGCTCTTAGTAAGATTACACATGCAAGCATCCCCGTTCCAGTGAGT
       670       680       690       700       710       720
```

*Fig. 2A*

```
TCACCCTCTAAATCACCACGATCAAAAGGGACAAGCATCAAGCACGCAGCAATGCAGCTC
     730       740       750       760       770       780

AAAACGCTTAGCCTAGCCACACCCCCACGGGAAACAGCAGTGATTAACCTTTAGCAATAA
     790       800       810       820       830       840

ACGAAAGTTTAACTAAGCTATACTAACCCCAGGGTTGGTCAATTTCGTGCCAGCCACCGC
     850       860       870       880       890       900

GGTCACACGATTAACCCAAGTCAATAGAAGCCGGCGTAAAGAGTGTTTTAGATCACCCCC
     910       920       930       940       950       960

TCCCCAATAAAGCTAAAACTCACCTGAGTTGTAAAAAACTCCAGTTGACACAAAATAGAC
     970       980       990      1000      1010      1020

TACGAAAGTGGCTTTAACATATCTGAACACACAATAGCTAAGACCCAAACTGGGATTAGA
    1030      1040      1050      1060      1070      1080

TACCCCACTATGCTTAGCCCTAAACCTCAACAGTTAAATCAACAAAACTGCTCGCCAGAA
    1090      1100      1100      1120      1130      1140

CACTACGAGCCACAGCTTAAAACTCAAAGGACCTGGCGGTGCTTCATATCCCTCTAGAGG
    1150      1160      1170      1180      1190      1200

AGCCTGTTCTGTAATCGATAAACCCCGATCAACCTCACCACCTCTTGCTCAGCCTATATA
    1210      1220      1230      1240      1250      1260

CCGCCATCTTCAGCAAACCCTGATGAAGGCTACAAAGTAAGCGCAAGTACCCACGTAAAG
    1270      1280      1290      1300      1310      1320

ACGTTAGGTCAAGGTGTAGCCCATGAGGTGGCAAGAAATGGGCTACATTTTCTACCCCAG
    1330      1340      1350      1360      1370      1380

AAAACTACGATAGCCCTTATGAAACTTAAGGGTCGAAGGTGGATTTAGCAGTAAACTAAG
    1390      1400      1410      1420      1430      1440

AGTAGAGTGCTTAGTTGAACAGGGCCCTGAAGCGCGTACACACCGCCCGTCACCCTCCTC
    1450      1460      1470      1480      1490      1500

AAGTATACTTCAAAGGACATTTAACTAAAACCCCTACGCATTTATATAGAGGAGACAAGT
    1510      1520      1530      1540      1550      1560
```

*Fig. 2B*

```
                                              Val
                                         tRNA ───▶
CGTAACATGGTAAGTGTACTGGAAAGTGCACTTGGACGAACCAGAGTGTAGCTTAACACA
    1570      1580      1590      1600      1610      1620

16S rRNA
AAGCACCCAACTTACACTTAGGAGATTTCAACTTAACTTGACCGCTCTGAGCTAAACCTA
    1630      1640      1650      1660      1670      1680
───▶
GCCCCAAACCCACTCCACCTTACTACCAGACAACCTTAGCCAAACCATTTACCCAAATAA
    1690      1700      1710      1720      1730      1740

AGTATAGGCGATAGAAATTGAAACCTGGCGCAATAGATATAGTACCGCAAGGGAAAGATG
    1750      1760      1770      1780      1790      1800

AAAAATTATAACCAAGCATAATATAGCAAGGACTAACCCCTATACCTTCTGCATAATGAA
    1810      1820      1830      1840      1850      1860

TTAACTAGAAATAACTTTGCAAGGAGAGCCAAAGCTAAGACCCCCGAAACCAGACGAGCT
    1870      1880      1890      1900      1910      1920

ACCTAAGAACAGCTAAAAGAGCACACCCGTCTATGTAGCAAAATAGTGGGAAGATTTATA
    1930      1940      1950      1960      1970      1980

GGTAGAGGCGACAAACCTACCGAGCCTGGTGATAGCTGGTTGTCCAAGATAGAATCTTAG
    1990      2000      2010      2020      2030      2040

TTCAACTTTAAATTTGCCCACAGAACCCTCTAAATCCCCTTGTAAATTTAACTGTTAGTC
    2050      2060      2070      2080      2090      2100

CAAAGAGGAACAGCTCTTTGGACACTAGGAAAAAACCTTGTAGAGAGAGTAAAAAATTTA
    2110      2120      2130      2140      2150      2160

ACACCCATAGTAGGCCTAAAAGCAGCCACCAATTAAGAAAGCGTTCAAGCTCAACACCCA
    2170      2180      2190      2200      2210      2220

CTACCTAAAAAATCCCAAACATATAACTGAACTCCTCACACCCAATTGGACCAATCTATC
    2230      2240      2250      2260      2270      2280

ACCCTATAGAAGAACTAATGTTAGTATAAGTAACATGAAAACATTCTCCTCCGCATAAGC
    2290      2300      2310      2320      2330      2340
```

*Fig. 2C*

```
CTGCGTCAGATTAAAACACTGAACTGACAATTAACAGCCCAATATCTACAATCAACCAAC
    2350      2360      2370      2380      2390      2400

AAGTCATTATTACCCTCACTGTCAACCCAACACAGGCATGCTCATAAGGAAAGGTTAAAA
    2410      2420      2430      2340      2350      2460

AAAGTAAAAGGAACTCGGCAAATCTTACCCCGCCTGTTTACCAAAAACATCACCTCTAGC
    2470      2480      2490      2500      2510      2520

ATCACCAGTATTAGAGGCACCGCCTGCCCAGTGACACATGTTTAACGGCCGCGGTACCCT
    2530      2540      2550      2560      2570      2580

AACCGTGCAAAGGTAGCATAATCACTTGTTCCTTAAATAGGGACCTGTATGAATGGCTCC
    2590      2600      2610      2620      2630      2640

ACGAGGGTTCAGCTGTCTCTTACTTTTAACCAGTGAAATTGACCTGCCCGTGAAGAGGCG
    2650      2660      2670      2680      2690      2700

GGCATAACACAGCAAGACGAGAAGACCCTATGGAGCTTTAATTTATTAATGCAAACAGTA
    2710      2720      2730      2740      2750      2760

CCTAACAAACCCACAGGTCCTAAACTACCAAACCTGCATTAAAAATTTCGGTTGGGGCGA
    2770      2780      2790      2800      2810      2820

CCTCGGAGCAGAACCCAACCTCCGAGCAGTACATGCTAAGACTTCACCAGTCAAAGCGAA
    2830      2840      2850      2860      2870      2880

CTACTATACTCAATTGATCCAATAACTTGACCAACGGAACAAGTTACCCTAGGGATAACA
    2890      2900      2910      2920      2930      2940

GCGCAATCCTATTCTAGAGTCCATATCAACAATAGGGTTTACGACCTCGATGTTGGATCA
    2950      2960      2970      2980      2990      3000

GGACATCCCGATGGTGCAGCCGCTATTAAAGGTTCGTTTGTTCAACGATTAAAGTCCTAC
    3010      3020      3030      3040      3050      3060

GTGATCTGAGTTCAGACCGGAGTAATCCAGGTCGGTTTCTATCTACCTTCAAATTCCTCC
    3070      3080      3090      3100      3110      3120

CTGTACGAAAGGACAAGAGAAATAAGGCCTACTTCACAAAGCGCCTTCCCCCGTAAATGA
    3130      3140      3150      3160      3170      3180
```

*Fig. 2D*

```
                                                           Leu(UUR)
                                                         tRNA ──────▶
TATCATCTCAACTTAGTATTATACCCACACCCACCCAAGAACAGGGTTT|GTTAAGATGGC
     3190      3200      3210      3220      3230      3240

AGAGCCCGGTAATCGCATAAAACTTAAAACTTTACAGTCAGAGGTTCAATTCCTCTTCTT
     3250      3260      3270      3280      3290      3300

U.R.F.1 ──────▶
          M  P  M  A  N  L  L  L  L  I  V  P  I  L  I  A  M  A
      AACA|ACATACCCATGGCCAACCTCCTACTCCTCATTGTACCCATTCTAATCGCAATGGCA
          | 3310      3320      3330      3340      3350      3360
          └─▶RNA13

F  L  M  L  T  E  R  K  I  L  G  Y  M  Q  L  R  K  G  P  N
  TTCCTAATGCTTACCGAACGAAAAATTCTAGGCTATATACAACTACGCAAAGGCCCCAAC
       3370      3380      3390      3400      3410      3420

V  V  G  P  Y  G  L  L  Q  P  F  A  D  A  M  K  L  F  T  K
  GTTGTAGGCCCCTACGGGCTACTACAACCCTTCGCTGACGCCATAAAACTCTTCACCAAA
       3430      3440      3450      3460      3470      3480

E  P  L  K  P  A  T  S  T  I  T  L  Y  I  T  A  P  T  L  A
  GAGCCCCTAAAACCCGCCACATCTACCATCACCCTCTACATCACCGCCCCGACCTTAGCT
       3490      3500      3510      3520      3530      3540

L  T  I  A  L  L  L  W  T  P  L  P  M  P  N  P  L  V  N  L
  CTCACCATCGCTCTTCTACTATGAACCCCCCTCCCCATACCCAACCCCCTGGTCAACCTC
       3550      3560      3570      3580      3590      3600

N  L  G  L  L  F  I  L  A  T  S  S  L  A  V  Y  S  I  L  W
  AACCTAGGCCTCCTATTTATTCTAGCCACCTCTAGCCTAGCCGTTTACTCAATCCTCTGA
       3610      3620      3630      3640      3650      3660

S  G  W  A  S  N  S  N  Y  A  L  I  G  A  L  R  A  V  A  Q
  TCAGGGTGAGCATCAAACTCAAACTACGCCCTGATCGGCGCACTGCGAGCAGTAGCCCAA
       3670      3680      3690      3700      3710      3720

T  I  S  Y  E  V  T  L  A  I  I  L  L  S  T  L  L  M  S  G
  ACAATCTCATATGAAGTCACCCTAGCCATCATTCTACTATCAACATTACTAATAAGTGGC
       3730      3740      3750      3760      3770      3780
```

Fig. 2E

```
             S   F   N   L   S   T   L   I   T   T   Q   E   H   L   W   L   L   L   P   S
           TCCTTTAACCTCTCCACCCTTATCACAACACAAGAACACCTCTGATTACTCCTGCCATCA
               3790      3800      3810      3820      3830      3840

W   P   L   A   M   M   W   F   I   S   T   L   A   E   T   N   R   T   P   F
           TGACCCTTGGCCATAATATGATTTATCTCCACACTAGCAGAGACCAACCGAACCCCCTTC
               3850      3860      3870      3880      3890      3900

D   L   A   E   G   E   S   E   L   V   S   G   F   N   I   E   Y   A   A   G
           GACCTTGCCGAAGGGGAGTCCGAACTAGTCTCAGGCTTCAACATCGAATACGCCGCAGGC
               3910      3920      3930      3940      3950      3960

P   F   A   L   F   F   M   A   E   Y   T   N   I   I   M   M   N   T   L   T
           CCCTTCGCCCTATTCTTCATAGCCGAATACACAAACATTATTATAATAAACACCCTCACC
               3970      3980      3990      4000      4010      4020

T   T   I   F   L   G   T   T   Y   D   A   L   S   P   E   L   Y   T   T   Y
           ACTACAATCTTCCTAGGAACAACATATGACGCACTCTCCCCTGAACTCTACACAACATAT
               4030      4040      4050      4060      4070      4080

F   V   T   K   T   L   L   L   T   S   L   F   L   W   I   R   T   A   Y   P
           TTTGTCACCAAGACCCTACTTCTAACCTCCCTGTTCTTATGAATTCGAACAGCATACCCC
               4090      4100      4110      4120      4130      4140

R   F   R   Y   D   Q   L   M   H   L   L   W   K   N   F   L   P   L   T   L
           CGATTCCGCTACGACCAACTCATACACCTCCTATGAAAAAACTTCCTACCACTCACCCTA
               4150      4160      4170      4180      4190      4200

A   L   L   M   W   Y   V   S   M   P   I   T   I   S   S   I   P   P   Q   T
           GCATTACTTATATGATATGTCTCCATACCCATTACAATCTCCAGCATTCCCCCTCAAACC
               4210      4220      4230      4240      4250      4260
                                                                        RNA13
                       Ile
                    tRNA ──▶
           TAAGAAATATGTCTGATAAAAGAGTTACTTTGATAGAGTAAATAATAGGAGCTTAAACCC
               4270      4280      4290      4300      4310      4320
            →
           CCTTATTTCTAGGACTATGAGAATCGAACCCATCCCTGAGAATCCAAAATTCTCCGTGCC
               4330      4340      4350      4360      4370      4380
```

*Fig. 2F*

```
                    Gln          f_Met
           ←─── tRNA       tRNA ───→
      ACCTATCACACCCCATCCTAAAGTAAGGTCAGCTAAATAAGCTATCGGGCCCATACCCCG
          4390      4400      4410      4420      4430      4440

U.R.F. 2 ───→
                                          I  N  P  L  A  Q  P  V  I  Y
      AAAATGTTGGTTATACCCTTCCCGTACTAATTAATCCCCTGGCCCAACCCGTCATCTACT
          4450      4460      4470      4480      4490      4500
                               ├──→ RNA12
```

S  T  I  F  A  G  T  L  I  T  A  L  S  S  H  W  F  F  T  W
CTACCATCTTTGCAGGCACACTCATCACAGCGCTAAGCTCGCACTGATTTTTTACCTGAG
    4510      4520      4530      4540      4550      4560

V  G  L  E  M  N  M  L  A  F  I  P  V  L  T  K  K  M  N  P
TAGGCCTAGAAATAAACATGCTAGCTTTTATTCCAGTTCTAACCAAAAAAATAAACCCTC
    4570      4580      4590      4600      4610      4620

R  S  T  E  A  A  I  K  Y  F  L  T  Q  A  T  A  S  M  I  L
GTTCCACAGAAGCTGCCATCAAGTATTTCCTCACGCAAGCAACCGCATCCATAATCCTTC
    4630      4640      4650      4660      4670      4680

L  M  A  I  L  F  N  N  M  L  S  G  Q  W  T  M  T  N  T  T
TAATAGCTATCCTCTTCAACAATATACTCTCCGGACAATGAACCATAACCAATACTACCA
    4690      4700      4710      4720      4730      4740

N  Q  Y  S  S  L  M  I  M  M  A  M  A  M  K  L  G  M  A  P
ATCAATACTCATCATTAATAATCATAATAGCTATAGCAATAAAACTAGGAATAGCCCCCT
    4750      4760      4770      4780      4790      4800

F  H  F  W  V  P  E  V  T  Q  G  T  P  L  T  S  G  L  L  L
TTCACTTCTGAGTCCCAGAGGTTACCCAAGGCACCCCTCTGACATCCGGCCTGCTTCTTC
    4810      4820      4830      4840      4850      4860

L  T  W  Q  K  L  A  P  I  S  I  M  Y  Q  I  S  P  S  L  N
TCACATGACAAAAACTAGCCCCCATCTCAATCATATACCAAATCTCTCCCTCACTAAACG
    4870      4880      4890      4900      4910      4920

V  S  L  L  L  T  L  S  I  L  S  I  M  A  G  S  W  G  G  L
TAAGCCTTCTCCTCACTCTCTCAATCTTATCCATCATAGCAGGCAGTTGAGGTGGATTAA
    4930      4940      4950      4960      4970      4980

*Fig. 2G*

```
  N   Q   T   Q   L   R   K   I   L   A   Y   S   S   I   T   H   M   G   W   M
ACCAGACCCAGCTACGCAAAATCTTAGCATACTCCTCAATTACCCACATAGGATGAATAA
     4990       5000       5010       5020       5030       5040

M   A   V   L   P   Y   N   P   N   M   T   I   L   N   L   T   I   Y   I   I
TAGCAGTTCTACCGTACAACCCTAACATAACCATTCTTAATTTAACTATTTATATTATCC
     5050       5060       5070       5080       5090       5100

L   T   T   T   A   F   L   L   N   L   N   S   S   T   T   T   L   L   L
TAACTACTACCGCATTCCTACTACTCAACTTAAACTCCAGCACCACGACCCTACTACTAT
     5110       5120       5130       5140       5150       5160

S   R   T   W   N   K   L   T   W   L   T   P   L   I   P   S   T   L   L   S
CTCGCACCTGAAACAAGCTAACATGACTAACACCCTTAATTCCATCCACCCTCCTCTCCC
     5170       5180       5190       5200       5210       5220

L   G   G   L   P   P   L   T   G   F   L   P   K   W   A   I   I   E   E   F
TAGGAGGCCTGCCCCCGCTAACCGGCTTTTTGCCCAAATGGGCCATTATCGAAGAATTCA
     5230       5240       5250       5260       5270       5280

T   K   N   N   S   L   I   I   P   T   I   M   A   T   I   T   L   L   N   L
CAAAAAACAATAGCCTCATCATCCCCACCATCATAGCCACCATCACCCTCCTTAACCTCT
     5290       5300       5310       5320       5330       5340

Y   F   Y   L   R   L   I   Y   S   T   S   I   T   L   L   P   M   S   N   N
ACTTCTACCTACGCCTAATCTACTCCACCTCAATCACACTACTCCCCATATCTAACAACG
     5350       5360       5370       5380       5390       5400

V   K   M   K   W   Q   F   E   H   T   K   P   T   P   F   L   P   T   L   I
TAAAAATAAAATGACAGTTTGAACATACAAAACCCACCCCATTCCTCCCCACACTCATCG
     5410       5420       5430       5440       5450       5460

Trp
  A   L   T   T   L   L   L   P   I   S   P   F   M   L   M   I   L  tRNA ──▶
CCCTTACCACGCTACTCCTACCTATCTCCCCTTTTATACTAATAATCTTAT AGAAATTTA
     5470       5480       5490       5500       5510       5520
                                                    RNA12 ──▶

GGTTAAATACAGACCAAGAGCCTTCAAAGCCCTCAGTAAGTTGCAATACTTAATTTCTG T
     5530       5540       5550       5560       5570       5580
```

*Fig. 2H*

```
AACAGC TAAGGACTGCAAAACCCCACTCTGCATCAACTGAACGCAAATCAGCCACTTTAA
       5590      5600      5610      5620      5630      5640

Ala
      ←—tRNA
TTAAGCTAAGCCCTTACTAGACCAATGGGACTTAAACCCACAAACACTTAGTTAACAGCT
     5650      5660      5670      5680      5690      5700

Asn         Origin of L strand
                   ←—tRNA          ┌replication ┌——————
AAGCACCCTAATCAACTGGCTTCAATCTA CTTCTCCCGCCGCCGGGAAAAAAGGCGGGAG
     5710      5720      5730      5740      5750      5760
                                                         ←——
AAGCCCCGGCAGGTTTGAAGCTGCTTCTTCGAATTTGCAATTCAATATGAAAATCACCTC
     5770      5780      5790      5800      5810      5820

Cys
 tRNA
GGAGCTGG T AAAAAGAGGCCTAACCCCTGTCTTTAGATTTACAGTCCAATGCTTCACTCA
     5830      5840      5850      5860      5870      5880

Tyr             CO I —→
    ←—tRNA          M  F  A  D  R  W  L  F  S  T  N  H
GCCATTTTACC TCACCCCCACTGATGTTCGCCGACCGTTGACTATTCTCTACAAACCACA
     5890      5900      5910      5920      5930      5940
                   ├——RNA9

K  D  I  G  T  L  Y  L  L  F  G  A  W  A  G  V  L  G  T  A
AAGACATTGGAACACTATACCTATTATTCGGCGCATGAGCTGGAGTCCTAGGCACAGCTC
     5950      5960      5970      5980      5990      6000

L  S  L  L  I  R  A  E  L  G  Q  P  G  N  L  L  G  N  D  H
TAAGCCTCCTTATTCGAGCCGAGCTGGGCCAGCCAGGCAACCTTCTAGGTAACGACCACA
     6010      6020      6030      6040      6050      6060

I  Y  N  V  I  V  T  A  H  A  F  V  M  I  F  F  M  V  M  P
TCTACAACGTTATCGTCACAGCCCATGCATTTGTAATAATCTTCTTCATAGTAATACCCA
     6070      6080      6090      6100      6110      6120

I  M  I  G  G  F  G  N  W  L  V  P  L  M  I  G  A  P  D  M
TCATAATCGGAGGCTTTGGCAACTGACTAGTTCCCCTAATAATCGGTGCCCCCGATATGG
     6130      6140      6150      6160      6170      6180
```

*Fig. 21*

```
  A   F   P   R   M   N   N   M   S   F   W   L   L   P   P   S   L   L   L   L
CGTTTCCCCGCATAAACAACATAAGCTTCTGACTCTTACCTCCCTCTCTCCTACTCCTGC
         6190        6200        6210        6220        6230        6240

L   A   S   A   M   V   E   A   G   A   G   T   G   W   T   V   Y   P   P   L
TCGCATCTGCTATAGTGGAGGCCGGAGCAGGAACAGGTTGAACAGTCTACCCTCCCTTAG
         6250        6260        6270        6280        6290        6300

A   G   N   Y   S   H   P   G   A   S   V   D   L   T   I   F   S   L   H   L
CAGGGAACTACTCCCACCCTGGAGCCTCCGTAGACCTAACCATCTTCTCCTTACACCTAG
         6310        6320        6330        6340        6350        6360

A   G   V   S   S   I   L   G   A   I   N   F   I   T   T   I   I   N   M   K
CAGGTGTCTCCTCTATCTTAGGGGCCATCAATTTCATCACAACAATTATCAATATAAAAC
         6370        6380        6390        6400        6410        6420

P   P   A   M   T   Q   Y   Q   T   P   L   F   V   W   S   V   L   I   T   A
CCCCTGCCATAACCCAATACCAAACGCCCCTCTTCGTCTGATCCGTCCTAATCACAGCAG
         6430        6440        6450        6460        6470        6480

V   L   L   L   L   S   L   P   V   L   A   A   G   I   T   M   L   L   T   D
TCCTACTTCTCCTATCTCTCCCAGTCCTAGCTGCTGGCATCACTATACTACTAACAGACC
         6490        6500        6510        6520        6530        6540

R   N   L   N   T   T   F   F   D   P   A   G   G   G   D   P   I   L   Y   Q
GCAACCTCAACACCACCTTCTTCGACCCCGCCGGAGGAGGAGACCCCATTCTATACCAAC
         6550        6560        6570        6580        6590        6600

H   L   F   W   F   F   G   H   P   E   V   Y   I   L   I   L   P   G   F   G
ACCTATTCTGATTTTTCGGTCACCCTGAAGTTTATATTCTTATCCTACCAGGCTTCGGAA
         6610        6620        6630        6640        6650        6660

M   I   S   H   I   V   T   Y   Y   S   G   K   K   E   P   F   G   Y   M   G
TAATCTCCCATATTGTAACTTACTACTCCGGAAAAAAAGAACCATTTGGATACATAGGTA
         6670        6680        6690        6700        6710        6720

M   V   W   A   M   M   S   I   G   F   L   G   F   I   V   W   A   H   H   M
TGGTCTGAGCTATGATATCAATTGGCTTCCTAGGGTTTATCGTGTGAGCACACCATATAT
         6730        6740        6750        6760        6770        6780
```

*Fig. 2J*

```
  F   T   V   G   M   D   V   D   T   R   A   Y   F   T   S   A   T   M   I   I
TTACAGTAGGAATAGACGTAGACACACGAGCATATTTCACCTCCGCTACCATAATCATCG
      6790      6800      6810      6820      6830      6840

A   I   P   T   G   V   K   V   F   S   W   L   A   T   L   H   G   S   N   M
CTATCCCCACCGGCGTCAAAGTATTTAGCTGACTCGCCACACTCCACGGAAGCAATATGA
      6850      6860      6870      6880      6890      6900

K   W   S   A   A   V   L   W   A   L   G   F   I   F   L   F   T   V   G   G
AATGATCTGCTGCAGTGCTCTGAGCCCTAGGATTCATCTTTCTTTTCACCGTAGGTGGCC
      6910      6920      6930      6940      6950      6960

L   T   G   I   V   L   A   N   S   S   L   D   I   V   L   H   D   T   Y   Y
TGACTGGCATTGTATTAGCAAACTCATCACTAGACATCGTACTACACGACACGTACTACG
      6970      6980      6990      7000      7010      7020

V   V   A   H   F   H   Y   V   L   S   M   G   A   V   F   A   I   M   G   G
TTGTAGCCCACTTCCACTATGTCCTATCAATAGGAGCTGTATTTGCCATCATAGGAGGCT
      7030      7040      7050      7060      7070      7080

F   I   H   W   F   P   L   F   S   G   Y   T   L   D   Q   T   Y   A   K   I
TCATTCACTGATTTCCCCTATTCTCAGGCTACACCCTAGACCAAACCTACGCCAAAATCC
      7090      7100      7110      7120      7130      7140

H   F   T   I   M   F   I   G   V   N   L   T   F   F   P   Q   H   F   L   G
ATTTCACTATCATATTCATCGGCGTAAATCTAACTTTCTTCCCACAACACTTTCTCGGCC
      7150      7160      7170      7180      7190      7200

L   S   G   M   P   R   R   Y   S   D   Y   P   D   A   Y   T   T   W   N   I
TATCCGGAATGCCCCGACGTTACTCGGACTACCCCGATGCATACACCACATGAAACATCC
      7210      7220      7230      7240      7250      7260

L   S   S   V   G   S   F   I   S   L   T   A   V   M   L   M   I   F   M   I
TATCATCTGTAGGCTCATTCATTTCTCTAACAGCAGTAATATTAATAATTTTCATGATTT
      7270      7280      7290      7300      7310      7320

W   E   A   F   A   S   K   R   K   V   L   M   V   E   E   P   S   M   N   L
GAGAAGCCTTCGCTTCGAAGCGAAAAGTCCTAATAGTAGAAGAACCCTCCATAAACCTGG
      7330      7340      7350      7360      7370      7380
```

*Fig. 2K*

```
          E   W   L   Y   G   C   P   P   P   Y   H   T   F   E   E   P   V   Y   M   K
        AGTGACTATATGGATGCCCCCCACCCTACCACACATTCGAAGAACCCGTATACATAAAAT
            7390      7400      7410      7420      7430      7440

S                                                                    ←
        CTAGACAAAAAAGGAAGGAATCGAACCCCCCAAAGCTGGTTTCAAGCCAACCCCATGGCC
            7450      7460      7470      7480      7490      7500

Ser(UCN)            Asp
        tRNA                tRNA ——→
        TCCATGACTTTTTCAAAAAGGTATTAGAAAAACCATTTCATAACTTTGTCAAAGTTAAAT
            7510     7520      7530      7540      7550      7560
            RNA9 ——→ |
                    ?           CO II ——→
                              M   A   H   A   A   Q   V   G   L   Q   D   A
        TATAGGCTAAATCCTATATATCTTAATGGCACATGCAGCGCAAGTAGGTCTACAAGACGC
            7570      7580    | 7590      7600      7610      7620
                              |——→RNA16

T   S   P   I   M   E   E   L   I   T   F   H   D   H   A   L   M   I   I   F
        TACTTCCCCTATCATAGAAGAGCTTATCACCTTTCATGATCACGCCCTCATAATCATTTT
            7630      7640      7650      7660      7670      7680

L   I   C   F   L   V   L   Y   A   L   F   L   T   L   T   T   K   L   T   N
        CCTTATCTGCTTCCTAGTCCTGTATGCCCTTTTCCTAACACTCACAACAAAACTAACTAA
            7690      7700      7710      7720      7730      7740

T   N   I   S   D   A   Q   E   M   E   T   V   W   T   I   L   P   A   I   I
        TACTAACATCTCAGACGCTCAGGAAATAGAAACCGTCTGAACTATCCTGCCCGCCATCAT
            7750      7760      7770      7780      7790      7800

L   V   L   I   A   L   P   S   L   R   I   L   Y   M   T   D   E   V   N   D
        CCTAGTCCTCATCGCCCTCCCATCCCTACGCATCCTTTACATAACAGACGAGGTCAACGA
            7810      7820      7830      7840      7850      7860

P   S   L   T   I   K   S   I   G   H   Q   W   Y   W   T   Y   E   Y   T   D
        TCCCTCCCTTACCATCAAATCAATTGGCCACCAATGGTACTGAACCTACGAGTACACCGA
            7870      7880      7890      7900      7910      7920

Y   G   G   L   I   F   N   S   Y   M   L   P   P   L   F   L   E   P   G   D
        CTACGGCGGACTAATCTTCAACTCCTACATACTTCCCCCATTATTCCTAGAACCAGGCGA
            7930      7940      7950      7960      7970      7980
```

*Fig. 2L*

```
       L  R  L  L  D  V  D  N  R  V  V  L  P  I  E  A  P  I  R  M
     CCTGCGACTCCTTGACGTTGACAATCGAGTAGTACTCCCGATTGAAGCCCCCATTCGTAT
         7990      8000      8010      8020      8030      8040

M  I  T  S  Q  D  V  L  H  S  W  A  V  P  T  L  G  L  K  T
     AATAATTACATCACAAGACGTCTTGCACTCATGAGCTGTCCCCACATTAGGCTTAAAAAC
         8050      8060      8070      8080      8090      8100

D  A  I  P  G  R  L  N  Q  T  T  F  T  A  T  R  P  G  V  Y
     AGATGCAATTCCCGGACGTCTAAACCAAACCACTTTCACCGCTACACGACCGGGGGTATA
         8110      8120      8130      8140      8150      8160

Y  G  Q  C  S  E  I  C  G  A  N  H  S  F  M  P  I  V  L  E
     CTACGGTCAATGCTCTGAAATCTGTGGAGCAAACCACAGTTTCATGCCCATCGTCCTAGA
         8170      8180      8190      8200      8210      8220

L  I  P  L  K  I  F  E  M  G  P  V  F  T  L  *
     ATTAATTCCCCTAAAAATCTTTGAAATAGGGCCCGTATTTACCCTATAGCACCCCCTCTA
         8230      8240      8250      8260      8270      8280

Lys
                            tRNA ─────▶
     CCCCCTCTAGAGCC┌CACTGTAAAGCTAACTTAGCATTAACCTTTTAAGTTAAAGATTAAG
         8290     │   8300      8310      8320      8330      8340
         RNA16 ──▶│

U.R.F. A6L ─────▶
                                  M  P  Q  L  N  T  T  V  W  P  T  M
     AGAACCAACACCTCTTTACAGTGA┐AATGCCCCAACTAAATACTACCGTATGGCCCACCAT
         8350      8360     │   8370      8380      8390      8400
                            └──▶ RNA14

I  T  P  M  L  L  T  L  F  L  I  T  Q  L  K  M  L  N  T  N
     AATTACCCCCATACTCCTTACACTATTCCTCATCACCCAACTAAAAATATTAAACACAAA
         8410      8420      8430      8440      8450      8460

Y  H  L  P  P  S  P  K  P  M  K  M  K  N  Y  N  K  P  W  E
     CTACCACCTACCTCCCTCACCAAAGCCCATAAAAATAAAAAATTATAACAAACCCTGAGA
         8470      8480      8490      8500      8510      8520
```

*Fig. 2M*

ATPase 6 →
```
              M  N  E  N  L  F  A  S  F  I  A  P  T  I  L  G  L  P
  P  K  W  T  K  I  C  S  L  H  S  L  P  P  Q  S  *
ACCAAAATGAACGAAAATCTGTTCGCTTCATTCATTGCCCCCACAATCCTAGGCCTACCC
   8530      8540      8550      8560      8570      8580

A  A  V  L  I  I  L  F  P  P  L  L  I  P  T  S  K  Y  L  I
GCCGCAGTACTGATCATTCTATTTCCCCCTCTATTGATCCCCACCTCCAAATATCTCATC
   8590      8600      8610      8620      8630      8640

N  N  R  L  I  T  T  Q  Q  W  L  I  K  L  T  S  K  Q  M  M
AACAACCGACTAATCACCACCCAACAATGACTAATCAAACTAACCTCAAAACAAATGATA
   8650      8660      8670      8680      8690      8700

T  M  H  N  T  K  G  R  T  W  S  L  M  L  V  S  L  I  I  F
ACCATACACAACACTAAAGGACGAACCTGATCTCTTATACTAGTATCCTTAATCATTTTT
   8710      8720      8730      8740      8750      8760

I  A  T  T  N  L  L  G  L  L  P  H  S  F  T  P  T  T  Q  L
ATTGCCACAACTAACCTCCTCGGACTCCTGCCTCACTCATTTACACCAACCACCCAACTA
   8770      8780      8790      8800      8810      8820

S  M  N  L  A  M  A  I  P  L  W  A  G  T  V  I  M  G  F  R
TCTATAAACCTAGCCATGGCCATCCCCCTTATGAGCGGGCACAGTGATTATAGGCTTTCGC
   8830      8840      8850      8860      8870      8880

S  K  I  K  N  A  L  A  H  F  L  P  Q  G  T  P  T  P  L  I
TCTAAGATTAAAAATGCCCTAGCCCACTTCTTACCACAAGGCACACCTACACCCCTTATC
   8890      8900      8910      8920      8930      8940

P  M  L  V  I  I  E  T  I  S  L  L  I  Q  P  M  A  L  A  V
CCCATACTAGTTATTATCGAAACCATCAGCCTACTCATTCAACCAATAGCCCTGGCCGTA
   8950      8960      8970      8980      8990      9000

R  L  T  A  N  I  T  A  G  H  L  L  M  H  L  I  G  S  A  T
CGCCTAACCGCTAACATTACTGCAGGCCACCTACTCATGCACCTAATTGGAAGCGCCACC
   9010      9020      9030      9040      9050      9060

L  A  M  S  T  I  N  L  P  S  T  L  I  I  F  T  I  L  I  L
CTAGCAATATCAACCATTAACCTTCCCTCTACACTTATCATCTTCACAATTCTAATTCTA
   9070      9080      9090      9100      9110      9120
```

*Fig. 2N*

```
    L   T   I   L   E   I   A   V   A   L   I   Q   A   Y   V   F   T   L   L   V
CTGACTATCCTAGAAATCGCTGTCGCCTTAATCCAAGCCTACGTTTTCACACTTCTAGTA
    9130      9140      9150      9160      9170      9180

S   L   Y   L   H   D   N   T      CO III ⎯⎯⎯►
                                    M   T   H   Q   S   H   A   Y   H   M   V
AGCCTCTACCTGCACGACAACACATAATGACCCACCAATCACATGCCTATCATATAGTAA
    9190      9200      ⁞9210      9220      9230      9240
                  RNA14 ⎯⎯⎯⎯⎯⎯⎯⎯⎯⎯►  RNA15

K   P   S   P   W   P   L   T   G   A   L   S   A   L   L   M   T   S   G   L
AACCCAGCCCATGACCCCTAACAGGGGCCCTCTCAGCCCTCCTAATGACCTCCGGCCTAG
    9250      9260      9270      9280      9290      9300

A   M   W   F   H   F   H   S   M   T   L   L   M   L   G   L   L   T   N   T
CCATGTGATTTCACTTCCACTCCATAACGCTCCTCATACTAGGCCTACTAACCAACACAC
    9310      9320      9330      9340      9350      9360

L   T   M   Y   Q   W   W   R   D   V   T   R   E   S   T   Y   Q   G   H   H
TAACCATATACCAATGATGGCGCGATGTAACACGAGAAAGCACATACCAAGGCCACCACA
    9370      9380      9390      9400      9410      9420

T   P   P   V   Q   K   G   L   R   Y   G   M   I   L   F   I   T   S   E   V
CACCACCTGTCCAAAAAGGCCTTCGATACGGGATAATCCTATTTATTACCTCAGAAGTTT
    9430      9440      9450      9460      9470      9480

F   F   F   A   G   F   F   W   A   F   Y   H   S   S   L   A   P   T   P   Q
TTTTCTTCGCAGGATTTTTCTGAGCCTTTTACCACTCCAGCCTAGCCCCTACCCCCCAAT
    9490      9500      9510      9520      9530      9540

L   G   G   H   W   P   P   T   G   I   T   P   L   N   P   L   E   V   P   L
TAGGAGGGCACTGGCCCCCAACAGGCATCACCCCGCTAAATCCCCTAGAAGTCCCACTCC
    9550      9560      9570      9580      9590      9600

L   N   T   S   V   L   L   A   S   G   V   S   I   T   W   A   H   H   S   L
TAAACACATCCGTATTACTCGCATCAGGAGTATCAATCACCTGAGCTCACCATAGTCTAA
    9610      9620      9630      9640      9650      9660

M   E   N   N   R   N   Q   M   I   Q   A   L   L   I   T   I   L   L   G   L
TAGAAAACAACCGAAACCAAATAATTCAAGCACTGCTTATTACAATTTTACTGGGTCTCT
    9670      9680      9690      9700      9710      9720
```

*Fig. 20*

```
Y  F  T  L  L  Q  A  S  E  Y  F  E  S  P  F  T  I  S  D  G
ATTTTACCCTCCTACAAGCCTCAGAGTACTTCGAGTCTCCCTTCACCATTTCCGACGGCA
    9730      9740      9750      9760      9770      9780

I  Y  G  S  T  F  F  V  A  T  G  F  H  G  L  H  V  I  I  G
TCTACGGCTCAACATTTTTTGTAGCCACAGGCTTCCACGGACTTCACGTCATTATTGGCT
    9790      9800      9810      9820      9830      9840

S  T  F  L  T  I  C  F  I  R  Q  L  M  F  H  F  T  S  K  H
CAACTTTCCTCACTATCTGCTTCATCCGCCAACTAATATTTCACTTTACATCCAAACATC
    9850      9860      9870      9880      9890      9900

H  F  G  F  E  A  A  A  W  Y  W  H  F  V  D  V  V  W  L  F
ACTTTGGCTTCGAAGCCGCCGCCTGATACTGGCATTTTGTAGATGTGGTTTGACTATTTC
    9910      9920      9930      9940      9950      9960

Glu
L  Y  V  S  I  Y  W  W  G  S          tRNA ──────▶
TGTATGTCTCCATCTATTGATGAGGGTCTTACTCTTTTAGTATAAATAGTACCGTTAACT
    9970      9980      999 0      10000      10010      10020
                    RNA15 ──────▶

U.R.F. 3 ──────▶
                                              M  N  F  A  L  I  L
TCCAATTAACTAGTTTTGACAACATTCAAAAAAGAGTA ATAAACTTCGCCCTTAATTTTAA
    10030     10040     10050     10060      10070     10080
                                          ├──▶RNA17

M  I  N  T  L  L  A  L  L  L  M  I  I  T  F  W  L  P  Q  L
TAATCAACACCCTCCTAGCCTTACTACTAATAATTATTACATTTTGACTACCACAACTCA
    10090     10100     10110     10120     10130     10140

N  G  Y  M  E  K  S  T  P  Y  E  C  G  F  D  P  M  S  P  A
ACGGCTACATAGAAAAATCCACCCCTTACGAGTGCGGCTTCGACCCTATATCCCCCGCCC
    10150     10160     10170     10180     10190     10200

R  V  P  F  S  M  K  F  F  L  V  A  I  T  F  L  L  F  D  L
GCGTCCCTTTCTCCATAAAATTCTTCTTAGTAGCTATTACCTTCTTATTATTTGATCTAG
    10210     10220     10230     10240     10250     10260
```

*Fig. 2P*

```
               E   I   A   L   L   L   P   L   P   W   A   L   Q   T   T   N   L   P   L   M
             AAATTGCCCTCCTTTTACCCCTACCATGAGCCCTACAAACAACTAACCTGCCACTAATAG
                 10270     10280     10290     10300     10310     10320

V   M   S   S   L   L   L   I   I   I   L   A   L   S   L   A   Y   E   W   L
 TTATGTCATCCCTCTTATTAATCATCATCCTAGCCCTAAGTCTGGCCTATGAGTGACTAC
     10330     10340     10350     10360     10370     10380

Arg
   Q   K   G   L   D   W   T   E                         tRNA  ──▶
 AAAAAGGATTAGACTGAACCGAAT TGGTATATAGTTTAAACAAAACGAATGATTTCGACT
     10390     10400     10410     10420     10430     10440

U.R.F. 4L ──▶
                                              M   P   L   I   Y   M   N   I   M   L
 CATTAAATTATGATAATCATATTTACCAA ATGCCCCTCATTTACATAAATATTATACTAG
     10450     10460     10470     10480     10490     10500
                              ├──▶ RNA7

A   F   T   I   S   L   L   G   M   L   V   Y   R   S   H   L   M   S   S   L
 CATTTACCATCTCACTTCTAGGAATACTAGTATATCGCTCACACCTCATATCCTCCCTAC
     10510     10520     10530     10540     10550     10560

L   C   L   E   G   M   M   L   S   L   F   I   M   A   T   L   M   T   L   N
 TATGCCTAGAAGGAATAATACTATCGCTGTTCATTATAGCTACTCTCATAACCCTCAACA
     10570     10580     10590     10600     10610     10620

T   H   S   L   L   A   N   I   V   P   I   A   M   L   V   F   A   A   C   E
 CCCACTCCCTCTTAGCCAATATTGTGCCTATTGCCATACTAGTCTTTGCCGCCTGCGAAG
     10630     10640     10650     10660     10670     10680

A   A   V   G   L   A   L   L   V   S   I   S   N   T   Y   G   L   D   Y   V
 CAGCGGTGGGCCTAGCCCTACTAGTCTCAATCTCCAACACATATGGCCTAGACTACGTAC
     10690     10700     10710     10720     10730     10740

U.R.F. 4 ──▶
                                              M   L   K   L   I   V   P   T   I   M   L   L   P   L
   H   N   L   N   L   L   Q   C
 ATAACCTAAACCTACTCCAATGCTAAAACTAATCGTCCCAACAATTATATTACTACCACT
     10750     10760     10770     10780     10790     10800
```

*Fig. 2Q*

```
      T   W   L   S   K   K   H   M   I   W   I   N   T   T   T   H   S   L   I   I
GACATGACTTTCCAAAAAACACATAATTTGAATCAACACAACCACCCACAGCCTAATTAT
      10810     10820     10830     10840     10850     10860

S   I   I   P   L   L   F   F   N   Q   I   N   N   N   L   F   S   C   S   P
TAGCATCATCCCTCTACTATTTTTTAACCAAATCAACAACAACCTATTTAGCTGTTCCCC
      10870     10880     10890     10900     10910     10920

T   F   S   S   D   P   L   T   T   P   L   L   M   L   T   T   W   L   L   P
AACCTTTTCCTCCGACCCCCTAACAACCCCCCTCCTAATACTAACTACCTGACTCCTACC
      10930     10940     10950     10960     10970     10980

L   T   I   M   A   S   Q   R   H   L   S   S   E   P   L   S   R   K   K   L
CCTCACAATCATGGCAAGCCAACGCCACTTATCCAGTGAACCACTATCACGAAAAAAACT
      10990     11000     11010     11020     10300     11040

Y   L   S   M   L   I   S   L   Q   I   S   L   I   M   T   F   T   A   T   E
CTACCTCTCTATACTAATCTCCCTACAAATCTCCTTAATTATAACATTCACAGCCACAGA
      11050     11060     11070     11080     11090     11100

L   I   M   F   Y   I   F   F   E   T   T   L   I   P   T   L   A   I   I   T
ACTAATCATATTTTATATCTTCTTCGAAACCACACTTATCCCCACCTTGGCTATCATCAC
      11110     11120     11130     11140     11150     11160

R   W   G   N   Q   P   E   R   L   N   A   G   T   Y   F   L   F   Y   T   L
CCGATGAGGCAACCAGCCAGAACGCCTGAACGCAGGCACATACTTCCTATTCTACACCCT
      11170     11180     11190     11200     11210     11220

V   G   S   L   P   L   L   I   A   L   I   Y   T   H   N   T   L   G   S   L
AGTAGGCTCCCTTCCCCTACTCATCGCACTAATTTACACTCACAACACCCTAGGCTCACT
      11230     11240     11250     11260     11270     11280

N   I   L   L   L   T   L   T   A   Q   E   L   S   N   S   W   A   N   N   L
AAACATTCTACTACTCACTCTCACTGCCCAAGAACTATCAAACTCCTGAGCCAATAACTT
      11290     11300     11310     11320     11330     11340

M   W   L   A   Y   T   M   A   F   M   V   K   M   P   L   Y   G   L   H   L
AATATGACTAGCTTACACAATAGCTTTTATAGTAAAGATACCTCTTTACGGACTCCACTT
      11350     11360     11370     11380     11390     11400
```

*Fig. 2R*

```
         W  L  P  K  A  H  V  E  A  P  I  A  G  S  M  V  L  A  A  V
       ATGACTCCCTAAAGCCCATGTCGAAGCCCCCATCGCTGGGTCAATAGTACTTGCCGCAGT
            11410     11420     11430     11440     11450     11460

L  L  K  L  G  G  Y  G  M  M  R  L  T  L  I  L  N  P  L  T
       ACTCTTAAAACTAGGCGGCTATGGTATAATACGCCTCACACTCATTCTCAACCCCCTGAC
            11470     11480     11490     11500     11510     11520

K  H  M  A  Y  P  F  L  V  L  S  L  W  G  M  I  M  T  S  S
       AAAACACATAGCCTACCCCTTCCTTGTACTATCCCTATGAGGCATAATTATAACAAGCTC
            11530     11540     11550     11560     11570     11580

I  C  L  R  Q  T  D  L  K  S  L  I  A  Y  S  S  I  S  H  M
       CATCTGCCTACGACAAACAGACCTAAAATCGCTCATTGCATACTCTTCAATCAGCCACAT
            11590     11600     11610     11620     11630     11640

A  L  V  V  T  A  I  L  I  Q  T  P  W  S  F  T  G  A  V  I
       AGCCCTCGTAGTAACAGCCATTCTCATCCAAACCCCCTGAAGCTTCACCGGCGCAGTCAT
            11650     11660     11670     11680     11690     11700

L  M  I  A  H  G  L  T  S  S  L  L  F  C  L  A  N  S  N  Y
       TCTCATAATCGCCCACGGGCTTACATCCTCATTACTATTCTGCCTAGCAAACTCAAACTA
            11710     11720     11730     11740     11750     11760

E  R  T  H  S  R  I  M  I  L  S  Q  G  L  Q  T  L  L  P  L
       CGAACGCACTCACAGTCGCATCATAATCCTCTCTCAAGGACTTCAAACTCTACTCCCACT
            11770     11780     11790     11800     11810     11820

M  A  F  W  W  L  L  A  S  L  A  N  L  A  L  P  P  T  I  N
       AATAGCTTTTTGATGACTTCTAGCAAGCCTCGCTAACCTCGCCTTACCCCCCACTATTAA
            11830     11840     11850     11860     11870     11880

L  L  G  E  L  S  V  L  V  T  T  F  S  W  S  N  I  T  L  L
       CCTACTGGGAGAACTCTCTGTGCTAGTAACCACGTTCTCCTGATCAAATATCACTCTCCT
            11890     11900     11910     11920     11930     11940

L  T  G  L  N  M  L  V  T  A  L  Y  S  L  Y  M  F  T  T  T
       ACTTACAGGACTCAACATACTAGTCACAGCCCTATACTCCCTCTACATATTTACCACAAC
            11950     11960     11970     11980     11990     12000
```

*Fig. 2S*

```
         Q  W  G  S  L  T  H  H  I  N  N  M  K  P  S  F  T  R  E  N
        ACAATGGGGCTCACTCACCCACCACATTAACAACATAAAACCCTCATTCACACGAGAAAA
            12010     12020     12030     12040     12050     12060

T  L  M  F  M  H  L  S  P  I  L  L  L  S  L  N  P  D  I  I
        CACCCTCATGTTCATACACCTATCCCCCATTCTCCTCCTATCCCTCAACCCCGACATCAT
            12070     12080     12090     12100     12110     12120

Hrs
         T  G  F  S  S          tRNA ───►
        TACCGGGTTTTCCTCTT GTAAATATAGTTTAACCAAAACATCAGATTGTGAATCTGACAA
            12130     12 140     12150     12160     12170     12180
               RNA7 ───►
```

```
                                    Ser(AGY)
                              tRNA ───►
        CAGAGGCTTACGACCCCTTATTTACC GAGAAAGCTCACAAGAACTGCTAACTCATGCCCC
            12190     12200     12210     12220     12230     12240
```

```
                                    Leu(CUN)
                              tRNA ───►
        CATGTCTAACAACATGGCTTTCTCA ACTTTTAAAGGATAACAGCTATCCATTGGTCTTAG
            12250     12260     12270     12280     12290     12300
```

```
                                                       U.R.F. 5 ───►
                                                       M  T  M  H  T  T  M  T
        GCCCCAAAAATTTTGGTGCAACTCCAAATAAAAGTAA TAACCATGCACACTACTATAACC
            12310     12320     12330     12 340     12350     12360
                                                 ├──► RNA5

T  L  T  L  T  S  L  I  P  P  I  L  T  T  L  V  N  P  N  K
        ACCCTAACCCTGACTTCCCTAATTCCCCCCATCCTTACCACCCTCGTTAACCCTAACAAA
            12370     12380     12390     12400     12410     12420

K  N  S  Y  P  H  Y  V  K  S  I  V  A  S  T  F  I  I  S  L
        AAAAACTCATACCCCCATTATGTAAAATCCATTGTCGCATCCACCTTTATTATCAGTCTC
            12430     12440     12450     12460     12470     12480

F  P  T  T  M  F  M  C  L  D  Q  E  V  I  I  S  N  W  H  W
        TTCCCCACAACAATATTCATGTGCCTAGACCAAGAAGTTATTATCTCGAACTGACACTGA
            12490     12500     12510     12520     12530     12540
```

*Fig. 2T*

```
      A   T   T   Q   T   T   Q   L   S   L   S   F   K   L   D   Y   F   S   M   M
    GCCACAACCCAAACAACCCAGCTCTCCCTAAGCTTCAAACTAGACTACTTCTCCATAATA
         12550     12560     12570     12580     12590     12600

F   I   P   V   A   L   F   V   T   W   S   I   M   E   F   S   L   W   Y   M
    TTCATCCCTGTAGCATTGTTCGTTACATGGTCCATCATAGAATTCTCACTGTGATATATA
         12610     12620     12630     12640     12650     12660

N   S   D   P   N   I   N   Q   F   F   K   Y   L   L   I   F   L   I   T   M
    AACTCAGACCCAAACATTAATCAGTTCTTCAAATATCTACTCATCTTCCTAATTACCATA
         12670     12680     12690     12700     12710     12720

L   I   L   V   T   A   N   N   L   F   Q   L   F   I   G   W   E   G   V   G
    CTAATCTTAGTTACCGCTAACAACCTATTCCAACTGTTCATCGGCTGAGAGGGCGTAGGA
         12730     12740     12750     12760     12770     12780

I   M   S   F   L   L   I   S   W   W   Y   A   R   A   D   A   N   T   A   A
    ATTATATCCTTCTTGCTCATCAGTTGATGATACGCCCGAGCAGATGCCAACACAGCAGCC
         12790     12800     12810     12820     12830     12840

I   Q   A   I   L   Y   N   R   I   G   D   I   G   F   I   L   A   L   A   W
    ATTCAAGCAATCCTATACAACCGTATCGGCGATATCGGTTTCATCCTCGCCTTAGCATGA
         12850     12860     12870     12880     12890     12900

F   I   L   H   S   N   S   W   D   P   Q   Q   M   A   L   L   N   A   N   P
    TTTATCCTACACTCCAACTCATGAGACCCACAACAAATAGCCCTTCTAAACGCTAATCCA
         12910     12920     12930     12940     12950     12960

S   L   T   P   L   L   G   L   L   L   A   A   A   G   K   S   A   Q   L   G
    AGCCTCACCCCACTACTAGGCCTCCTCCTAGCAGCAGCAGGCAAATCAGCCCAATTAGGT
         12970     12980     12990     13000     13010     13020

L   H   P   W   L   P   S   A   M   E   G   P   T   P   V   S   A   L   L   H
    CTCCACCCCTGACTCCCCTCAGCCATAGAAGGCCCCACCCCAGTCTCAGCCCTACTCCAC
         13030     13040     13050     13060     13070     13080

S   S   T   M   V   V   A   G   I   F   L   L   I   R   F   H   P   L   A   E
    TCAAGCACTATAGTTGTAGCAGGAATCTTCTTACTCATCCGCTTCCACCCCCTAGCAGAA
         13090     13100     13110     13120     13130     13140
```

*Fig. 2U*

```
   N  S  P  L  I  Q  T  L  T  L  C  L  G  A  I  T  T  L  F  A
AATAGCCCACTAATCCAAACTCTAACACTATGCTTAGGCGCTATCACCACTCTGTTCGCA
    13150     13160     13170     13180     13190     13200

A  V  C  A  L  T  Q  N  D  I  K  K  I  V  A  F  S  T  S  S
GCAGTCTGCGCCCTTACACAAAATGACATCAAAAAAATCGTAGCCTTCTCCACTTCAAGT
    13210     13220     13230     13240     13250     13260

Q  L  G  L  M  M  V  T  I  G  I  N  Q  P  H  L  A  F  L  H
CAACTAGGACTCATAATAGTTACAATCGGCATCAACCAACCACACCTAGCATTCCTGCAC
    13270     13280     13290     13300     13310     13320

I  C  T  H  A  F  F  K  A  M  L  F  M  C  S  G  S  I  I  H
ATCTGTACCCACGCCTTCTTCAAAGCCATACTATTTATGTGCTCCGGGTCCATCATCCAC
    13330     13340     13350     13360     13370     13380

N  L  N  N  E  Q  D  I  R  K  M  G  G  L  L  K  T  M  P  L
AACCTTAACAATGAACAAGATATTCGAAAAATAGGAGGACTACTCAAAACCATACCTCTC
    13390     13400     13410     13420     13430     13440

T  S  T  S  L  T  I  G  S  L  A  L  A  G  M  P  F  L  T  G
ACTTCAACCTCCCTCACCATTGGCAGCCTAGCATTAGCAGGAATACCTTTCCTCACAGGT
    13450     13460     13470     13480     13490     13500

F  Y  S  K  D  H  I  I  E  T  A  N  M  S  Y  T  N  A  W  A
TTCTACTCCAAAGACCACATCATCGAAACCGCAAACATATCATACACAAACGCCTGAGCC
    13510     13520     13530     13540     13550     13560

L  S  I  T  L  I  A  T  S  L  T  S  A  Y  S  T  R  M  I  L
CTATCTATTACTCTCATCGCTACCTCCCTGACAAGCGCCTATAGCACTCGAATAATTCTT
    13570     13580     13590     13600     13610     13620

L  T  L  T  G  Q  P  R  F  P  T  L  T  N  I  N  E  N  N  P
CTCACCCTAACAGGTCAACCTCGCTTCCCCACCCTTACTAACATTAACGAAAATAACCCC
    13630     13640     13650     13660     13670     13680

T  L  L  N  P  I  K  R  L  A  A  G  S  L  F  A  G  F  L  I
ACCCTACTAAACCCCATTAAACGCCTGGCAGCCGGAAGCCTATTCGCAGGATTTCTCATT
    13690     13700     13710     13720     13730     13740
```

*Fig. 2V*

```
  T  N  N  I  S  P  A  S  P  F  Q  T  T  I  P  L  Y  L  K  L
ACTAACAACATTTCCCCCGCATCCCCCTTCCAAACAACAATCCCCCTCTACCTAAAACTC
    13750     13760     13770     13789     13790     13800

T  A  L  A  V  T  F  L  G  L  L  T  A  L  D  L  N  Y  L  T
ACAGCCCTCGCTGTCACTTTCCTAGGACTTCTAACAGCCCTAGACCTCAACTACCTAACC
    13810     13820     13830     13840     13850     13860

N  K  L  K  M  K  S  P  L  C  T  F  Y  F  S  N  M  L  G  F
AACAAACTTAAAATAAAATCCCCACTATGCACATTTTATTTCTCCAACATACTCGGATTC
    13870     13880     13890     13900     13910     13920

Y  P  S  I  T  H  R  T  I  P  Y  L  G  L  L  T  S  Q  N  L
TACCCTAGCATCACACACCGCACAATCCCCTATCTAGGCCTTCTTACGAGCCAAAACCTG
    13930     13940     13950     13960     13970     13980

P  L  L  L  L  D  L  T  W  L  E  K  L  L  P  K  T  I  S  Q
CCCCTACTCCTCCTAGACCTAACCTGACTAGAAAAGCTATTACCTAAAACAATTTCACAG
    13990     14000     14010     14020     14030     14040

H  Q  I  S  T  S  I  I  T  S  T  Q  K  G  M  I  K  L  Y  F
CACCAAATCTCCACCTCCATCATCACCTCAACCCAAAAAGGCATAATTAAACTTTACTTC
    14050     14060     14070     14080     14090     14100

End U.R.F. 5 ——  —— End U.R.F. 6
  L  S  F  F  F  P  L  I  L  T  L  L  L  I  T  *  *  N  G  R
CTCTCTTTCTTCTTCCCACTCATCCTAACCCTACTCCTAATCACATAACCTATTCCCCCG
    14110     14120     14130     14140     14150     14160

A  I  E  I  V  I  Y  V  G  V  F  L  T  W  G  T  V  V  V  L
AGCAATCTCAATTACAATATATACACCAACAAACAATGTTCAACCAGTAACTACTACTAA
    14170     14180     14190     14200     15210     14220

W  R  G  Y  D  Y  L  A  G  A  G  I  P  D  E  R  I  L  G  S
TCAACGCCCATAATCATACAAAGCCCCCGCACCAATAGGATCCTCCCGAATCAACCCTGA
    14230     14240     14250     14260     14270     14280

G  E  G  E  Y  I  M  W  S  G  V  S  N  F  N  V  V  V  V  V
CCCCTCTCCTTCATAAATTATTCAGCTTCCTACACTATTAAAGTTTACCACAACCACCAC
    14290     14300     14310     14320     14330     14340
```

*Fig. 2W*

```
           G  D  Y  E  K  V  W  L  V  L  G  V  E  M  A  L  G  V  L  V
         CCCATCATACTCTTTCACCCACAGCACCAATCCTACCTCCATCGCTAACCCCACTAAAAC
           14350     14360     14370     14380     14390     14400

S  V  L  V  E  V  G  S  G  W  A  E  P  Y  E  E  I  A  M  A
         ACTCACCAAGACCTCAACCCCTGACCCCCATGCCTCAGGATACTCCTCAATAGCCATCGC
           14410     14420     14430     14440     14450     14460

T  T  Y  G  F  V  V  M  M  G  G  L  Y  I  L  F  V  M  L  G
         TGTAGTATATCCAAAGACAACCATCATTCCCCCTAAATAAATTAAAAAAACTATTAAACC
           14470     14480     14490     14500     14510     14520

M  Y  G  G  F  N  L  I  I  V  C  G  V  V  G  S  V  I  L
         CATATAACCTCCCCCAAAATTCAGAATAATAACACACCCGACCACACCGCTAACAATCAA
           14530     14540     14550     14560     14570     14580

V  L  G  G  Y  I  P  S  P  K  S  S  F  G  V  F  G  M  V  L
         TACTAAACCCCCATAAATAGGAGAAGGCTTAGAAGAAAACCCCACAAACCCCATTACTAA
           14590     14600     14610     14620     14630     14640

◄——— U.R.F. 6
           G  V  S  L  L  F  L  A  Y  M  M
         ACCCACACTCAACAGAAACAAAGCATACATCAT│TATTCTCGCACGGACTACAACCACGAC
           14650     14660     14670     14680     14690     14700

Glu              Cyt b ——►
                                        ◄——— tRNA                  M  T  P  M  R
         CAATGATATGAAAAACCATCGTTGTATTTCAACTACAAGAA│ACCAATGACCCCAATACG
           14710     14720     14730     14740     │14750     14760
                                                   ├——► RNA11

K  I  N  P  L  M  K  L  I  N  H  S  F  I  D  L  P  T  P  S
         CAAAATTAACCCCCTAATAAAATTAATTAACCACTCATTCATCGACCTCCCCACCCCATC
           14770     14780     14790     14800     14810     14820

N  I  S  A  W  W  N  F  G  S  L  L  G  A  C  L  I  L  Q  I
         CAACATCTCCGCATGATGAAACTTCGGCTCACTCCTTGGCGCCTGCCTGATCCTCCAAAT
           14830     14840     14850     14860     14870     14880

T  T  G  L  F  L  A  M  H  Y  S  P  D  A  S  T  A  F  S  S
         CACCACAGGACTATTCCTAGCCATGCACTACTCACCAGACGCCTCAACCGCCTTTTCATC
           14890     14900     14910     14920     14930     14940
```

*Fig. 2X*

```
      I   A   H   I   T   R   D   V   N   Y   G   W   I   I   R   Y   L   H   A   N
AATCGCCCACATCACTCGAGACGTAAATTATGGCTGAATCATCCGCTACCTTCACGCCAA
         14950       14960       14970       14980       14990       15000

G   A   S   M   F   F   I   C   L   F   L   H   I   G   R   G   L   Y   Y   G
TGGCGCCTCAATATTCTTTATCTGCCTCTTCCTACACATCGGGCGAGGCCTATATTACGG
         15010       15020       15030       15040       15050       15060

S   F   L   Y   S   E   T   W   N   I   G   I   I   L   L   L   A   T   M   A
ATCATTTCTCTACTCAGAAACCTGAAACATCGGCATTATCCTCCTGCTTGCAACTATAGC
         15070       15080       15090       15100       15110       15120

T   A   F   M   G   Y   V   L   P   W   G   Q   M   S   F   W   G   A   T   V
AACAGCCTTCATAGGCTATGTCCTCCCGTGAGGCCAAATATCATTCTGAGGGGCCACAGT
         15130       15140       15150       15160       15170       15180

I   T   N   L   L   S   A   I   P   Y   I   G   T   D   L   V   Q   W   I   W
AATTACAAACTTACTATCCGCCATCCCATACATTGGGACAGACCTAGTTCAATGAATCTG
         15190       15200       15210       15220       15230       15240

G   G   Y   S   V   D   S   P   T   L   T   R   F   F   T   F   H   F   I   L
AGGAGGCTACTCAGTAGACAGTCCCACCCTCACACGATTCTTTACCTTTCACTTCATCTT
         15250       15260       15270       15280       15290       15300

P   F   I   I   A   A   L   A   T   L   H   L   L   F   L   H   E   T   G   S
GCCCTTCATTATTGCAGCCCTAGCAACACTCCACCTCCTATTCTTGCACGAAACGGGATC
         15310       15320       15330       15340       15350       15360

N   N   P   L   G   I   T   S   H   S   D   K   I   T   F   H   P   Y   Y   T
AAACAACCCCCTAGGAATCACCTCCCATTCCGATAAAATCACCTTCCACCCTTACTACAC
         15370       15380       15390       15400       15410       15420

I   K   D   A   L   G   L   L   L   F   L   L   S   L   M   T   L   T   L   F
AATCAAAGACGCCCTCGGCTTACTTCTCTTCCTTCTCTCCTTAATGACATTAACACTATT
         15430       15440       15450       15460       15470       15480

S   P   D   L   L   G   D   P   D   N   Y   T   L   A   N   P   L   N   T   P
CTCACCAGACCTCCTAGGCGACCCAGACAATTATACCCTAGCCAACCCCTTAAACACCCC
         15490       15500       15510       15520       15530       15540
```

*Fig. 2Y*

```
           P  H  I  K  P  E  W  Y  F  L  F  A  Y  T  I  L  R  S  V  P
        TCCCCACATCAAGCCCGAATGATATTTCCTATTCGCCTACACAATTCTCCGATCCGTCCC
            15550     15560     15570     15580     15590     15600

N  K  L  G  G  V  L  A  L  L  L  S  I  L  I  L  A  M  I  P
        TAACAAACTAGGAGGCGTCCTTGCCCTATTACTATCCATCCTCATCCTAGCAATAATCCC
            15610     15620     15630     15640     15650     15660

I  L  H  M  S  K  Q  Q  S  M  M  F  R  P  L  S  Q  S  L  Y
        CATCCTCCATATATCCAAACAACAAAGCATAATATTTCGCCCACTAAGCCAATCACTTTA
            15670     15680     15690     15700     15710     15720

W  L  L  A  A  D  L  L  I  L  T  W  I  G  G  Q  P  V  S  Y
        TTGACTCCTAGCCGCAGACCTCCTCATTCTAACCTGAATCGGAGGACAACCAGTAAGCTA
            15730     15740     15750     15760     15770     15780

P  F  T  I  I  G  Q  V  A  S  V  L  Y  F  T  T  I  L  I  L
        CCCTTTTACCATCATTGGACAAGTAGCATCCGTACTATACTTCACAACAATCCTAATCCT
            15790     15800     15810     15820     15830     15840

Thr
           M  P  T  I  S  L  I  E  N  K  M  L  K  W  A   tRNA ——→
        AATACCAACTATCTCCCTAATTGAAAACAAAATACTCAAATGGGCCT|GTCCTTGTAGTAT
            15850     15860     15870     15880     15890     15900
                                                   RNA11 ——→|

AAACTAATACACCAGTCTTGTAAACCGGAGATGAAAACCTTTTTCCAAGGACA|AATCAGA
            15910     15920     15930     15940     15950     15960

Pro
                                                           ←—— tRNA
        GAAAAGTCTTTAACTCCACCATTAGCACCCAAAGCTAAGAT|TCTAATTTAAACTATTCT
            15970     15980     15990     16000     16010     16020

CTG|TTCTTTCATGGGGAAGCAGATTTGGGTACCACCCAAGTATTGACTCACCCATCAACA
            16030     16040     16050     16060     16070     16080

ACCGCTATGTATTTCGTACATTACTGCCAGCCACCATGAATATTGTACGGTACCATAAAT
            16090     16090     16100     16110     16120     16140
```

*Fig. 2Z*

```
ACTTGACCACCTGTAGTACATAAAAACCCAATCCACATCAAAACCCCCTCCCCATGCTTA
    16150     16160     16170     16180     16190     16200

CAAGCAAGTACAGCAATCAACCCTCAACTATCACACATCAACTGCAACTCCAAAGCCACC
    16210     16220     16230     16240     16250     16260

CCTCACCCACTAGGATACCAACAAACCTACCCACCCTTAACAGTACATAGTACATAAAGC
    16270     16280     16290     16300     16310     16320

CATTTACCGTACATAGCACATTACAGTCAAATCCCTTCTCGTCCCCATGGATGACCCCCC
    16330     16340     16350     16360     16370     16380

TCAGATAGGGGTCCCTTGACCACCATCCTCCGTGAAATCAATATCCCGCACAAGAGTGCT
    16390     16400     16410     16420     16430     16440

ACTCTCCTCGCTCCGGGCCCATAACACTTGGGGGTAGCTAAAGTGAACTGTATCCGACAT
    16450     16460     16470     16480     16490     16500

CTGGTTCCTACTTCAGGGTCATAAAGCCTAAATAGCCCACACGTTCCCCTTAAATAAGAC
    16510     16520     16530     16540     16550     16560

ATCACGATG
```

*Fig. 2AA*

```
AGAGAGAGGCATGTGAATTGGGAATTTGGGAAAAATTTTTTGGGGGGAAGGAAAGAAATAGAGGTCAAGAGGTAGAATAG  lambda clone
          | ||  ||            ||    |      ||       ||      | |
CCCACATTAGGCTTAAAAACAGATGCAATTCCCGGACGTCTAAACCAAACCACTTTCACCGCTACACGACCGGGGGTATA  human mtDNA AAGTTGATGAAGAAAAGAAAAAAAGAAGGTAATGAAGGGGGTGCTGGATGTTTCCAACACAAAGAAATGATAAATGTTTG
      |   |   ||||         | ||    | | | ||    | |      | |       ||   |
CTACGGTCAATGCTCTGAAATCTGTGGAGCAAACCACAGTTTCATGCCCATCGTCCTAGAATTAATTCCCCTAAAAATCT Lys
                                                                 ----> tRNA
GGAGGATGGATATTCTAATTAGCCTAATTAGCCTGATTAGCCCTCGCCAGAGTTCACTGTAAAGCTAACCCAGCATTAAC
  || |     || ||| ||||     || |   ||| | ||||  ||||||||||||||||  |||||||||
TTGAAATAGGGCCCGTATTTACCCTATAGCACCCCCTCTACCCCCTCTAGAGCCCACTGTAAAGCTAACTTAGCATTAAC
                                   8295

----> ATPase 8
CTTTTAAGTTAAAGACTAAGAGAATCATTATCTCTTTACAGTGAAATGCCACAGCTAAATACCACTGTATGACCTGCTAT
|||||||||||||||  ||||||||| ||  | ||||||||||||||||||||||  |||||||||| || ||||| || | ||
CTTTTAAGTTAAAGATTAAGAGAACCAACACCTCTTTACAGTGAAATGCCCCAACTAAATACTACCGTATGGCCCACCAT
                                    8366

CATCACCCCAATACTCCTCACGTTATTTCTCATCACCCAACTAAAAATACTAAACACACACTGCCATCTGCCCACCTCAC
  || ||||| ||||||||| ||  |||| |||||||||||||||||||||||||||  |||||||| ||| ||| || || ||||||
AATTACCCCCATACTCCTTACACTATTCCTCATCACCCAACTAAAAATATTAAACACAAACTACCACCTACCTCCCTCAC

----> ATPase 6
CAAAATTTATTAAAAATAAAAAAACTACAGTAAGCCCTGAGAACCAAAATGAACGAAAATTTATTCGCTTCATTCATTACCC
||||    || ||||||||||| || |   || ||||||||||||||||||||||||||||||||| | ||||||||||||||| |||
CAAAGCCCATAAAAATAAAAAAATTATAACAAACCCTGAGAACCAAAATGAACGAAAATCTGTTCGCTTCATTCATTGCCC
                                    8527

CTACAGTACTAGGCCTACCCGCCACAGTACCAATCATCCTATTTCCCCCCTTACTGGTCCCAACCTCCAAATACCTCATC
| ||| | |||||||||||||||| ||||||| |||||||||||||||||||| || ||  |||| |||||||||||||||| ||||||
CCACAATCCTAGGCCTACCCGCCGCAGTACTGATCATTCTATTTCCCCCTCTATTGATCCCCACCTCCAAATATCTCATC
```

*Fig. 3A*

```
AACAACCGACTAATCACCACTCAACAATGACTACTTCAACTCACCTTAAAACAAATAATAACGATACATAACATTAAGGG
|||||||||||||||||||| ||||||||||||| | |||| |||| ||||||||| ||||| ||||| |||| ||| ||
AACAACCGACTAATCACCACCCAACAATGACTAATCAAACTAACCTCAAAACAAATGATAACCATACACAACACTAAAGG

ACGAACCTGGTCCCTTATACTAATTTCCCTGATTATTTTTATTGCCACAACTAATCTCCTCGGACTCTTGCCCCACTCAT
||||||||| || ||||||||| | ||| | || |||||||||||||||||| ||||||||||| |||| |||||||
ACGAACCTGATCTCTTATACTAGTATCCTTAATCATTTTTATTGCCACAACTAACCTCCTCGGACTCCTGCCTCACTCAT

TTACACCAATCACTATACATGTGTCTATTGAAACGTCACTATGTGTGCCCCATGAATATGTACATATTATTATGTGATGT
||||||||| ||| ||       |  ||          |    ||||| |  |
TTACACCAACCACCCAACTATCTATAAACCTAGCCATGGCCATCCCCTTATGAGCGGGCACAGTGATTATAGGCTTTCGC
         8813

ACATGATTATGTACACATTATGT
   |    |    |     |
TCTAAGATTAAAAATGCCCTAGC
```

*Fig. 3B*

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 6744 base pairs
      (B) TYPE: nucleic acid
      (C) STRANDEDNESS: single
      (D) TOPOLOGY: linear (xi) SEQUENCE DESCRIPTION: SEQ ID NO:1:

```
CCTACGGGCT ACTACAACCC TTCGCTGACG CCATAAAACT CTTCACCAAA GAGCCCCTAA      60
AACCCGCCAC ATCTACCATC ACCCTCTACA TCACCGCCCC GACCTTAGCT CTCACCATCG     120
CTCTTCTACT ATGAACCCCC CTCCCCATAC CCAACCCCCT GGTCAACCTC AACCTAGGCC     180
TCCTATTTAT TCTAGCCACC TCTAGCCTAG CCGTTTACTC AATCCTCTGA TCAGGGTGAG     240
CATCAAACTC AAACTACGCC CTGATCGGCG CACTGCGAGC AGTAGCCCAA ACAATCTCAT     300
ATGAAGTCAC CCTAGCCATC ATTCTACTAT CAACATTACT AATAAGTGGC TCCTTTAACC     360
TCTCCACCCT TATCACAACA CAAGAACACC TCTGATTACT CCTGCCATCA TGACCCTTGG     420
CCATAATATG ATTTATCTCC ACACTAGCAG AGACCAACCG AACCCCCTTC GACCTTGCCG     480
AAGGGGAGTC CGAACTAGTC TCAGGCTTCA ACATCGAATA CGCCGCAGGC CCCTTCGCCC     540
TATTCTTCAT AGCCGAATAC ACAAACATTA TTATAATAAA CACCCTCACC ACTACAATCT     600
TCCTAGGAAC AACATATRAC GCACTCTCCC CTGAACTCTA CACAACATAT TTTGTCACCA     660
AGACCCTACT TCTRACCTCC CTGTTCTTAT GAATTCGAAC AGCATACCCC CGATTCCGCT     720
ACGACCAACT CATACACCTC CTATGAAAAA ACTTCCTACC ACTCACCCTA GCATTACTTA     780
TATGATATGT CTCCATACCC ATTACAATCT CCAGCATTCC CCCTCAAACC TAAGAAATAT     840
GTCTGATAAA AGAGTTACTT TGATAGAGTA AATAATAGGA RYTTAAAYCC CCTTATTTCT     900
AGGACTATGA GAATCGAACC CATCCCTGAG AATCCAAAAT TCTCCGTGCC ACCTATCACA     960
CCCCATCCTA AAGTAAGGTC AGCTAAATAA GCTATCGGGC CCATACCCCG AAAATGTTGG    1020
TTATACCCTT CCCGTACTAA TTAATCCCCT GGCCCAACCC GTCATCTACT CTACCATCTT    1080
TGCAGGCACA CTCATCACAG CGCTAAGCTC GCACTGATTT TTTACCTGAG TAGGCCTAGA    1140
AATAAACATG CTAGCTTTTA TTCCAGTTCT AACCAAAAAA ATAAACCCTC GTTCACAGA     1200
AGCTGCCATC AAGTATTTCC TCACGCAAGC AACCGCATCC ATAATCCTTC TAATAGCTAT    1260
CCTCTTCAAC AATATACTCT CCGGACAATG WRMCATWACC AATACYAYCA ATCAATACTC    1320
ATCATTAATA ATCATAATRG CTATAGCAAT AAAAACTAGGA ATAGCCCCCT TTCACTTCTG    1380
AGTCCCAGAG GTTACCCAAG GGCACCCCTC TGACATCCGG CCTGCTYCTT CTCACATGAC    1440
AAAAACTAGC CCCCATCTCA ATCATATACC AAATYTCTCC CTCAYTAAAC GTAAGCCTTC    1500
TCCTCACTCT YTCAATCTTA TCCATCATRG CAGGCAGTTG AGGTGGATTA AACCARACCC    1560
ARCTACGCAA AATCTTAGCA TACTCCTCAA TTACCCACAT AGGATGAATA AYAGCAGTTC    1620
TACCGTACAA CCCTAACATA ACCATTCTTA ATTTAACTAT TTATATTATC CTAACTACTA    1680
CCGCATTCCT ACTACTCAAC TTAAACTCCA GCACCACAAC CCTACTACTA TCTCGCACCT    1740
GAAACAAGCT AACATGACTA ACACCCTTAA TTCCATCCAC CCTCCTCTCC CTAGGAGGCC    1800
TGCCCCCGCT AACCGGCTTT TGCCCAAAT GGGCCATTAT CGAAGAATTC ACAAAAAACA     1860
ATAGCCTCAT CATCCCCACC ATCATAGCCA YCATCACCCT CCTTAACCTC TACTTCTACC    1920
TRCGCCTAAT CTACTCCACC TCAATCACAC TACTCCCYAT ATCTAACAAC GTAAAAATAA    1980
AATGACAGTT TGAACAYACA AAACCCACCC CATTCCTCCC CACACTCATC GCCCTTACCA    2040
CRCTRCTCCT ACCTATCTCC CCTTTTATRC TAATAATCTT ATAGAAATTT AGGTTAAATA    2100
CAGACCAAGA GCCTTCAAAG CCCTCAGTAA GTTGCAATAC TTAATTTCTG YAACAGCTAA    2160
GGACTGCAAA ACCCCACTCT GCATCAACTG NAACGCAAAT CAGCCACTTT AATTAAGCTT    2220
AAGCCCTTAC TAGACCAATG GGAACTTAAA CCCACAAACA CTTAGTTAAC AGCTAAGCAC    2280
```

```
CCTAATCAAC TGGCTTCAAT CTACTTCTCC CGCCGCCGGG AAAAAAGGCG GGAGAAGCCC   2340

CGGCAGGTTT GAAGCTGCTT CTTCGAATTT GCAATTCAAT ATGAAAATCA CCTCRGAGCT   2400

GGTAAAAAGA GGCYTAACCC CTGTCTTTAG ATTTACAGTC AATGCTTCA CTCAGCCATT    2460

TTACCTCACC CCCACKGATG TTCGCCGACC GTTGACTATT CTCTACAAAC CACAAAGACA   2520

TTGGAACACT ATACCTATTA TTCGGCGCAT GAGCTGGAGT CCTAGGCACA GCTCTAAGCC   2580

TCCTTATTCG AGCCGARCTG GGCCAGCCAG GCAACCTTCT AGGTAACGAC CACATCTACA   2640

ACGTTATCGT CACAGCCCAT GCATTTGTAA TAATCTTCTT CATAGTAATA CCCATCATAA   2700

TCGGAGGCTT TGGCAACTGA CTAGTTCCCC TAATAATCGG TGCCCCCGAT ATGGCGTTTC   2760

CCCGCATAAA CAACATAAGC TTMTGACTCT TACCYCCCTC TCTCMTACTC CTGYTYGCAT   2820

CTGCTATAGT GGAGGCCGGM GCAGGAACAG GTTGAACAGT MTACCCTCCC TTRGCAGGGA   2880

ACTACTCCCA CCMTGGAGCC TCCGTAGACS TAACCATCTT STCCTTACAC YTAGCAGGTR   2940

TCTCCTTCTA TCTTAGGGGC CATCAATTTC ATCACAACAA TTATYAATAT AAAACCCCCT   3000

GCCATAACCC AATACCAAAC GCCCCTYTTC GTCTGATCCG TCCTAATCAC AGCAGTCYTA   3060

CTTCTCCTAT CTCTCCCAGT CCTAGCYGCT GGCATCACTA TACTACTAAC AGACCGYAMC   3120

YTCAACACCA CCTTYTTYGA CCCMGCCGGA GGAGGAGACC CCATTCTATA CCAACACCTA   3180

TTCTGATTTT TCGGTCACCC TGAAGTTTAT ATTCTYATCC TACCAGGCTT CGGAATAATC   3240

TCCCATATTG TAACTTACTA CTCCGGAAAA AAGAACCAT TTGGATACAT AGGTATGGTC     3300

TGAGCTATGA TATCAATTGG CTTCCTAGGG TTTATCGTGT GAGCACACCA TATATTTACA   3360

GTAGGAATAG ACGTAGACAC ACGAGCATAT TTCACCTCCG CTACCATAAT CATCGCTATC   3420

CCCACCGGCG TCAAAGTATT TAGCTGACTC GCCACACTCC ACGGAAGCAA TATGAAATGA   3480

TCTGCTGCAG TGCTCTGAGC CCTAGGATTT ATTTTTCTTT TCACCGTAGG TGGCCTGACT   3540

GGCATTGTAT TAGCAAACTC ATCACTAGAC ATCGTACTAC ACGACACGTA CTACGTTGTA   3600

GCCCACTTCC ACTATGTCCT ATCAATAGGA GCTGTATTTG CCATCATAGG AGGCTTCATT   3660

CACTGATTTC CCCTATTCTC AGGGTACACC CTAGACCAAA CCTACGCCAA ATCCATTTC    3720

GCTATCATAT TCATCGGCGT AAATCTAACT TTCTTCCCAC AACACTTTCT CGGCCTATCC   3780

GGAATGCCCC GACGTTACTC GGACTAYCCC GATGCATACA CCACATGAAA YATCCTATCA   3840

TCTGTAGGCT CATTCATTTC TCTAACAGCA GTAATATTAA TAATTTTCAT AATTTGAGAA   3900

GCCTTCGCTT CGAAGCGAAA AGTCCTAATA GTAGAAGAAC CCTCCATAAA CCTGGAGTGA   3960

CTATATGGAT GCCCCCCACC CTACCACACA TTCGAAGAAC CCGTATACAT AAAATCTAGA   4020

CAAAAAAGGA AGGAATCGAA CCCCCCCAAA GCTGGTTTCA AGCCAACCCC ATGGCCTCCA   4080

TGACTTTTTC AAAAAGATAT TAGAAAAACC ATTTCATAAC TTTGTCAAAG TTAAATTATA   4140

GGCTAAATCC TATATATCTT AATGGCACAT GCAGCGCAAG TAGGTCTACA AGACGCTACT   4200

TCCCCTATCA TAGAAGAGCT TATCATCTTT CATGATCACG CCCTCATAAT CATTTTCCTT   4260

ATCTGCTTCC TAGTCCTGTA CGCCCTTTTC CTAACACTCA CAACAAAACT AACTAATACT   4320

AACATCTCAG ACGCTCAGGA AATAGAAACC GTCTGAACTA TCCTGCCCGC CATCATCCTA   4380

GTCCTYATCG CCCTCCCATY CCTACGCATC CTTTACATAA CAGACGAGGT CAACGATCCC   4440

TCCYTTACCA TCAAATCAAT TGGCCAYCAA TGGTACTGAA CCTACGARTA CACCGACTAC   4500

GGCGGACTAA TCTTCAACTC CTACATACTT CCCCCATTAT TCCTAGAACC AGGCGACCTG   4560

CGACTCCTTG ACGTTGACAA TCGAGTAGTA CTCCCGRTTG AAGCCCCCAT TCGTATAATA   4620

ATTACATCAC AAGACGTCTT ACACTCATGA GCTGTCCCCA CATTAGGCTT AAAAACAGAT   4680
```

```
GCAATTCCCG ACGTCTAAA  CCAAACCACT TTCACTGCTA CACGACCAGG GGTATACTAC    4740

GGCCAATGCT CTGAAATCTG TGGAGCAAAC CAGTTTTATG CCCATCGTCC TAGAATTAAT    4800

TCCCCTAAAA ATCTTTGAAA TAGGGCCCGT ATTTACCCTA TAGCACCCCC TCTACCCCCT    4860

CTAGAGCCCA CTGTAAAGCT AACTTAGCAT TAACCTTTTA AGTTAAAGAT TAAGAGAACC    4920

AACACCTCTT TACAGTGAAA TGCCCCAACT AAATACTACC GTATGACCCA CCATAATTAC    4980

CCCCATACTC CTTACACTAT TCCTCATCAC CCAACTAAAA ATATTAAAYA CAAAYTACCA    5040

CCTACCTCCC TCACCAAAGC CCATAAAAAT AAAAAAYTAT AACAAACCCT GAGAACCAAA    5100

ATGAACGAAA ATCTGTTCRC TTCATTCATT GCCCCCACAA TCCTAGGCCT ACCCGCCGCA    5160

GTACTGATCA TTCTATTTCC CCCTCTATTG ATCCCCACCT CCAAATATCT CATCAACAAC    5220

CGACTAATTA CCACCCAACA ATGACTAATC MAACTAACCT CAAAACAAAT GATARCCATA    5280

CACAAACACTA ARGGACGAAC CTGATCTCTT ATACTAGTAT CCTTAATCAT TTTTATTGCC    5340

ACAACTAACC TCCTCGGACT CCTGCCTCAC TCATTTACAC CAACCACCCA ACTATCTATA    5400

AACCTAGCCA TGGCCATCCC CTTATGAGCG GGCRCAGTGA TTATAGGCTT TCGCTCTAAG    5460

ATTAAAAATG CCCTAGCCCA CTTCTTACCA CAAGGCACAC CTACACCCCT TATCCCYATA    5520

CTAGTTATTA TCGAAACCAT CAGSCTAMTC ATTCAACCAA TAGCCCTGGC CGTAMGSCTA    5580

ACCGCTAACA TTACTGCAGG CCACCTAACT CATGMACCTA ATTGGAAGCG CCACMACTAG    5640

CAATATCAAS YATTAACCTT CCCTTCTACA CTTATCATYT TCACAATTCT AATTCTACTG    5700

ACTATCCTAG AAATCGCTGT CGCCTTAATC CAAGCCTACG TTTTYACACT TYTAGTAAGC    5760

CTCTACCTGC ACGACAACAC ATAATGACCC ACCAATCACA TGCCTATCAT ATAGTAAAAC    5820

CCAGCCCATG RCCCCTAACA GGGGCCCTCT CAGCCCTCCT AATGACCTCC GGCCTAGCCA    5880

TGTGATTTCA CTTCCACTCC AYAACSCTCC TYATACTAGG CCTACTAACC AACACACTAA    5940

CCATATACCA ATGATGGCGC GATGCTAACA CGAGTAAAGT CACATACCAA GGCCACCACA    6000

CACCACCTGT CCARAAAGGC CTTCGATACG GGATAATCCT ATTTATTACC TCAGAAGTTT    6060

TTTTCTTCGC AGGATTTTTC TGAGCCTTTT ACCACTCCAG CCTAGCTCCC TACCCCCAA    6120

YTAGGRGGRC ACTGGCCCCS AACAGGCATC ACCCCGCTAA ATCCCCTAGA AGTCCCACTC    6180

CTAAACACAT CCGTATTACT CGCATCAGGR GTATCAATCA CCTGAGCTCA CCATAGTCTA    6240

ATAGAAAAAC AACCGAAACC AAATAATTCA AGCACTGCTT ATTACAATTT TACTGGGTCT    6300

CTATTTACC CTCCTACAAG CCTCAGAGTA CTTCGAGGTT AAAATATTAG ATATTTCCCC    6360

TGATACAGGG CTCAATCTTT TTCTTTTTAA AGCAATATTT CTCAAAGTAC TTTTCACAGA    6420

ACTTAAGTTT CATTAAGCAC TTCACTAAAA GNAAAAGTCT GTGATCTAAT AAATTTGGAA    6480

AATATTGAGA ATTAGAGCCC CCTCTTAGAT ATGTACTGTA GCTACTCAGC TTGTTACAGA    6540

TGGAAGTAAA CATTGTAATA TTCACCCAGC TTTTGAGTGG ATGTCTATTA ACATCACCCA    6600

AATGAGTATT CCATGGAATG CACTTTGCAA AAACCTATTA TTCAAGAAAA ATTCTGGAGC    6660

ATGGAAAGCT ATTAATGGAT AAACCCATTC ACAAAATCAC ACCAAATATC TAAAATCATG    6720

TTTAAAATCT CCTAGAAATG GGTT                                          6744
```

(2) INFORMATION FOR SEQ ID NO:2:

(i) SEQUENCE CHARACTERISTICS:
        (A) LENGTH: 16569 base pairs
        (B) TYPE: nucleic acid
        (C) STRANDEDNESS: single
        (D) TOPOLOGY: linear (xi) SEQUENCE DESCRIPTION: SEQ ID NO:2:

```
GATCACAGGT CTATCACCCT ATTAACCACT CACGGGAGCT CTCCATGCAT TTGGTATTTT      60
CGTCTGGGGG GTATGCACGC GATAGCATTG CGAGACGCTG GAGCCGGAGC ACCCTATGTC     120
GCAGTATCTG TCTTTGATTC CTGCCTCATC CTATTATTTA TCGCACCTAC GTTCAATATT     180
ACAGGCGAAC ATACTTACTA AAGTGTGTTA ATTAATTAAT GCTTGTAGGA CATAATAATA     240
ACAATTGAAT GTCTGCACAG CCACTTTCCA CACAGACATC ATAACAAAAA ATTTCCACCA     300
AACCCCCCCT CCCCCGCTTC TGGCCACAGC ACTTAAACAC ATCTCTGCCA AACCCCAAAA     360
ACAAAGAACC CTAACACCAG CCTAACCAGA TTTCAAATTT TATCTTTTGG CGGTATGCAC     420
TTTTAACAGT CACCCCCCAA CTAACACATT ATTTTCCCCT CCCACTCCCA TACTACTAAT     480
CTCATCAATA CAACCCCCGC CCATCCTACC CAGCACACAC ACACCGCTGC TAACCCCATA     540
CCCCGAACCA ACCAAACCCC AAAGACACCC CCCACAGTTT ATGTAGCTTA CCTCCTCAAA     600
GCAATACACT GAAAATGTTT AGACGGGCTC ACATCACCCC ATAAACAAAT AGGTTTGGTC     660
CTAGCCTTTC TATTAGCTCT TAGTAAGATT ACACATGCAA GCATCCCCGT TCCAGTGAGT     720
TCACCCTCTA AATCACCACG ATCAAAAGGG ACAAGCATCA AGCACGCAGC AATGCAGCTC     780
AAAACGCTTA GCCTAGCCAC ACCCCCACGG GAAACAGCAG TGATTAACCT TTAGCAATAA     840
ACGAAAGTTT AACTAAGCTA TACTAACCCC AGGGTTGGTC AATTTCGTGC CAGCCACCGC     900
GGTCACACGA TTAACCCAAG TCAATAGAAG CCGGCGTAAA GAGTGTTTTA GATCACCCCC     960
TCCCCAATAA AGCTAAAACT CACCTGAGTT GTAAAAAACT CCAGTTGACA CAAAATAGAC    1020
TACGAAAGTG GCTTTAACAT ATCTGAACAC ACAATAGCTA AGACCCAAAC TGGGATTAGA    1080
TACCCCACTA TGCTTAGCCC TAAACCTCAA CAGTTAAATC AACAAAACTG CTCGCCAGAA    1140
CACTACGAGC CACAGCTTAA AACTCAAAGG ACCTGGCGGT GCTTCATATC CCTCTAGAGG    1200
AGCCTGTTCT GTAATCGATA AACCCCGATC AACCTCACCA CCTCTTGCTC AGCCTATATA    1260
CCGCCATCTT CAGCAAACCC TGATGAAGGC TACAAAGTAA GCGCAAGTAC CCACGTAAAG    1320
ACGTTAGGTC AAGGTGTAGC CCATGAGGTG GCAAGAAATG GGCTACATTT TCTACCCCAG    1380
AAAACTACGA TAGCCCTTAT GAAACTTAAG GGTCGAAGGT GGATTTAGCA GTAAACTAAG    1440
AGTAGAGTGC TTAGTTGAAC AGGGCCCTGA AGCGCGTACA CACCGCCCGT CACCCTCCTC    1500
AAGTATACTT CAAAGGACAT TTAACTAAAA CCCCTACGCA TTTATATAGA GGAGACAAGT    1560
CGTAACATGG TAAGTGTACT GGAAAGTGCA CTTGGACGAA CCAGAGTGTA GCTTAACACA    1620
AAGCACCCAA CTTACACTTA GGAGATTTCA ACTTAACTTG ACCGCTCTGA GCTAAACCTA    1680
GCCCCAAACC CACTCCACCT TACTACCAGA CAACCTTAGC CAAACCATTT ACCCAAATAA    1740
AGTATAGGCG ATAGAAATTG AAACCTGGCG CAATAGATAT AGTACCGCAA GGGAAAGATG    1800
AAAAATTATA ACCAAGCATA ATATAGCAAG GACTAACCCC TATACCTTCT GCATAATGAA    1860
TTAACTAGAA ATAACTTTGC AAGGAGAGCC AAAGCTAAGA CCCCCGAAAC CAGACGAGCT    1920
ACCTAAGAAC AGCTAAAAGA GCACACCCGT CTATGTAGCA AAATAGTGGG AAGATTTATA    1980
GGTAGAGGCG ACAAACCTAC CGAGCCTGGT GATAGCTGGT TGTCCAAGAT AGAATCTTAG    2040
TTCAACTTTA AATTTGCCCA CAGAACCCTC TAAATCCCCT TGTAAATTTA ACTGTTAGTC    2100
CAAAGAGGAA CAGCTCTTTG GACACTAGGA AAAACCTTG TAGAGAGAGT AAAAAATTTA    2160
ACACCCATAG TAGGCCTAAA AGCAGCCACC AATTAAGAAA GCGTTCAAGC TCAACACCCA    2220
CTACCTAAAA AATCCCAAAC ATATAACTGA ACTCCTCACA CCCAATTGGA CCAATCTATC    2280
```

-continued

```
ACCCTATAGA AGAACTAATG TTAGTATAAG TAACATGAAA ACATTCTCCT CCGCATAAGC    2340

CTGCGTCAGA TTAAAACACT GAACTGACAA TTAACAGCCC AATATCTACA ATCAACCAAC    2400

AAGTCATTAT TACCCTCACT GTCAACCCAA CACAGGCATG CTCATAAGGA AAGGTTAAAA    2460

AAAGTAAAAG GAACTCGGCA AATCTTACCC CGCCTGTTTA CCAAAAACAT CACCTCTAGC    2520

ATCACCAGTA TTAGAGGCAC CGCCTGCCCA GTGACACATG TTTAACGGCC GCGGTACCCT    2580

AACCGTGCAA AGGTAGCATA ATCACTTGTT CCTTAAATAG GGACCTGTAT GAATGGCTCC    2640

ACGAGGGTTC AGCTGTCTCT TACTTTTAAC CAGTGAAATT GACCTGCCCG TGAAGAGGCG    2700

GGCATAACAC AGCAAGACGA GAAGACCCTA TGGAGCTTTA ATTTATTAAT GCAAACAGTA    2760

CCTAACAAAC CCACAGGTCC TAAACTACCA AACCTGCATT AAAAATTTCG GTTGGGGCGA    2820

CCTCGGAGCA GAACCCAACC TCCGAGCAGT ACATGCTAAG ACTTCACCAG TCAAAGCGAA    2880

CTACTATACT CAATTGATCC AATAACTTGA CCAACGGAAC AAGTTACCCT AGGGATAACA    2940

GCGCAATCCT ATTCTAGAGT CCATATCAAC AATAGGGTTT ACGACCTCGA TGTTGGATCA    3000

GGACATCCCG ATGGTGCAGC CGCTATTAAA GGTTCGTTTG TTCAACGATT AAAGTCCTAC    3060

GTGATCTGAG TTCAGACCGG AGTAATCCAG GTCGGTTTCT ATCTACCTTC AAATTCCTCC    3120

CTGTACGAAA GGACAAGAGA AATAAGGCCT ACTTCACAAA GCGCCTTCCC CCGTAAATGA    3180

TATCATCTCA ACTTAGTATT ATACCCACAC CCACCCAAGA ACAGGGTTTG TTAAGATGGC    3240

AGAGCCCGGT AATCGCATAA AACTTAAAAC TTTACAGTCA GAGGTTCAAT TCCTCTTCTT    3300

AACAACATAC CCATGGCCAA CCTCCTACTC CTCATTGTAC CCATTCTAAT CGCAATGGCA    3360

TTCCTAATGC TTACCGAACG AAAAATTCTA GGCTATATAC AACTACGCAA AGGCCCCAAC    3420

GTTGTAGGCC CCTACGGGCT ACTACAACCC TTCGCTGACG CCATAAAACT CTTCACCAAA    3480

GAGCCCCTAA AACCCGCCAC ATCTACCATC ACCCTCTACA TCACCGCCCC GACCTTAGCT    3540

CTCACCATCG CTCTTCTACT ATGAACCCCC CTCCCCATAC CCAACCCCCT GGTCAACCTC    3600

AACCTAGGCC TCCTATTTAT TCTAGCCACC TCTAGCCTAG CCGTTTACTC AATCCTCTGA    3660

TCAGGGTGAG CATCAAACTC AAACTACGCC CTGATCGGCG CACTGCGAGC AGTAGCCCAA    3720

ACAATCTCAT ATGAAGTCAC CCTAGCCATC ATTCTACTAT CAACATTACT AATAAGTGGC    3780

TCCTTTAACC TCTCCACCCT TATCACAACA CAAGAACACC TCTGATTACT CCTGCCATCA    3840

TGACCCTTGG CCATAATATG ATTTATCTCC ACACTAGCAG AGACCAACCG AACCCCCTTC    3900

GACCTTGCCG AAGGGGAGTC CGAACTAGTC TCAGGCTTCA ACATCGAATA CGCCGCAGGC    3960

CCCTTCGCCC TATTCTTCAT AGCCGAATAC ACAAACATTA TTATAATAAA CACCCTCACC    4020

ACTACAATCT TCCTAGGAAC AACATATGAC GCACTCTCCC CTGAACTCTA CACAACATAT    4080

TTTGTCACCA AGACCCTACT TCTAACCTCC CTGTTCTTAT GAATTCGAAC AGCATACCCC    4140

CGATTCCGCT ACGACCAACT CATACACCTC CTATGAAAAA ACTTCCTACC ACTCACCCTA    4200

GCATTACTTA TATGATATGT CTCCATACCC ATTACAATCT CCAGCATTCC CCTCAAACC    4260

TAAGAAATAT GTCTGATAAA AGAGTTACTT TGATAGAGTA ATAATAGGA GCTTAAACCC    4320

CCTTATTTCT AGGACTATGA GAATCGAACC CATCCCTGAG AATCCAAAAT TCTCCGTGCC    4380

ACCTATCACA CCCCATCCTA AGTAAGGTC AGCTAAATAA GCTATCGGGC CATACCCCG    4440

AAAATGTTGG TTATACCCTT CCCGTACTAA TTAATCCCCT GGCCCAACCC GTCATCTACT    4500

CTACCATCTT TGCAGGCACA CTCATCACAG CGCTAAGCTC GCACTGATTT TTTACCTGAG    4560

TAGGCCTAGA AATAAACATG CTAGCTTTTA TTCCAGTTCT AACCAAAAAA ATAAACCCTC    4620

GTTCCACAGA AGCTGCCATC AAGTATTTCC TCACGCAAGC AACCGCATCC ATAATCCTTC    4680
```

-continued

```
TAATAGCTAT CCTCTTCAAC AATATACTCT CCGGACAATG AACCATAACC AATACTACCA    4740
ATCAATACTC ATCATTAATA ATCATAATAG CTATAGCAAT AAAACTAGGA ATAGCCCCCT    4800
TTCACTTCTG AGTCCCAGAG GTTACCCAAG GCACCCCTCT GACATCCGGC CTGCTTCTTC    4860
TCACATGACA AAAACTAGCC CCCATCTCAA TCATATACCA AATCTCTCCC TCACTAAACG    4920
TAAGCCTTCT CCTCACTCTC TCAATCTTAT CCATCATAGC AGGCAGTTGA GGTGGATTAA    4980
ACCAGACCCA GCTACGCAAA ATCTTAGCAT ACTCCTCAAT TACCCACATA GGATGAATAA    5040
TAGCAGTTCT ACCGTACAAC CCTAACATAA CCATTCTTAA TTTAACTATT TATATTATCC    5100
TAACTACTAC CGCATTCCTA CTACTCAACT TAAACTCCAG CACCACGACC CTACTACTAT    5160
CTCGCACCTG AAACAAGCTA ACATGACTAA CACCCTTAAT TCCATCCACC CTCCTCTCCC    5220
TAGGAGGCCT GCCCCCGCTA ACCGGCTTTT TGCCCAAATG GGCCATTATC GAAGAATTCA    5280
CAAAAAACAA TAGCCTCATC ATCCCCACCA TCATAGCCAC CATCACCCTC CTTAACCTCT    5340
ACTTCTACCT ACGCCTAATC TACTCCACCT CAATCACACT ACTCCCCATA TCTAACAACG    5400
TAAAAATAAA ATGACAGTTT GAACATACAA AACCCACCCC ATTCCTCCCC ACACTCATCG    5460
CCCTTACCAC GCTACTCCTA CCTATCTCCC CTTTTATACT AATAATCTTA TAGAAATTTA    5520
GGTTAAATAC AGACCAAGAG CCTTCAAAGC CCTCAGTAAG TTGCAATACT TAATTTCTGT    5580
AACAGCTAAG GACTGCAAAA CCCCACTCTG CATCAACTGA ACGCAAATCA GCCACTTTAA    5640
TTAAGCTAAG CCCTTACTAG ACCAATGGGA CTTAAACCCA CAAACACTTA GTTAACAGCT    5700
AAGCACCCTA ATCAACTGGC TTCAATCTAC TTCTCCCGCC GCCGGGAAAA AAGGCGGGAG    5760
AAGCCCCGGC AGGTTTGAAG CTGCTTCTTC GAATTTGCAA TTCAATATGA AAATCACCTC    5820
GGAGCTGGTA AAAAGAGGCC TAACCCCTGT CTTTAGATTT ACAGTCCAAT GCTTCACTCA    5880
GCCATTTTAC CTCACCCCCA CTGATGTTCG CCGACCGTTG ACTATTCTCT ACAAACCACA    5940
AAGACATTGG AACACTATAC CTATTATTCG GCGCATGAGC TGGAGTCCTA GGCACAGCTC    6000
TAAGCCTCCT TATTCGAGCC GAGCTGGGCC AGCCAGGCAA CCTTCTAGGT AACGACCACA    6060
TCTACAACGT TATCGTCACA GCCCATGCAT TTGTAATAAT CTTCTTCATA GTAATACCCA    6120
TCATAATCGG AGGCTTTGGC AACTGACTAG TTCCCCTAAT AATCGGTGCC CCCGATATGG    6180
CGTTTCCCCG CATAAACAAC ATAAGCTTCT GACTCTTACC TCCCTCTCTC CTACTCCTGC    6240
TCGCATCTGC TATAGTGGAG GCCGGAGCAG GAACAGGTTG AACAGTCTAC CCTCCCTTAG    6300
CAGGGAACTA CTCCCACCCT GGAGCCTCCG TAGACCTAAC CATCTTCTCC TTACACCTAG    6360
CAGGTGTCTC CTCTATCTTA GGGGCCATCA ATTTCATCAC AACAATTATC AATATAAAAC    6420
CCCCTGCCAT AACCCAATAC CAAACGCCCC TCTTCGTCTG ATCCGTCCTA ATCACAGCAG    6480
TCCTACTTCT CCTATCTCTC CCAGTCCTAG CTGCTGGCAT CACTATACTA CTAACAGACC    6540
GCAACCTCAA CACCACCTTC TTCGACCCCG CCGGAGGAGG AGACCCCATT CTATACCAAC    6600
ACCTATTCTG ATTTTTCGGT CACCCTGAAG TTTATATTCT TATCCTACCA GGCTTCGGAA    6660
TAATCTCCCA TATTGTAACT TACTACTCCG GAAAAAAAGA ACCATTTGGA TACATAGGTA    6720
TGGTCTGAGC TATGATATCA ATTGGCTTCC TAGGGTTTAT CGTGTGAGCA CACCATATAT    6780
TTACAGTAGG AATAGACGTA GACACACGAG CATATTTCAC CTCCGCTACC ATAATCATCG    6840
CTATCCCCAC CGGCGTCAAA GTATTTAGCT GACTCGCCAC ACTCCACGGA AGCAATATGA    6900
AATGATCTGC TGCAGTGCTC TGAGCCCTAG GATTCATCTT TCTTTTCACC GTAGGTGGCC    6960
TGACTGGCAT TGTATTAGCA AACTCATCAC TAGACATCGT ACTACACGAC ACGTACTACG    7020
```

```
TTGTAGCCCA CTTCCACTAT GTCCTATCAA TAGGAGCTGT ATTTGCCATC ATAGGAGGCT    7080

TCATTCACTG ATTTCCCCTA TTCTCAGGCT ACACCCTAGA CCAAACCTAC GCCAAAATCC    7140

ATTTCACTAT CATATTCATC GGCGTAAATC TAACTTTCTT CCCACAACAC TTTCTCGGCC    7200

TATCCGGAAT GCCCCGACGT TACTCGGACT ACCCCGATGC ATACACCACA TGAAACATCC    7260

TATCATCTGT AGGCTCATTC ATTTCTCTAA CAGCAGTAAT ATTAATAATT TTCATGATTT    7320

GAGAAGCCTT CGCTTCGAAG CGAAAAGTCC TAATAGTAGA AGAACCCTCC ATAAACCTGG    7380

AGTGACTATA TGGATGCCCC CCACCCTACC ACACATTCGA AGAACCCGTA TACATAAAAT    7440

CTAGACAAAA AAGGAAGGAA TCGAACCCCC CAAAGCTGGT TTCAAGCCAA CCCCATGGCC    7500

TCCATGACTT TTTCAAAAAG GTATTAGAAA ACCATTTCA TAACTTTGTC AAAGTTAAAT     7560

TATAGGCTAA ATCCTATATA TCTTAATGGC ACATGCAGCG CAAGTAGGTC TACAAGACGC    7620

TACTTCCCCT ATCATAGAAG AGCTTATCAC CTTTCATGAT CACGCCCTCA TAATCATTTT    7680

CCTTATCTGC TTCCTAGTCC TGTATGCCCT TTTCCTAACA CTCACAACAA AACTAACTAA    7740

TACTAACATC TCAGACGCTC AGGAAATAGA AACCGTCTGA ACTATCCTGC CCGCCATCAT    7800

CCTAGTCCTC ATCGCCCTCC CATCCCTACG CATCCTTTAC ATAACAGACG AGGTCAACGA    7860

TCCCTCCCTT ACCATCAAAT CAATTGGCCA CCAATGGTAC TGAACCTACG AGTACACCGA    7920

CTACGGCGGA CTAATCTTCA ACTCCTACAT ACTTCCCCCA TTATTCCTAG AACCAGGCGA    7980

CCTGCGACTC CTTGACGTTG ACAATCGAGT AGTACTCCCG ATTGAAGCCC CCATTCGTAT    8040

AATAATTACA TCACAAGACG TCTTGCACTC ATGAGCTGTC CCCACATTAG GCTTAAAAAC    8100

AGATGCAATT CCCGGACGTC TAAACCAAAC CACTTTCACC GCTACACGAC CGGGGGTATA    8160

CTACGGTCAA TGCTCTGAAA TCTGTGGAGC AAACCACAGT TTCATGCCCA TCGTCCTAGA    8220

ATTAATTCCC CTAAAAATCT TTGAAATAGG GCCCGTATTT ACCCTATAGC ACCCCCTCTA    8280

CCCCCTCTAG AGCCCACTGT AAAGCTAACT TAGCATTAAC CTTTTAAGTT AAAGATTAAG    8340

AGAACCAACA CCTCTTTACA GTGAAATGCC CCAACTAAAT ACTACCGTAT GGCCCACCAT    8400

AATTACCCCC ATACTCCTTA CACTATTCCT CATCACCCAA CTAAAAATAT TAAACACAAA    8460

CTACCACCTA CCTCCCTCAC CAAAGCCCAT AAAAATAAAA AATTATAACA AACCCTGAGA    8520

ACCAAAATGA ACGAAAATCT GTTCGCTTCA TTCATTGCCC CCACAATCCT AGGCCTACCC    8580

GCCGCAGTAC TGATCATTCT ATTTCCCCCT CTATTGATCC CCACCTCCAA ATATCTCATC    8640

AACAACCGAC TAATCACCAC CCAACAATGA CTAATCAAAC TAACCTCAAA ACAAATGATA    8700

ACCATACACA ACACTAAAGG ACGAACCTGA TCTCTTATAC TAGTATCCTT AATCATTTTT    8760

ATTGCCACAA CTAACCTCCT CGGACTCCTG CCTCACTCAT TTACACCAAC CACCCAACTA    8820

TCTATAAACC TAGCCATGGC CATCCCCTTA TGAGCGGGCA CAGTGATTAT AGGCTTTCGC    8880

TCTAAGATTA AAAATGCCCT AGCCCACTTC TTACCACAAG GCACACCTAC ACCCCTTATC    8940

CCCATACTAG TTATTATCGA AACCATCAGC CTACTCATTC AACCAATAGC CCTGGCCGTA    9000

CGCCTAACCG CTAACATTAC TGCAGGCCAC CTACTCATGC ACCTAATTGG AAGCGCCACC    9060

CTAGCAATAT CAACCATTAA CCTTCCCTCT ACACTTATCA TCTTCACAAT TCTAATTCTA    9120

CTGACTATCC TAGAAATCGC TGTCGCCTTA ATCCAAGCCT ACGTTTTCAC ACTTCTAGTA    9180

AGCCTCTACC TGCACGACAA CACATAATGA CCCACCAATC ACATGCCTAT CATATAGTAA    9240

AACCCAGCCC ATGACCCCTA ACAGGGGCCC TCTCAGCCCT CCTAATGACC TCCGGCCTAG    9300

CCATGTGATT TCACTTCCAC TCCATAACGC TCCTCATACT AGGCCTACTA ACCAACACAC    9360

TAACCATATA CCAATGATGG CGCGATGTAA CACGAGAAAG CACATACCAA GGCCACCACA    9420
```

```
CACCACCTGT CCAAAAAGGC CTTCGATACG GGATAATCCT ATTTATTACC TCAGAAGTTT    9480

TTTTCTTCGC AGGATTTTTC TGAGCCTTTT ACCACTCCAG CCTAGCCCCT ACCCCCCAAT    9540

TAGGAGGGCA CTGGCCCCCA ACAGGCATCA CCCCGCTAAA TCCCCTAGAA GTCCCACTCC    9600

TAAACACATC CGTATTACTC GCATCAGGAG TATCAATCAC CTGAGCTCAC CATAGTCTAA    9660

TAGAAAACAA CCGAAACCAA ATAATTCAAG CACTGCTTAT TACAATTTTA CTGGGTCTCT    9720

ATTTTACCCT CCTACAAGCC TCAGAGTACT TCGAGTCTCC CTTCACCATT TCCGACGGCA    9780

TCTACGGCTC AACATTTTTT GTAGCCACAG GCTTCCACGG ACTTCACGTC ATTATTGGCT    9840

CAACTTTCCT CACTATCTGC TTCATCCGCC AACTAATATT TCACTTTACA TCCAAACATC    9900

ACTTTGGCTT CGAAGCCGCC GCCTGATACT GGCATTTTGT AGATGTGGTT TGACTATTTC    9960

TGTATGTCTC CATCTATTGA TGAGGGTCTT ACTCTTTTAG TATAAATAGT ACCGTTAACT    10020

TCCAATTAAC TAGTTTTGAC AACATTCAAA AAGAGTAAT AAACTTCGCC TTAATTTAA    10080

TAATCAACAC CCTCCTAGCC TTACTACTAA TAATTATTAC ATTTTGACTA CCACAACTCA    10140

ACGGCTACAT AGAAAAATCC ACCCCTTACG AGTGCGGCTT CGACCCTATA TCCCCCGCCC    10200

GCGTCCCTTT CTCCATAAAA TTCTTCTTAG TAGCTATTAC CTTCTTATTA TTTGATCTAG    10260

AAATTGCCCT CCTTTTACCC CTACCATGAG CCCTACAAAC AACTAACCTG CCACTAATAG    10320

TTATGTCATC CCTCTTATTA ATCATCATCC TAGCCCTAAG TCTGGCCTAT GAGTGACTAC    10380

AAAAAGGATT AGACTGAACC GAATTGGTAT ATAGTTTAAA CAAAACGAAT GATTTCGACT    10440

CATTAAATTA TGATAATCAT ATTTACCAAA TGCCCCTCAT TTACATAAAT ATTATACTAG    10500

CATTTACCAT CTCACTTCTA GGAATACTAG TATATCGCTC ACACCTCATA TCCTCCCTAC    10560

TATGCCTAGA AGGAATAATA CTATCGCTGT TCATTATAGC TACTCTCATA ACCCTCAACA    10620

CCCACTCCCT CTTAGCCAAT ATTGTGCCTA TTGCCATACT AGTCTTTGCC GCCTGCGAAG    10680

CAGCGGTGGG CCTAGCCCTA CTAGTCTCAA TCTCCAACAC ATATGGCCTA GACTACGTAC    10740

ATAACCTAAA CCTACTCCAA TGCTAAAACT AATCGTCCCA ACAATTATAT TACTACCACT    10800

GACATGACTT TCCAAAAAAC ACATAATTTG AATCAACACA ACCACCCACA GCCTAATTAT    10860

TAGCATCATC CCTCTACTAT TTTTTAACCA AATCAACAAC AACCTATTTA GCTGTTCCCC    10920

AACCTTTTCC TCCGACCCCC TAACAACCCC CCTCCTAATA CTAACTACCT GACTCCTACC    10980

CCTCACAATC ATGGCAAGCC AACGCCACTT ATCCAGTGAA CCACTATCAC GAAAAAAACT    11040

CTACCTCTCT ATACTAATCT CCCTACAAAT CTCCTTAATT ATAACATTCA CAGCCACAGA    11100

ACTAATCATA TTTTATATCT TCTTCGAAAC CACACTTATC CCCACCTTGG CTATCATCAC    11160

CCGATGAGGC AACCAGCCAG AACGCCTGAA CGCAGGCACA TACTTCCTAT TCTACACCCT    11220

AGTAGGCTCC CTTCCCCTAC TCATCGCACT AATTTACACT CACAACACCC TAGGCTCACT    11280

AAACATTCTA CTACTCACTC TCACTGCCCA AGAACTATCA AACTCCTGAG CCAATAACTT    11340

AATATGACTA GCTTACACAA TAGCTTTTAT AGTAAAGATA CCTCTTTACG GACTCCACTT    11400

ATGACTCCCT AAAGCCCATG TCGAAGCCCC CATCGCTGGG TCAATAGTAC TTGCCGCAGT    11460

ACTCTTAAAA CTAGGCGGCT ATGGTATAAT ACGCCTCACA CTCATTCTCA ACCCCCTGAC    11520

AAAACACATA GCCTACCCCT TCCTTGTACT ATCCCTATGA GGCATAATTA TAACAAGCTC    11580

CATCTGCCTA CGACAAACAG ACCTAAAATC GCTCATTGCA TACTCTTCAA TCAGCCACAT    11640

AGCCCTCGTA GTAACAGCCA TTCTCATCCA AACCCCCTGA AGCTTCACCG GCGCAGTCAT    11700

TCTCATAATC GCCCACGGGC TTACATCCTC ATTACTATTC TGCCTAGCAA ACTCAAACTA    11760
```

```
                                    -continued
CGAACGCACT CACAGTCGCA TCATAATCCT CTCTCAAGGA CTTCAAACTC TACTCCCACT    11820

AATAGCTTTT TGATGACTTC TAGCAAGCCT CGCTAACCTC GCCTTACCCC CCACTATTAA    11880

CCTACTGGGA GAACTCTCTG TGCTAGTAAC CACGTTCTCC TGATCAAATA TCACTCTCCT    11940

ACTTACAGGA CTCAACATAC TAGTCACAGC CCTATACTCC CTCTACATAT TTACCACAAC    12000

ACAATGGGGC TCACTCACCC ACCACATTAA CAACATAAAA CCCTCATTCA CACGAGAAAA    12060

CACCCTCATG TTCATACACC TATCCCCCAT TCTCCTCCTA TCCCTCAACC CCGACATCAT    12120

TACCGGGTTT TCCTCTTGTA ATATAGTTT AACCAAAACA TCAGATTGTG AATCTGACAA     12180

CAGAGGCTTA CGACCCCTTA TTTACCGAGA AAGCTCACAA GAACTGCTAA CTCATGCCCC    12240

CATGTCTAAC AACATGGCTT TCTCAACTTT TAAAGGATAA CAGCTATCCA TTGGTCTTAG    12300

GCCCCAAAAA TTTTGGTGCA ACTCCAAATA AAAGTAATAA CCATGCACAC TACTATAACC    12360

ACCCTAACCC TGACTTCCCT AATTCCCCCC ATCCTTACCA CCCTCGTTAA CCCTAACAAA    12420

AAAAACTCAT ACCCCCATTA TGTAAAATCC ATTGTCGCAT CCACCTTTAT TATCAGTCTC    12480

TTCCCCACAA CAATATTCAT GTGCCTAGAC CAAGAAGTTA TTATCTCGAA CTGACACTGA    12540

GCCACAACCC AAACAACCCA GCTCTCCCTA AGCTTCAAAC TAGACTACTT CTCCATAATA    12600

TTCATCCCTG TAGCATTGTT CGTTACATGG TCCATCATAG AATTCTCACT GTGATATATA    12660

AACTCAGACC CAAACATTAA TCAGTTCTTC AAATATCTAC TCATCTTCCT AATTACCATA    12720

CTAATCTTAG TTACCGCTAA CAACCTATTC CAACTGTTCA TCGGCTGAGA GGGCGTAGGA    12780

ATTATATCCT TCTTGCTCAT CAGTTGATGA TACGCCCGAG CAGATGCCAA CACAGCAGCC    12840

ATTCAAGCAA TCCTATACAA CCGTATCGGC GATATCGGTT TCATCCTCGC CTTAGCATGA    12900

TTTATCCTAC ACTCCAACTC ATGAGACCCA CAACAAATAG CCCTTCTAAA CGCTAATCCA    12960

AGCCTCACCC CACTACTAGG CCTCCTCCTA GCAGCAGCAG GCAAATCAGC CCAATTAGGT    13020

CTCCACCCCT GACTCCCCTC AGCCATAGAA GGCCCCACCC CAGTCTCAGC CCTACTCCAC    13080

TCAAGCACTA TAGTTGTAGC AGGAATCTTC TTACTCATCC GCTTCCACCC CCTAGCAGAA    13140

AATAGCCCAC TAATCCAAAC TCTAACACTA TGCTTAGGCG CTATCACCAC TCTGTTCGCA    13200

GCAGTCTGCG CCCTTACACA AAATGACATC AAAAAAATCG TAGCCTTCTC CACTTCAAGT    13260

CAACTAGGAC TCATAATAGT TACAATCGGC ATCAACCAAC CACACCTAGC ATTCCTGCAC    13320

ATCTGTACCC ACGCCTTCTT CAAAGCCATA CTATTTATGT GCTCCGGGTC CATCATCCAC    13380

AACCTTAACA ATGAACAAGA TATTCGAAAA ATAGGAGGAC TACTCAAAAC CATACCTCTC    13440

ACTTCAACCT CCCTCACCAT TGGCAGCCTA GCATTAGCAG GAATACCTTT CCTCACAGGT    13500

TTCTACTCCA AAGACCACAT CATCGAAACC GCAAACATAT CATACACAAA CGCCTGAGCC    13560

CTATCTATTA CTCTCATCGC TACCTCCCTG ACAAGCGCCT ATAGCACTCG AATAATTCTT    13620

CTCACCCTAA CAGGTCAACC TCGCTTCCCC ACCCTTACTA ACATTAACGA AAATAACCCC    13680

ACCCTACTAA ACCCCATTAA ACGCCTGGCA GCCGGAAGCC TATTCGCAGG ATTTCTCATT    13740

ACTAACAACA TTTCCCCCGC ATCCCCCTTC CAAACAACAA TCCCCCTCTA CCTAAAACTC    13800

ACAGCCCTCG CTGTCACTTT CCTAGGACTT CTAACAGCCC TAGACCTCAA CTACCTAACC    13860

AACAAACTTA AAATAAAATC CCCACTATGC ACATTTTATT TCTCCAACAT ACTCGGATTC    13920

TACCCTAGCA TCACACACCG CACAATCCCC TATCTAGGCC TTCTTACGAG CCAAAACCTG    13980

CCCCTACTCC TCCTAGACCT AACCTGACTA GAAAAGCTAT TACCTAAAAC AATTTCACAG    14040

CACCAAATCT CCACCTCCAT CATCACCTCA ACCCAAAAAG GCATAATTAA ACTTTACTTC    14100

CTCTCTTTCT TCTTCCCACT CATCCTAACC CTACTCCTAA TCACATAACC TATTCCCCCG    14160
```

-continued

```
AGCAATCTCA ATTACAATAT ATACACCAAC AAACAATGTT CAACCAGTAA CTACTACTAA  14220

TCAACGCCCA TAATCATACA AAGCCCCCGC ACCAATAGGA TCCTCCCGAA TCAACCCTGA  14280

CCCCTCTCCT TCATAAATTA TTCAGCTTCC TACACTATTA AAGTTTACCA CAACCACCAC  14340

CCCATCATAC TCTTTCACCC ACAGCACCAA TCCTACCTCC ATCGCTAACC CCACTAAAAC  14400

ACTCACCAAG ACCTCAACCC CTGACCCCCA TGCCTCAGGA TACTCCTCAA TAGCCATCGC  14460

TGTAGTATAT CCAAAGACAA CCATCATTCC CCCTAAATAA ATTAAAAAAA CTATTAAACC  14520

CATATAACCT CCCCCAAAAT TCAGAATAAT AACACACCCG ACCACACCGC TAACAATCAA  14580

TACTAAACCC CCATAAATAG GAGAAGGCTT AGAAGAAAAC CCCACAAACC CCATTACTAA  14640

ACCCACACTC AACAGAAACA AAGCATACAT CATTATTCTC GCACGGACTA CAACCACGAC  14700

CAATGATATG AAAAACCATC GTTGTATTTC AACTACAAGA ACACCAATGA CCCCAATACG  14760

CAAAATTAAC CCCCTAATAA AATTAATTAA CCACTCATTC ATCGACCTCC CCACCCCATC  14820

CAACATCTCC GCATGATGAA ACTTCGGCTC ACTCCTTGGC GCCTGCCTGA TCCTCCAAAT  14880

CACCACAGGA CTATTCCTAG CCATGCACTA CTCACCAGAC GCCTCAACCG CCTTTTCATC  14940

AATCGCCCAC ATCACTCGAG ACGTAAATTA TGGCTGAATC ATCCGCTACC TTCACGCCAA  15000

TGGCGCCTCA ATATTCTTTA TCTGCCTCTT CCTACACATC GGGCGAGGCC TATATTACGG  15060

ATCATTTCTC TACTCAGAAA CCTGAAACAT CGGCATTATC CTCCTGCTTG CAACTATAGC  15120

AACAGCCTTC ATAGGCTATG TCCTCCCGTG AGGCCAAATA TCATTCTGAG GGGCCACAGT  15180

AATTACAAAC TTACTATCCG CCATCCCATA CATTGGGACA GACCTAGTTC AATGAATCTG  15240

AGGAGGCTAC TCAGTAGACA GTCCCACCCT CACACGATTC TTTACCTTTC ACTTCATCTT  15300

GCCCTTCATT ATTGCAGCCC TAGCAACACT CCACCTCCTA TTCTTGCACG AAACGGGATC  15360

AAACAACCCC CTAGGAATCA CCTCCCATTC CGATAAAATC ACCTTCCACC CTTACTACAC  15420

AATCAAAGAC GCCCTCGGCT TACTTCTCTT CCTTCTCTCC TTAATGACAT AACACTATT  15480

CTCACCAGAC CTCCTAGGCG ACCCAGACAA TTATACCCTA GCCAACCCCT TAAACACCCC  15540

TCCCCACATC AAGCCCGAAT GATATTTCCT ATTCGCCTAC ACAATTCTCC GATCCGTCCC  15600

TAACAAACTA GGAGGCGTCC TTGCCCTATT ACTATCCATC CTCATCCTAG CAATAATCCC  15660

CATCCTCCAT ATATCCAAAC AACAAAGCAT AATATTTCGC CCACTAAGCC AATCACTTTA  15720

TTGACTCCTA GCCGCAGACC TCCTCATTCT AACCTGAATC GGAGGACAAC CAGTAAGCTA  15780

CCCTTTTACC ATCATTGGAC AAGTAGCATC CGTACTATAC TTCACAACAA TCCTAATCCT  15840

AATACCAACT ATCTCCCTAA TTGAAAACAA AATACTCAAA TGGGCCTGTC CTTGTAGTAT  15900

AAACTAATAC ACCAGTCTTG TAAACCGGAG ATGAAAACCT TTTTCCAAGG ACAAATCAGA  15960

GAAAAGTCT TTAACTCCAC CATTAGCACC CAAAGCTAAG ATTCTAATTT AAACTATTCT  16020

CTGTTCTTTC ATGGGGAAGC AGATTTGGGT ACCACCCAAG TATTGACTCA CCCATCAACA  16080

ACCGCTATGT ATTTCGTACA TTACTGCCAG CCACCATGAA TATTGTACGG TACCATAAAT  16140

ACTTGACCAC CTGTAGTACA TAAAAACCCA ATCCACATCA AAACCCCTC CCCATGCTTA  16200

CAAGCAAGTA CAGCAATCAA CCCTCAACTA TCACACATCA ACTGCAACTC CAAAGCCACC  16260

CCTCACCCAC TAGGATACCA ACAAACCTAC CCACCCTTAA CAGTACATAG TACATAAAGC  16320

CATTTACCGT ACATAGCACA TTACAGTCAA ATCCCTTCTC GTCCCCATGG ATGACCCCCC  16380

TCAGATAGGG GTCCCTTGAC CACCATCCTC CGTGAAATCA ATATCCCGCA CAAGAGTGCT  16440

ACTCTCCTCG CTCCGGGCCC ATAACACTTG GGGGTAGCTA AAGTGAACTG TATCCGACAT  16500
```

| CTGGTTCCTA CTTCAGGGTC ATAAAGCCTA AATAGCCCAC ACGTTCCCCT TAAATAAGAC | 16560 |

| ATCACGATG | 16569 |

(2) INFORMATION FOR SEQ ID NO:3:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (xi) SEQUENCE DESCRIPTION: SEQ ID NO:3:

| AGAGAGAGGC ATGTGAATTG GGAATTTGGG AAAAATTTTT TGGGGGGAAG GAAAGAAATA | 60 |
| AGGTCAAGA GGTAGAATAG AAGTTGATGA AGAAAAGAAA AAAAGAAGGT AATGAAGGGG | 120 |
| GTGCTGGATG TTTCCAACAC AAAGAAATGA TAAATGTTTG GGAGGATGGA TATTCTAATT | 180 |
| AGCCTAATTA GCCTGATTAG CCCTCGCCAG AGTTCACTGT AAAGCTAACC CAGCATTAAC | 240 |
| CTTTTAAGTT AAAGACTAAG AGAATCATTA TCTCTTTACA GTGAAATGCC ACAGCTAAAT | 300 |
| ACCACTGTAT GACCTGCTAT CATCACCCCA ATACTCCTCA CGTTATTTCT CATCACCCAA | 360 |
| CTAAAAATAC TAAACACACA CTGCCATCTG CCCACCTCAC CAAAATTTAT TAAAATAAAA | 420 |
| AACTACAGTA AGCCCTGAGA ACCAAAATGA ACGAAAATTT ATTCGCTTCA TTCATTACCC | 480 |
| CTACAGTACT AGGCCTACCC GCCACAGTAC CAATCATCCT ATTTCCCCCC TTACTGGTCC | 540 |
| CAACCTCCAA ATACCTCATC AACAACCGAC TAATCACCAC TCAACAATGA CTACTTCAAC | 600 |
| TCACCTTAAA ACAAATAATA ACGATACATA ACATTAAGGG ACGAACCTGG TCCCTTATAC | 660 |
| TAATTTCCCT GATTATTTTT ATTGCCACAA CTAATCTCCT CGGACTCTTG CCCCACTCAT | 720 |
| TTACACCAAT CACTATACAT GTGTCTATTG AAACGTCACT ATGTGTGCCC CATGAATATG | 780 |
| TACATATTAT TATGTGATGT ACATGATTAT GTACACATTA TGT | 823 |

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:4:

| CCTTACACCT AGCAGGTA | 18 |

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:5:

| ACGCCGATGA ATATGATAGC | 20 |

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:6:

CATGCAGCGC AAGTAGGTCT ACAAGAC                                              27

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:7:

TGTTATGTAA AGGATGCGTA GGGATGG                                              27

(2) INFORMATION FOR SEQ ID NO:8:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:8:

TATGAGGGCG TGATCATGAA AG                                                   22

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:9:

GGCACGGCTG TCCAAGG                                                         17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:10:

CCCGGCCTGG TACACTG                                                         17

(2) INFORMATION FOR SEQ ID NO:11:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:11:

GCGGACATGG AGGACGTG                                                        18

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

CGATGCCGAT GACCTGCAGA AG        22

(2) INFORMATION FOR SEQ ID NO:13:

(i) SEQUENCE CHARACTERISTICS:
        (A) LENGTH: 318 amino acids
        (B) TYPE: amino acid
        (C) STRANDEDNESS:
        (D) TOPOLOGY: linear (xi) SEQUENCE DESCRIPTION: SEQ ID NO:13:

```
Met Pro Met Ala Asn Leu Leu Leu Ile Val Pro Ile Leu Ile Ala
1               5                   10                  15

Met Ala Phe Leu Met Leu Thr Glu Arg Lys Ile Leu Gly Tyr Met Gln
            20                  25                  30

Leu Arg Lys Gly Pro Asn Val Val Gly Pro Tyr Gly Leu Leu Gln Pro
            35                  40                  45

Phe Ala Asp Ala Met Lys Leu Phe Thr Lys Glu Pro Leu Lys Pro Ala
        50                  55                  60

Thr Ser Thr Ile Thr Leu Tyr Ile Thr Ala Pro Thr Leu Ala Leu Thr
65                  70                  75                  80

Ile Ala Leu Leu Leu Trp Thr Pro Leu Pro Met Pro Asn Pro Leu Val
                85                  90                  95

Asn Leu Asn Leu Gly Leu Leu Phe Ile Leu Ala Thr Ser Ser Leu Ala
                100                 105                 110

Val Tyr Ser Ile Leu Trp Ser Gly Trp Ala Ser Asn Ser Asn Tyr Ala
            115                 120                 125

Leu Ile Gly Ala Leu Arg Ala Val Ala Gln Thr Ile Ser Tyr Glu Val
130                 135                 140

Thr Leu Ala Ile Ile Leu Leu Ser Thr Leu Leu Met Ser Gly Ser Phe
145                 150                 155                 160

Asn Leu Ser Thr Leu Ile Thr Thr Gln Glu His Leu Trp Leu Leu Leu
                165                 170                 175

Pro Ser Trp Pro Leu Ala Met Met Trp Phe Ile Ser Thr Leu Ala Glu
                180                 185                 190

Thr Asn Arg Thr Pro Phe Asp Leu Ala Glu Gly Glu Ser Glu Leu Val
            195                 200                 205

Ser Gly Phe Asn Ile Glu Tyr Ala Ala Gly Pro Phe Ala Leu Phe Phe
210                 215                 220

Met Ala Glu Tyr Thr Asn Ile Ile Met Met Asn Thr Leu Thr Thr Thr
225                 230                 235                 240

Ile Phe Leu Gly Thr Thr Tyr Asp Ala Leu Ser Pro Glu Leu Tyr Thr
                245                 250                 255

Thr Tyr Phe Val Thr Lys Thr Leu Leu Leu Thr Ser Leu Phe Leu Trp
            260                 265                 270

Ile Arg Thr Ala Tyr Pro Arg Phe Arg Tyr Asp Gln Leu Met His Leu
            275                 280                 285

Leu Trp Lys Asn Phe Leu Pro Leu Thr Leu Ala Leu Leu Met Trp Tyr
            290                 295                 300

Val Ser Met Pro Ile Thr Ile Ser Ser Ile Pro Pro Gln Thr
305                 310                 315
```

(2) INFORMATION FOR SEQ ID NO:14:

(i) SEQUENCE CHARACTERISTICS:
        (A) LENGTH: 347 amino acids
        (B) TYPE: amino acid (C) STRANDEDNESS:
(D) TOPOLOGY: linear (xi) SEQUENCE DESCRIPTION: SEQ ID NO:14:

```
Ile Asn Pro Leu Ala Gln Pro Val Ile Tyr Ser Thr Ile Phe Ala Gly
1               5                   10                  15

Thr Leu Ile Thr Ala Leu Ser Ser His Trp Phe Phe Thr Trp Val Gly
            20                  25                  30

Leu Glu Met Asn Met Leu Ala Phe Ile Pro Val Leu Thr Lys Lys Met
        35                  40                  45

Asn Pro Arg Ser Thr Glu Ala Ala Ile Lys Tyr Phe Leu Thr Gln Ala
    50                  55                  60

Thr Ala Ser Met Ile Leu Leu Met Ala Ile Leu Phe Asn Asn Met Leu
65                  70                  75                  80

Ser Gly Gln Trp Thr Met Thr Asn Thr Thr Asn Gln Tyr Ser Ser Leu
                85                  90                  95

Met Ile Met Met Ala Met Ala Met Lys Leu Gly Met Ala Pro Phe His
            100                 105                 110

Phe Trp Val Pro Glu Val Thr Gln Gly Thr Pro Leu Thr Ser Gly Leu
        115                 120                 125

Leu Leu Leu Thr Trp Gln Lys Leu Ala Pro Ile Ser Ile Met Tyr Gln
130                 135                 140

Ile Ser Pro Ser Leu Asn Val Ser Leu Leu Thr Leu Ser Ile Leu
145                 150                 155                 160

Ser Ile Met Ala Gly Ser Trp Gly Gly Leu Asn Gln Thr Gln Leu Arg
                165                 170                 175

Lys Ile Leu Ala Tyr Ser Ser Ile Thr His Met Gly Trp Met Met Ala
            180                 185                 190

Val Leu Pro Tyr Asn Pro Asn Met Thr Ile Leu Asn Leu Thr Ile Tyr
        195                 200                 205

Ile Ile Leu Thr Thr Thr Ala Phe Leu Leu Leu Asn Leu Asn Ser Ser
210                 215                 220

Thr Thr Thr Leu Leu Leu Ser Arg Thr Trp Asn Lys Leu Thr Trp Leu
225                 230                 235                 240

Thr Pro Leu Ile Pro Ser Thr Leu Leu Ser Leu Gly Gly Leu Pro Pro
                245                 250                 255

Leu Thr Gly Phe Leu Pro Lys Trp Ala Ile Ile Glu Glu Phe Thr Lys
            260                 265                 270

Asn Asn Ser Leu Ile Ile Pro Thr Ile Met Ala Thr Ile Thr Leu Leu
        275                 280                 285

Asn Leu Tyr Phe Tyr Leu Arg Leu Ile Tyr Ser Thr Ser Ile Thr Leu
    290                 295                 300

Leu Pro Met Ser Asn Asn Val Lys Met Lys Trp Gln Phe Glu His Thr
305                 310                 315                 320

Lys Pro Thr Pro Phe Leu Pro Thr Leu Ile Ala Leu Thr Thr Leu Leu
                325                 330                 335

Leu Pro Ile Ser Pro Phe Met Leu Met Ile Leu
            340                 345
```

(2) INFORMATION FOR SEQ ID NO:15:

(i) SEQUENCE CHARACTERISTICS:
(A) LENGTH: 513 amino acids
(B) TYPE: amino acid
(C) STRANDEDNESS:
(D) TOPOLOGY: linear (xi) SEQUENCE DESCRIPTION: SEQ ID NO:15:

```
Met Phe Ala Asp Arg Trp Leu Phe Ser Thr Asn His Lys Asp Ile Gly
1               5                   10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Ser Val Asp
    130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Thr Gln Tyr Gln Thr Pro Leu Phe Val Trp Ser Val Leu Ile Thr Ala
            180                 185                 190

Val Leu Leu Leu Ser Leu Pro Val Leu Ala Ala Gly Ile Thr Met
        195                 200                 205

Leu Leu Thr Asp Arg Asn Leu Asn Thr Thr Phe Phe Asp Pro Ala Gly
    210                 215                 220

Gly Gly Asp Pro Ile Leu Tyr Gln His Leu Phe Trp Phe Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly
            260                 265                 270

Met Val Trp Ala Met Met Ser Ile Gly Phe Leu Gly Phe Ile Val Trp
        275                 280                 285

Ala His His Met Phe Thr Val Gly Met Asp Val Asp Thr Arg Ala Tyr
    290                 295                 300

Phe Thr Ser Ala Thr Met Ile Ile Ala Ile Pro Thr Gly Val Lys Val
305                 310                 315                 320

Phe Ser Trp Leu Ala Thr Leu His Gly Ser Asn Met Lys Trp Ser Ala
                325                 330                 335

Ala Val Leu Trp Ala Leu Gly Phe Ile Phe Leu Phe Thr Val Gly Gly
            340                 345                 350

Leu Thr Gly Ile Val Leu Ala Asn Ser Ser Leu Asp Ile Val Leu His
        355                 360                 365

Asp Thr Tyr Tyr Val Val Ala His Phe His Tyr Val Leu Ser Met Gly
    370                 375                 380

Ala Val Phe Ala Ile Met Gly Gly Phe Ile His Trp Phe Pro Leu Phe
385                 390                 395                 400

Ser Gly Tyr Thr Leu Asp Gln Thr Tyr Ala Lys Ile His Phe Thr Ile
```

```
                        405                 410                 415
Met Phe Ile Gly Val Asn Leu Thr Phe Phe Pro Gln His Phe Leu Gly
                420                 425                 430

Leu Ser Gly Met Pro Arg Arg Tyr Ser Asp Tyr Pro Asp Ala Tyr Thr
            435                 440                 445

Thr Trp Asn Ile Leu Ser Ser Val Gly Ser Phe Ile Ser Leu Thr Ala
    450                 455                 460

Val Met Leu Met Ile Phe Met Ile Trp Glu Ala Phe Ala Ser Lys Arg
465                 470                 475                 480

Lys Val Leu Met Val Glu Glu Pro Ser Met Asn Leu Glu Trp Leu Tyr
                485                 490                 495

Gly Cys Pro Pro Pro Tyr His Thr Phe Glu Glu Pro Val Tyr Met Lys
            500                 505                 510

Ser (2) INFORMATION FOR SEQ ID NO:16:

(i) SEQUENCE CHARACTERISTICS:
        (A) LENGTH: 227 amino acids
        (B) TYPE: amino acid
        (C) STRANDEDNESS:
        (D) TOPOLOGY: linear (xi) SEQUENCE DESCRIPTION: SEQ ID NO:16:

Met Ala His Ala Ala Gln Val Gly Leu Gln Asp Ala Thr Ser Pro Ile
1               5                   10                  15

Met Glu Glu Leu Ile Thr Phe His Asp His Ala Leu Met Ile Ile Phe
                20                  25                  30

Leu Ile Cys Phe Leu Val Leu Tyr Ala Leu Phe Leu Thr Leu Thr Thr
            35                  40                  45

Lys Leu Thr Asn Thr Asn Ile Ser Asp Ala Gln Glu Met Glu Thr Val
        50                  55                  60

Trp Thr Ile Leu Pro Ala Ile Ile Leu Val Leu Ile Ala Leu Pro Ser
65                  70                  75                  80

Leu Arg Ile Leu Tyr Met Thr Asp Glu Val Asn Asp Pro Ser Leu Thr
                85                  90                  95

Ile Lys Ser Ile Gly His Gln Trp Tyr Trp Thr Tyr Glu Tyr Thr Asp
            100                 105                 110

Tyr Gly Gly Leu Ile Phe Asn Ser Tyr Met Leu Pro Pro Leu Phe Leu
        115                 120                 125

Glu Pro Gly Asp Leu Arg Leu Leu Asp Val Asp Asn Arg Val Val Leu
130                 135                 140

Pro Ile Glu Ala Pro Ile Arg Met Met Ile Thr Ser Gln Asp Val Leu
145                 150                 155                 160

His Ser Trp Ala Val Pro Thr Leu Gly Leu Lys Thr Asp Ala Ile Pro
                165                 170                 175

Gly Arg Leu Asn Gln Thr Thr Phe Thr Ala Thr Arg Pro Gly Val Tyr
            180                 185                 190

Tyr Gly Gln Cys Ser Glu Ile Cys Gly Ala Asn His Ser Phe Met Pro
        195                 200                 205

Ile Val Leu Glu Leu Ile Pro Leu Lys Ile Phe Glu Met Gly Pro Val
    210                 215                 220

Phe Thr Leu
225
```

(2) INFORMATION FOR SEQ ID NO:17:

(i) SEQUENCE CHARACTERISTICS:
        (A) LENGTH: 68 amino acids
        (B) TYPE: amino acid
        (C) STRANDEDNESS:
        (D) TOPOLOGY: linear (xi) SEQUENCE DESCRIPTION: SEQ ID NO:17:

```
Met Pro Gln Leu Asn Thr Thr Val Trp Pro Thr Met Ile Thr Pro Met
 1               5                  10                  15

Leu Leu Thr Leu Phe Leu Ile Thr Gln Leu Lys Met Leu Asn Thr Asn
                20                  25                  30

Tyr His Leu Pro Pro Ser Pro Lys Pro Met Lys Met Lys Asn Tyr Asn
                35                  40                  45

Lys Pro Trp Glu Pro Lys Trp Thr Lys Ile Cys Ser Leu His Ser Leu
 50                  55                  60

Pro Pro Gln Ser
 65
```

(2) INFORMATION FOR SEQ ID NO:18:

(i) SEQUENCE CHARACTERISTICS:
        (A) LENGTH: 226 amino acids
        (B) TYPE: amino acid
        (C) STRANDEDNESS:
        (D) TOPOLOGY: linear (xi) SEQUENCE DESCRIPTION: SEQ ID NO:18:

```
Met Asn Glu Asn Leu Phe Ala Ser Phe Ile Ala Pro Thr Ile Leu Gly
 1               5                  10                  15

Leu Pro Ala Ala Val Leu Ile Ile Leu Phe Pro Pro Leu Leu Ile Pro
                20                  25                  30

Thr Ser Lys Tyr Leu Ile Asn Asn Arg Leu Ile Thr Thr Gln Gln Trp
                35                  40                  45

Leu Ile Lys Leu Thr Ser Lys Gln Met Met Thr Met His Asn Thr Lys
 50                  55                  60

Gly Arg Thr Trp Ser Leu Met Leu Val Ser Leu Ile Ile Phe Ile Ala
 65                  70                  75                  80

Thr Thr Asn Leu Leu Gly Leu Leu Pro His Ser Phe Thr Pro Thr Thr
                85                  90                  95

Gln Leu Ser Met Asn Leu Ala Met Ala Ile Pro Leu Trp Ala Gly Thr
                100                 105                 110

Val Ile Met Gly Phe Arg Ser Lys Ile Lys Asn Ala Leu Ala His Phe
                115                 120                 125

Leu Pro Gln Gly Thr Pro Thr Pro Leu Ile Pro Met Leu Val Ile Ile
                130                 135                 140

Glu Thr Ile Ser Leu Leu Ile Gln Pro Met Ala Leu Ala Val Arg Leu
 145                 150                 155                 160

Thr Ala Asn Ile Thr Ala Gly His Leu Leu Met His Leu Ile Gly Ser
                165                 170                 175

Ala Thr Leu Ala Met Ser Thr Ile Asn Leu Pro Ser Thr Leu Ile Ile
                180                 185                 190

Phe Thr Ile Leu Ile Leu Leu Thr Ile Leu Glu Ile Ala Val Ala Leu
                195                 200                 205

Ile Gln Ala Tyr Val Phe Thr Leu Leu Val Ser Leu Tyr Leu His Asp
 210                 215                 220

Asn Thr
```

225

(2) INFORMATION FOR SEQ ID NO:19:

(i) SEQUENCE CHARACTERISTICS:
        (A) LENGTH: 261 amino acids
        (B) TYPE: amino acid
        (C) STRANDEDNESS:
        (D) TOPOLOGY: linear (xi) SEQUENCE DESCRIPTION: SEQ ID NO:19:

```
Met Thr His Gln Ser His Ala Tyr His Met Val Lys Pro Ser Pro Trp
1               5                   10                  15

Pro Leu Thr Gly Ala Leu Ser Ala Leu Leu Met Thr Ser Gly Leu Ala
            20                  25                  30

Met Trp Phe His Phe His Ser Met Thr Leu Leu Met Leu Gly Leu Leu
        35                  40                  45

Thr Asn Thr Leu Thr Met Tyr Gln Trp Trp Arg Asp Val Thr Arg Glu
    50                  55                  60

Ser Thr Tyr Gln Gly His His Thr Pro Val Gln Lys Gly Leu Arg
65                  70                  75                  80

Tyr Gly Met Ile Leu Phe Ile Thr Ser Glu Val Phe Phe Ala Gly
                85                  90                  95

Phe Phe Trp Ala Phe Tyr His Ser Ser Leu Ala Pro Thr Pro Gln Leu
                100                 105                 110

Gly Gly His Trp Pro Pro Thr Gly Ile Thr Pro Leu Asn Pro Leu Glu
            115                 120                 125

Val Pro Leu Leu Asn Thr Ser Val Leu Leu Ala Ser Gly Val Ser Ile
130                 135                 140

Thr Trp Ala His His Ser Leu Met Glu Asn Asn Arg Asn Gln Met Ile
145                 150                 155                 160

Gln Ala Leu Leu Ile Thr Ile Leu Leu Gly Leu Tyr Phe Thr Leu Leu
                165                 170                 175

Gln Ala Ser Glu Tyr Phe Glu Ser Pro Phe Thr Ile Ser Asp Gly Ile
            180                 185                 190

Tyr Gly Ser Thr Phe Phe Val Ala Thr Gly Phe His Gly Leu His Val
        195                 200                 205

Ile Ile Gly Ser Thr Phe Leu Thr Ile Cys Phe Ile Arg Gln Leu Met
210                 215                 220

Phe His Phe Thr Ser Lys His Phe Gly Phe Glu Ala Ala Ala Trp
225                 230                 235                 240

Tyr Trp His Phe Val Asp Val Val Trp Leu Phe Leu Tyr Val Ser Ile
                245                 250                 255

Tyr Trp Trp Gly Ser
            260
```

(2) INFORMATION FOR SEQ ID NO:20:

(i) SEQUENCE CHARACTERISTICS:
        (A) LENGTH: 115 amino acids
        (B) TYPE: amino acid
        (C) STRANDEDNESS:
        (D) TOPOLOGY: linear (xi) SEQUENCE DESCRIPTION: SEQ ID NO:20:

```
Met Asn Phe Ala Leu Ile Leu Met Ile Asn Thr Leu Leu Ala Leu Leu
1               5                   10                  15

Leu Met Ile Ile Thr Phe Trp Leu Pro Gln Leu Asn Gly Tyr Met Glu
```

```
                    20                  25                  30
Lys Ser Thr Pro Tyr Glu Cys Gly Phe Asp Pro Met Ser Pro Ala Arg
             35                  40                  45

Val Pro Phe Ser Met Lys Phe Leu Val Ala Ile Thr Phe Leu Leu
 50                  55                  60

Phe Asp Leu Glu Ile Ala Leu Leu Leu Pro Leu Pro Trp Ala Leu Gln
 65                  70                  75                  80

Thr Thr Asn Leu Pro Leu Met Val Met Ser Ser Leu Leu Leu Ile Ile
                 85                  90                  95

Ile Leu Ala Leu Ser Leu Ala Tyr Glu Trp Leu Gln Lys Gly Leu Asp
                100                 105                 110

Trp Thr Glu
        115

(2) INFORMATION FOR SEQ ID NO:21:

(i) SEQUENCE CHARACTERISTICS:
        (A) LENGTH: 98 amino acids
        (B) TYPE: amino acid
        (C) STRANDEDNESS:
        (D) TOPOLOGY: linear (xi) SEQUENCE DESCRIPTION: SEQ ID NO:21:

Met Pro Leu Ile Tyr Met Asn Ile Met Leu Ala Phe Thr Ile Ser Leu
 1               5                  10                  15

Leu Gly Met Leu Val Tyr Arg Ser His Leu Met Ser Ser Leu Leu Cys
                20                  25                  30

Leu Glu Gly Met Met Leu Ser Leu Phe Ile Met Ala Thr Leu Met Thr
                35                  40                  45

Leu Asn Thr His Ser Leu Leu Ala Asn Ile Val Pro Ile Ala Met Leu
                50                  55                  60

Val Phe Ala Ala Cys Glu Ala Ala Val Gly Leu Ala Leu Leu Val Ser
 65                  70                  75                  80

Ile Ser Asn Thr Tyr Gly Leu Asp Tyr Val His Asn Leu Asn Leu Leu
                85                  90                  95

Gln Cys (2) INFORMATION FOR SEQ ID NO:22:

(i) SEQUENCE CHARACTERISTICS:
        (A) LENGTH: 459 amino acids
        (B) TYPE: amino acid
        (C) STRANDEDNESS:
        (D) TOPOLOGY: linear (xi) SEQUENCE DESCRIPTION: SEQ ID NO:22:

Met Leu Lys Leu Ile Val Pro Thr Ile Met Leu Leu Pro Leu Thr Trp
 1               5                  10                  15

Leu Ser Lys Lys His Met Ile Trp Ile Asn Thr Thr His Ser Leu
                20                  25                  30

Ile Ile Ser Ile Ile Pro Leu Leu Phe Phe Asn Gln Ile Asn Asn Asn
                35                  40                  45

Leu Phe Ser Cys Ser Pro Thr Phe Ser Ser Asp Pro Leu Thr Thr Pro
 50                  55                  60

Leu Leu Met Leu Thr Thr Trp Leu Leu Pro Leu Thr Ile Met Ala Ser
 65                  70                  75                  80

Gln Arg His Leu Ser Ser Glu Pro Leu Ser Arg Lys Lys Leu Tyr Leu
                85                  90                  95
```

```
Ser Met Leu Ile Ser Leu Gln Ile Ser Leu Ile Met Thr Phe Thr Ala
            100                 105                 110

Thr Glu Leu Ile Met Phe Tyr Ile Phe Phe Glu Thr Thr Leu Ile Pro
            115                 120                 125

Thr Leu Ala Ile Ile Thr Arg Trp Gly Asn Gln Pro Glu Arg Leu Asn
            130                 135             140

Ala Gly Thr Tyr Phe Leu Phe Tyr Thr Leu Val Gly Ser Leu Pro Leu
145                     150                 155                 160

Leu Ile Ala Leu Ile Tyr Thr His Asn Thr Leu Gly Ser Leu Asn Ile
                165                 170                 175

Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
            195                 200                 205

Leu Tyr Gly Leu His Leu Trp Leu Pro Lys Ala His Val Glu Ala Pro
            210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
            275                 280                 285

Ser Ser Ile Ser His Met Ala Leu Val Val Thr Ala Ile Leu Ile Gln
            290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
            355                 360                 365

Leu Pro Pro Thr Ile Asn Leu Leu Gly Glu Leu Ser Val Leu Val Thr
370                 375                 380

Thr Phe Ser Trp Ser Asn Ile Thr Leu Leu Thr Gly Leu Asn Met
385                 390                 395                 400

Leu Val Thr Ala Leu Tyr Ser Leu Tyr Met Phe Thr Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
            435                 440                 445

Leu Asn Pro Asp Ile Ile Thr Gly Phe Ser Ser
            450                 455

(2) INFORMATION FOR SEQ ID NO:23:

(i) SEQUENCE CHARACTERISTICS:
        (A) LENGTH: 603 amino acids
        (B) TYPE: amino acid
        (C) STRANDEDNESS:
        (D) TOPOLOGY: linear
```

-continued (xi) SEQUENCE DESCRIPTION: SEQ ID NO:23:

```
Met Thr Met His Thr Thr Met Thr Thr Leu Thr Leu Thr Ser Leu Ile
  1               5                  10                  15

Pro Pro Ile Leu Thr Thr Leu Val Asn Pro Asn Lys Lys Asn Ser Tyr
             20                  25                  30

Pro His Tyr Val Lys Ser Ile Val Ala Ser Thr Phe Ile Ile Ser Leu
             35                  40                  45

Phe Pro Thr Thr Met Phe Met Cys Leu Asp Gln Glu Val Ile Ile Ser
 50                  55                  60

Asn Trp His Trp Ala Thr Thr Gln Thr Thr Gln Leu Ser Leu Ser Phe
 65                  70                  75                  80

Lys Leu Asp Tyr Phe Ser Met Met Phe Ile Pro Val Ala Leu Phe Val
             85                  90                  95

Thr Trp Ser Ile Met Glu Phe Ser Leu Trp Tyr Met Asn Ser Asp Pro
            100                 105                 110

Asn Ile Asn Gln Phe Phe Lys Tyr Leu Leu Ile Phe Leu Ile Thr Met
            115                 120                 125

Leu Ile Leu Val Thr Ala Asn Asn Leu Phe Gln Leu Phe Ile Gly Trp
130                 135                 140

Glu Gly Val Gly Ile Met Ser Phe Leu Leu Ile Ser Trp Trp Tyr Ala
145                 150                 155                 160

Arg Ala Asp Ala Asn Thr Ala Ala Ile Gln Ala Ile Leu Tyr Asn Arg
            165                 170                 175

Ile Gly Asp Ile Gly Phe Ile Leu Ala Leu Ala Trp Phe Ile Leu His
            180                 185                 190

Ser Asn Ser Trp Asp Pro Gln Gln Met Ala Leu Leu Asn Ala Asn Pro
            195                 200                 205

Ser Leu Thr Pro Leu Leu Gly Leu Leu Leu Ala Ala Ala Gly Lys Ser
210                 215                 220

Ala Gln Leu Gly Leu His Pro Trp Leu Pro Ser Ala Met Glu Gly Pro
225                 230                 235                 240

Thr Pro Val Ser Ala Leu Leu His Ser Ser Thr Met Val Val Ala Gly
            245                 250                 255

Ile Phe Leu Leu Ile Arg Phe His Pro Leu Ala Glu Asn Ser Pro Leu
            260                 265                 270

Ile Gln Thr Leu Thr Leu Cys Leu Gly Ala Ile Thr Thr Leu Phe Ala
            275                 280                 285

Ala Val Cys Ala Leu Thr Gln Asn Asp Ile Lys Lys Ile Val Ala Phe
290                 295                 300

Ser Thr Ser Ser Gln Leu Gly Leu Met Met Val Thr Ile Gly Ile Asn
305                 310                 315                 320

Gln Pro His Leu Ala Phe Leu His Ile Cys Thr His Ala Phe Phe Lys
            325                 330                 335

Ala Met Leu Phe Met Cys Ser Gly Ser Ile Ile His Asn Leu Asn Asn
            340                 345                 350

Glu Gln Asp Ile Arg Lys Met Gly Gly Leu Leu Lys Thr Met Pro Leu
            355                 360                 365

Thr Ser Thr Ser Leu Thr Ile Gly Ser Leu Ala Leu Ala Gly Met Pro
            370                 375                 380

Phe Leu Thr Gly Phe Tyr Ser Lys Asp His Ile Ile Glu Thr Ala Asn
385                 390                 395                 400

Met Ser Tyr Thr Asn Ala Trp Ala Leu Ser Ile Thr Leu Ile Ala Thr
            405                 410                 415
```

```
Ser Leu Thr Ser Ala Tyr Ser Thr Arg Met Ile Leu Leu Thr Leu Thr
            420                 425                 430

Gly Gln Pro Arg Phe Pro Thr Leu Thr Asn Ile Asn Glu Asn Asn Pro
            435                 440                 445

Thr Leu Leu Asn Pro Ile Lys Arg Leu Ala Ala Gly Ser Leu Phe Ala
            450                 455                 460

Gly Phe Leu Ile Thr Asn Asn Ile Ser Pro Ala Ser Pro Phe Gln Thr
465                 470                 475                 480

Thr Ile Pro Leu Tyr Leu Lys Leu Thr Ala Leu Ala Val Thr Phe Leu
                485                 490                 495

Gly Leu Leu Thr Ala Leu Asp Leu Asn Tyr Leu Thr Asn Lys Leu Lys
                500                 505                 510

Met Lys Ser Pro Leu Cys Thr Phe Tyr Phe Ser Asn Met Leu Gly Phe
            515                 520                 525

Tyr Pro Ser Ile Thr His Arg Thr Ile Pro Tyr Leu Gly Leu Leu Thr
            530                 535                 540

Ser Gln Asn Leu Pro Leu Leu Leu Asp Leu Thr Trp Leu Glu Lys
545                 550                 555                 560

Leu Leu Pro Lys Thr Ile Ser Gln His Gln Ile Ser Thr Ser Ile Ile
                565                 570                 575

Thr Ser Thr Gln Lys Gly Met Ile Lys Leu Tyr Phe Leu Ser Phe Phe
                580                 585                 590

Phe Pro Leu Ile Leu Thr Leu Leu Leu Ile Thr
                595                 600

(2) INFORMATION FOR SEQ ID NO:24:

(i) SEQUENCE CHARACTERISTICS:
        (A) LENGTH: 174 amino acids
        (B) TYPE: amino acid
        (C) STRANDEDNESS:
        (D) TOPOLOGY: linear (xi) SEQUENCE DESCRIPTION: SEQ ID NO:24:

Met Met Tyr Ala Leu Phe Leu Leu Ser Val Gly Leu Val Met Gly Phe
1               5                   10                  15

Val Gly Phe Ser Ser Lys Pro Ser Pro Ile Tyr Gly Gly Leu Val Leu
            20                  25                  30

Ile Val Ser Gly Val Val Gly Cys Val Ile Ile Leu Asn Phe Gly Gly
            35                  40                  45

Gly Tyr Met Gly Leu Met Val Phe Leu Ile Tyr Leu Gly Gly Met Met
            50                  55                  60

Val Val Phe Gly Tyr Thr Thr Ala Met Ala Ile Glu Glu Tyr Pro Glu
65                  70                  75                  80

Ala Trp Gly Ser Gly Val Glu Val Leu Val Ser Val Leu Val Gly Leu
                85                  90                  95

Ala Met Glu Val Gly Leu Val Leu Trp Val Lys Glu Tyr Asp Gly Val
            100                 105                 110

Val Val Val Val Asn Phe Asn Ser Val Gly Ser Trp Met Ile Tyr Glu
            115                 120                 125

Gly Glu Gly Ser Gly Leu Ile Arg Glu Asp Pro Ile Gly Ala Gly Ala
            130                 135                 140

Leu Tyr Asp Tyr Gly Arg Trp Leu Val Val Thr Gly Trp Thr Leu
145                 150                 155                 160

Phe Val Gly Val Tyr Ile Val Ile Glu Ile Ala Arg Gly Asn
```

165            170

(2) INFORMATION FOR SEQ ID NO:25:

(i) SEQUENCE CHARACTERISTICS:
        (A) LENGTH: 380 amino acids
        (B) TYPE: amino acid
        (C) STRANDEDNESS:
        (D) TOPOLOGY: linear (xi) SEQUENCE DESCRIPTION: SEQ ID NO:25:

```
Met Thr Pro Met Arg Lys Ile Asn Pro Leu Met Lys Leu Ile Asn His
 1               5                  10                  15

Ser Phe Ile Asp Leu Pro Thr Pro Ser Asn Ile Ser Ala Trp Trp Asn
            20                  25                  30

Phe Gly Ser Leu Leu Gly Ala Cys Leu Ile Leu Gln Ile Thr Thr Gly
        35                  40                  45

Leu Phe Leu Ala Met His Tyr Ser Pro Asp Ala Ser Thr Ala Phe Ser
 50                  55                  60

Ser Ile Ala His Ile Thr Arg Asp Val Asn Tyr Gly Trp Ile Ile Arg
 65                  70                  75                  80

Tyr Leu His Ala Asn Gly Ala Ser Met Phe Phe Ile Cys Leu Phe Leu
                85                  90                  95

His Ile Gly Arg Gly Leu Tyr Tyr Gly Ser Phe Leu Tyr Ser Glu Thr
            100                 105                 110

Trp Asn Ile Gly Ile Ile Leu Leu Leu Ala Thr Met Ala Thr Ala Phe
        115                 120                 125

Met Gly Tyr Val Leu Pro Trp Gly Gln Met Ser Phe Trp Gly Ala Thr
130                 135                 140

Val Ile Thr Asn Leu Leu Ser Ala Ile Pro Tyr Ile Gly Thr Asp Leu
145                 150                 155                 160

Val Gln Trp Ile Trp Gly Gly Tyr Ser Val Asp Ser Pro Thr Leu Thr
                165                 170                 175

Arg Phe Phe Thr Phe His Phe Ile Leu Pro Phe Ile Ile Ala Ala Leu
            180                 185                 190

Ala Thr Leu His Leu Leu Phe Leu His Glu Thr Gly Ser Asn Asn Pro
        195                 200                 205

Leu Gly Ile Thr Ser His Ser Asp Lys Ile Thr Phe His Pro Tyr Tyr
    210                 215                 220

Thr Ile Lys Asp Ala Leu Gly Leu Leu Phe Leu Leu Ser Leu Met
225                 230                 235                 240

Thr Leu Thr Leu Phe Ser Pro Asp Leu Leu Gly Asp Pro Asp Asn Tyr
                245                 250                 255

Thr Leu Ala Asn Pro Leu Asn Thr Pro Pro His Ile Lys Pro Glu Trp
            260                 265                 270

Tyr Phe Leu Phe Ala Tyr Thr Ile Leu Arg Ser Val Pro Asn Lys Leu
        275                 280                 285

Gly Gly Val Leu Ala Leu Leu Ser Ile Leu Ile Leu Ala Met Ile
290                 295                 300

Pro Ile Leu His Met Ser Lys Gln Gln Ser Met Met Phe Arg Pro Leu
305                 310                 315                 320

Ser Gln Ser Leu Tyr Trp Leu Leu Ala Ala Asp Leu Leu Ile Leu Thr
                325                 330                 335

Trp Ile Gly Gly Gln Pro Val Ser Tyr Pro Phe Thr Ile Ile Gly Gln
            340                 345                 350
```

-continued

```
Val Ala Ser Val Leu Tyr Phe Thr Thr Ile Leu Ile Leu Met Pro Thr
        355                 360                 365

Ile Ser Leu Ile Glu Asn Lys Met Leu Lys Trp Ala
    370                 375                 380
```

(2) INFORMATION FOR SEQ ID NO:26:

(i) SEQUENCE CHARACTERISTICS:
        (A) LENGTH: 823 base pairs
        (B) TYPE: nucleic acid
        (C) STRANDEDNESS: single
        (D) TOPOLOGY: linear (xi) SEQUENCE DESCRIPTION: SEQ ID NO:26:

```
CCCACATTAG GCTTAAAAAC AGATGCAATT CCCGGACGTC TAAACCAAAC CACTTTCACC      60

GCTACACGAC CGGGGGTATA CTACGGTCAA TGCTCTGAAA TCTGTGGAGC AAACCACAGT     120

TTCATGCCCA TCGTCCTAGA ATTAATTCCC CTAAAAATCT TTGAAATAGG GCCCGTATTT     180

ACCCTATAGC ACCCCCTCTA CCCCCTCTAG AGCCCACTGT AAAGCTAACT TAGCATTAAC     240

CTTTTAAGTT AAAGATTAAG AGAACCAACA CCTCTTTACA GTGAAATGCC CCAACTAAAT     300

ACTACCGTAT GGCCCACCAT AATTACCCCC ATACTCCTTA CACTATTCCT CATCACCCAA     360

CTAAAAATAT TAAACACAAA CTACCACCTA CCTCCCTCAC CAAAGCCCAT AAAAATAAAA     420

AATTATAACA AACCCTGAGA ACCAAAATGA ACGAAAATCT GTTCGCTTCA TTCATTGCCC     480

CCACAATCCT AGGCCTACCC GCCGCAGTAC TGATCATTCT ATTTCCCCCT CTATTGATCC     540

CCACCTCCAA ATATCTCATC AACAACCGAC TAATCACCAC CCAACAATGA CTAATCAAAC     600

TAACCTCAAA ACAAATGATA ACCATACACA ACACTAAAGG ACGAACCTGA TCTCTTATAC     660

TAGTATCCTT AATCATTTTT ATTGCCACAA CTAACCTCCT CGGACTCCTG CCTCACTCAT     720

TTACACCAAC CACCCAACTA TCTATAAACC TAGCCATGGC CATCCCCTTA TGAGCGGGCA     780

CAGTGATTAT AGGCTTTCGC TCTAAGATTA AAAATGCCCT AGC                       823
```

DIAGNOSTIC METHOD BASED ON QUANTIFICATION OF EXTRAMITOCHONDRIAL DNA

TECHNICAL FIELD

The present invention relates generally to diseases in which altered mitochondrial function, such as free radical mediated oxidative injury, leads to tissue degeneration and, more specifically, to compositions and methods for detecting predisposition to such diseases by quantifying extramitochondrial DNA.

BACKGROUND OF THE INVENTION

A number of degenerative diseases are thought to be caused by or be associated with alterations in mitochondrial function. These diseases include Alzheimer's Disease, diabetes mellitus, Parkinson's Disease, Huntington's disease, dystonia, Leber's hereditary optic neuropathy, schizophrenia, and myodegenerative disorders such as "mitochondrial encephalopathy, lactic acidosis, and stroke" (MELAS), and "myoclonic epilepsy ragged red fiber syndrome" (MERRF). Other diseases involving altered metabolism or respiration within cells may also be regarded as diseases associated with altered mitochondrial function.

Functional mitochondria contain gene products encoded by mitochondrial genes situated in mitochondrial DNA (mtDNA) and by extramitochondrial genes not situated in the circular mitochondrial genome. The 16.5 kb mtDNA encodes 22 tRNAs, two ribosomal RNAs (rRNA) and only 13 enzymes of the electron transport chain (ETC), the elaborate multi-complex mitochondrial assembly where, for example, respiratory oxidative phosphorylation takes place. The overwhelming majority of mitochondrial structural and functional proteins are encoded by extramitochondrial, and in most cases presumably nuclear, genes. Accordingly, mitochondrial and extramitochondrial genes may interact directly, or indirectly via gene products and their downstream intermediates, including metabolites, catabolites, substrates, precursors, cofactors and the like. Alterations in mitochondrial function, for example impaired electron transport activity, defective oxidative phosphorylation or increased free radical production, may therefore arise as the result of defective mtDNA, defective extramitochondrial DNA, defective mitochondrial or extramitochondrial gene products, defective downstream intermediates or a combination of these and other factors.

Mitochondria are the subcellular organelles that manufacture bioenergetically essential adenosine triphosphate (ATP) by oxidative phosphorylation. Defective mitochondrial activity, including failure at any step of the ETC, may result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury, such as that found in a number of degenerative diseases, and in ischemia (i.e., stroke).

There are at least two deleterious consequences of exposure to reactive free radicals arising from mitochondrial dysfunction that adversely impact the mitochondria themselves. First, free radical mediated damage may inactivate one or more of the myriad proteins of the ETC. According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and halting the production of a vital biochemical energy source. In addition, mitochondrial proteins such as cytochrome c and "apoptosis inducing factor" may leak out of the mitochondria after permeability transition and may induce the genetically programmed cell suicide sequence known as apoptosis or programmed cell death (PCD).

Second, free radical mediated damage may result in catastrophic mitochondrial collapse that has been termed "transition permeability". For example, rapid mitochondrial permeability transition likely entails changes in the inner mitochondrial transmembrane protein adenylate translocase that results in the formation of a "pore." In any event, because permeability transition is potentiated by free radical exposure, it may be more likely to occur in the mitochondria of cells from patients having mitochondria associated diseases that are chronically exposed to such reactive free radicals.

Altered mitochondrial function characteristic of the mitochondria associated diseases may also be related to loss of mitochondrial membrane electrochemical potential by mechanisms other than free radical oxidation, and such transition permeability may result from direct or indirect effects of mitochondrial genes, gene products or related downstream mediator molecules and/or extramitochondrial genes, gene products or related downstream mediators, or from other known or unknown causes.

Diabetes mellitus is a common, degenerative disease affecting 5 to 10 percent of the population in developed countries. The propensity for developing diabetes mellitus is reportedly maternally inherited, suggesting a mitochondrial genetic involvement. (Alcolado, J. C. and Alcolado, R., Br. Med. J. 302:1178–1180 (1991); Reny, S. L., International J. Epidem. 23:886–890 (1994)). Diabetes is a heterogenous disorder with a strong genetic component; monozygotic twins are highly concordant and there is a high incidence of the disease among first degree relatives of affected individuals.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). These forms of diabetes mellitus, NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Parkinson's disease (PD) is a progressive, neurodegenerative disorder associated with altered mitochondrial function and characterized by the loss and/or atrophy of dopamine-containing neurons in the pars compacta of the substantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man at least in part through its effects on mitochondria. MPTP is converted to its active metabolite, MPP+, in dopamine neurons; it then becomes concentrated in the mitochondria. The MPP+ then selectively inhibits the mitochondrial enzyme NADH:ubiquinone oxidoreductase ("Complex I"), leading to the increased production of free radicals, reduced production of adenosine triphosphate, and ultimately, the death of affected dopamine neurons.

Mitochondrial Complex I is composed of 40–50 subunits; most are encoded by the nuclear genome and seven by the mitochondrial genome. Since parkinsonism may be induced by exposure to mitochondrial toxins that affect Complex I activity, it appears likely that defects in Complex I proteins may contribute to the pathogenesis of PD by causing a similar biochemical deficiency in Complex I activity. Indeed, defects in mitochondrial Complex I activity have been reported in the blood and brain of PD patients (Parker et al., *Am. J. Neurol.* 26:719–723, 1989).

Alzheimer's disease (AD) is a progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of this enzyme in AD patients and in the brains of AD patients at autopsy has been found to be abnormally low. This suggests that the COX in AD patients is defective, leading to decreased catalytic activity that in some fashion causes or contributes to the symptoms that are characteristic of AD.

Focal defects in energy metabolism in the mitochondria, with accompanying increases in oxidative stress, may be associated with AD. It is well-established that energy metabolism is impaired in AD brain (Palmer et al., *Brain Res.* 645:338–42, 1994; Pappolla et al., *Am. J. Pathol.* 140:621–28, 1992; Jeandel et al., *Gerontol.* 35:275, 1989; Balazs et al., *Neurochem. Res.* 19:1131–37, 1994; Mecocci et al., *Ann. Neurol.* 36:747–751, 1994; Gsell et al., *J. Neurochem.* 64:1216–23, 1995). For example, regionally specific deficits in energy metabolism in AD brains have been reported in a number of positron emission tomography studies (Kuhl, et al., *J. Cereb. Blood Flow Metab.* 7:S406, 1987; Grady, et al., *J. Clin. Exp. Neuropsychol.* 10:576–96, 1988; Haxby et al., *Arch. Neurol.* 47:753–60, 1990; Azari et al., *J. Cereb. Blood Flow Metab.* 13:438–47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., *Proc. Nat. Acad. Sci. USA* 91:7787–91, 1994). Cortical tissue from postmortem AD brain shows decreased activity of the mitochondrial enzymes pyruvate dehydrogenase (Sheu et al., *Ann. Neurol.* 17:444–49, 1985) and α-ketoglutarate dehydrogenase (Mastrogiacomo et al., *J. Neurochem.* 6:2007–14, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., *Neurobiol. of Aging* 15:117–32, 1994; Pettigrew et al., *Neurobiol. of Aging* 16:973–75, 1995). In addition, the levels of pyruvate, but not of glucose or lactate, are reported to be increased in the cerebrospinal fluid of AD patients, consistent with defects in cerebral mitochondrial electron transport chain (ETC) activity (Parnetti et al., *Neurosci. Lett.* 199:231–33, 1995).

Signs of oxidative injury are prominent features of AD pathology and, as noted above, reactive oxygen species (ROS) are critical mediators of neuronal degeneration. Indeed, studies at autopsy show that markers of protein, DNA and lipid peroxidation are increased in AD brain (Palmer et al., Brain Res. 645:338–42, 1994; Pappolla et al., Am. J. Pathol. 140:621–28, 1992; Jeandel et al., Gerontol. 35:275–82, 1989; Balazs et al., Arch. Neurol. 4:864, 1994; Mecocci et al., Ann. Neurol. 36:747–51, 1994; Smith et al., Proc. Nat. Acad. Sci. USA 88:10540–43, 1991). In hippocampal tissue from AD but not from controls, carbonyl formation indicative of protein oxidation is increased in neuronal cytoplasm, and nuclei of neurons and glia (Smith et al., *Nature* 382:120–21, 1996). Neurofibrillary tangles also appear to be prominent sites of protein oxidation (Schweers et al., *Proc. Nat. Acad. Sci. USA* 92:8463, 1995; Blass et al., *Arch. Neurol.* 4:864, 1990). Under stressed and non-stressed conditions incubation of cortical tissue from AD brains taken at autopsy demonstrate increased free radical production relative to non-AD controls. In addition, the activities of critical antioxidant enzymes, particularly catalase, are reduced in AD (Gsell et al., *J. Neurochem.* 64:1216–23, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

One hallmark pathology of AD is the death of selected neuronal populations in discrete regions of the brain. Cell death in AD is presumed to be apoptotic because signs of programmed cell death (PCD) are seen and indicators of active gliosis and necrosis are not found. (Smale et al., *Exp. Neurolog.* 133:225–230, 1995; Cotman et al., *Molec. Neurobiol.* 10:19–45, 1995.) The consequences of cell death in AD, neuronal and synaptic loss, are closely associated with the clinical diagnosis of AD and are highly correlated with the degree of dementia in AD (DeKosky et al., *Ann. Neurology* 27:457–464, 1990).

Mitochondrial dysfunction is thought to be critical in the cascade of events leading to apoptosis in various cell types (Kroemer et al., *FASEB J.* 9:1277–87, 1995), and may be a cause of apoptotic cell death in neurons of the AD brain.

Altered mitochondrial physiology may be among the earliest events in PCD (Zamzami et al., *J. Exp. Med.* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994). In several cell types, including neurons, reduction in the mitochondrial membrane potential ($\Delta\Psi m$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in mitochondria associated diseases and may further induce pathogenetic events via apoptotic mechanisms.

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al, *Biochim. Biophys. Act.* 1271:63, 1995). Localization of Bcl-2 to this membrane appears to be indispensable for modulation of apoptosis (Nguyen et al., *J. Biol. Chem.* 269:16521–24, 1994). Thus, changes in mitochondrial physiology may be important mediators of apoptosis. To the extent that apoptotic cell death is a prominent feature of neuronal loss in AD, mitochondrial dysfunction may be critical to the progression of this disease and may also be a contributing factor in other mitochondria associated diseases.

Regardless of whether a defect underlying a disease associated with altered mitochondrial function may have mitochondrial or extramitochondrial origins, and regardless of whether a defect underlying altered mitochondrial function has been identified, the present invention provides methods that are useful for determining the risk or presence of diseases associated with such altered mitochondrial function, and for identifying agents that are suitable for treating such diseases. In particular, as is elaborated herein below, the present invention provides compositions and methods for the detection of diseases associated with altered mitochondrial function by quantification of unusual mtDNA-like sequences not found in mitochondria and referred to as extramitochondrial DNA (exmtDNA), and other related advantages.

SUMMARY OF THE INVENTION

Briefly stated, the present invention is directed to compositions and methods useful for detecting mitochondria associated diseases and involving extramitochondrial DNA (exmtDNA) sequences that are highly homologous to mitochondrial DNA (mtDNA). In one aspect the invention provides a method for determining the risk for or presence of a disease associated with altered mitochondrial function in a first subject suspected of having or being at risk for having such a disease, by comparing a ratio r for each of a first and a second biological sample containing extramitochondrial DNA and mitochondrial DNA, the first biological sample being obtained from the first subject and the second sample being obtained from a second subject known to be free of a risk or presence of a disease associated with altered mitochondrial function, using the formula:

$$r = x/(x+y)$$

wherein x is the amount of extramitochondrial DNA in a sample, and y is the amount of mitochondrial DNA in the sample; and therefrom determining the risk or presence of the disease. In an embodiment of the invention, the ratio r is calculated by a method that comprises contacting a biological sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of the primer to the extramitochondrial DNA and to the mitochondrial DNA; and detecting hybridization of the primer to the extramitochondrial DNA and to the mitochondrial DNA, in order to therefrom quantify the extramitochondrial DNA and the mitochondrial DNA.

In another embodiment, the ratio r is calculated by a method comprising contacting a sample containing amplified extramitochondrial DNA and mitochondrial DNA with an oligonucleotide primer having a nucleotide sequence that is complementary to a sequence present in the amplified extramitochondrial DNA and present in the amplified mitochondrial DNA, under conditions and for a time sufficient to allow hybridization of the primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA. In another embodiment of this aspect of the invention the ratio r is calculated by a method comprising contacting a biological sample containing extramitochondrial DNA and mitochondrial DNA with an oligonucleotide primer having a nucleotide sequence that is complementary to a sequence present in the extramitochondrial DNA and present in the mitochondrial DNA, under conditions and for a time sufficient to allow hybridization of said primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from the first product, and therefrom quantifying the extramitochondrial DNA and the mitochondrial DNA.

In another embodiment of this aspect of the invention the ratio r is calculated by a method comprising contacting a sample containing amplified extramitochondrial DNA and mitochondrial DNA with an oligonucleotide primer having a nucleotide sequence that is complementary to a sequence present in the amplified extramitochondrial DNA and present in the amplified mitochondrial DNA, under conditions and for a time sufficient to allow hybridization of the primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from the first product, and therefrom quantifying the extramitochondrial DNA and the mitochondrial DNA.

In another embodiment of this aspect of the invention the biological sample is treated by heating it in water to lyse cells contained in the sample, and then extracting cellular DNA from the lysed cells using an aqueous DNA extraction procedure. In certain embodiments of the invention the sample comprises a crude buffy coat fraction of whole blood. In certain other embodiments of the invention, the method further comprises the step of determining the ApoE genotype of the first subject and correlating said genotype with the risk or presence of disease. In some embodiments of the invention, the disease associated with altered mitochondrial function may be Alzheimer's Disease, Huntington's Disease, Parkinson's Disease, dystonia, schizophrenia, non-insulin dependent diabetes mellitus, mitochondrial encephalopathy, lactic acidosis, and stroke, myoclonic epilepsy ragged red fiber syndrome, and Leber's hereditary optic neuropathy.

Another aspect of the invention provides a method for quantifying extramitochondrial DNA, comprising: contacting a sample containing extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization of the primer to the extramitochondrial DNA, and therefrom quantifying the extramitochondrial DNA.

It is another aspect of the invention to provide a method for quantifying extramitochondrial DNA, comprising: contacting a sample containing extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization and extension of the primer to the extramitochondrial DNA to produce a product, and therefrom quantifying the extramitochondrial DNA.

Another aspect of the invention provides a method for quantifying extramitochondrial DNA, comprising: contacting a sample containing amplified extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization of the primer to the extramitochondrial DNA, therefrom quantifying the extramitochondrial DNA.

In yet another aspect of the invention, a method is provided for quantifying extramitochondrial DNA by contacting a sample containing amplified extramitochondrial DNA with an oligonucleotide primer having a nucleotide sequence complementary to at least a portion of the extramitochondrial DNA under conditions and for a time sufficient to allow hybridization of the primer to the extramitochondrial DNA; and detecting hybridization and extension of the primer to the extramitochondrial DNA to produce a product, and therefrom quantifying the extramitochondrial DNA.

In one embodiment the extramitochondrial DNA is amplified by polymerase chain reaction, transcriptional amplification systems or self-sustained sequence replication. In certain embodiments of the various aspects of the invention, a single oligonucleotide primer is used. In certain embodiments of the invention a primer extension assay is used. In certain embodiments of the invention, the step of detecting may be by polymerase chain reaction, primer extension assay, ligase chain reaction or restriction fragment length polymorphism analysis.

In certain embodiments of the invention, the ratio r for a biological sample is calculated by determining the presence in the sample of a nucleotide sequence that may be SEQ ID NO:1, a portion of SEQ ID NO:1, SEQ ID NO:3 or a portion of SEQ ID NO:3. In one embodiment the portion of the nucleotide sequence of SEQ ID NO:1 corresponds to a portion of the nucleotide sequence of SEQ ID NO:2 encoding a mitochondrial cytochrome c oxidase. In another embodiment the portion of SEQ ID NO:1 corresponds to a portion of a mitochondrial cytochrome c oxidase encoding sequence that may be portion of a cytochrome c oxidase 1 (CO1) encoding sequence or a portion of a cytochrome c oxidase 2 (CO2) encoding sequence. In still other embodiments, the portion of the nucleotide sequence of SEQ ID NO:1 corresponds to a portion of the nucleotide sequence of SEQ ID NO:2 encoding a mitochondrial ATP synthetase subunit. In other embodiments, the portion of SEQ ID NO:1 corresponds to a portion of a mitochondrial ATP synthetase subunit encoding sequence that may be a portion of a sequence encoding ATP synthetase subunit 6 or a portion of a sequence encoding ATP synthetase subunit 8.

In some embodiments the nucleotide sequence of SEQ ID NO:1 corresponds to a portion of SEQ ID NO:2 that may be a portion of a sequence encoding ND1, a sequence encoding a portion of ND2 or a sequence encoding a portion of CO3. In other embodiments, the portion of the nucleotide sequence of SEQ ID NO:3 corresponds to a portion of the nucleotide sequence of SEQ ID NO:2 encoding a mitochondrial ATP synthetase subunit, which in some embodiments may further be a portion of a sequence encoding ATP synthetase subunit 6 or a portion of a sequence encoding ATP synthetase subunit 8. In still other embodiments, the nucleotide sequence of SEQ ID NO:1 corresponds to a portion of the nucleotide sequence of SEQ ID NO:2 encoding a mitochondrial tRNA, while in yet other embodiments the portion of the nucleotide sequence of SEQ ID NO:3 corresponds to a portion of the nucleotide sequence of SEQ ID NO:2 encoding a mitochondrial tRNA.

In another aspect the invention provides an isolated nucleic acid comprising all or a portion of the nucleotide sequence of SEQ ID NO:1 or a complementary sequence thereto. In another aspect the invention provides an isolated nucleic acid comprising all or a portion of a nucleotide sequence of SEQ ID NO:1 or a complementary sequence thereto, wherein the sequence of the isolated nucleic acid differs by at least one nucleotide from the corresponding sequence of a nucleic acid comprising the nucleotide sequence of SEQ ID NO:2 or a complementary sequence thereto. In another aspect the invention provides an isolated nucleic acid comprising all or a portion of the nucleotide sequence of SEQ ID NO:3 or a complementary sequence thereto. In another aspect the invention provides an isolated nucleic acid comprising all or a portion of a nucleotide sequence of SEQ ID NO:3 or a complementary sequence thereto, wherein the sequence of the isolated nucleic acid differs by at least one nucleotide from the corresponding sequence of a nucleic acid comprising the nucleotide sequence of SEQ ID NO:2 or a complementary sequence thereto.

In another aspect the invention provides a method for determining the risk or presence of a disease associated with altered mitochondrial function in a subject suspected of having or being at risk for having such a disease, by quantifying the amount of extramitochondrial DNA and the amount of mitochondrial DNA in a biological sample from the subject, and therefrom determining the risk or presence of the disease. It is another aspect of the invention to provide a method for determining the risk or presence of a disease associated with altered mitochondrial function in a first subject suspected of having or being at risk for having such a disease, by comparing the amount of extramitochondrial DNA and the amount of mitochondrial DNA in a biological sample from the first subject to the amount of extramitochondrial DNA and the amount of mitochondrial DNA in a biological sample from a second subject, and therefrom determining the risk or presence of the disease. In another aspect the invention provides a method for determining the risk or presence of a disease associated with altered mitochondrial function in a first subject suspected of having or being at risk for having such a disease, by quantifying the amount of extramitochondrial DNA and the amount of mitochondrial DNA in a biological sample from the subject and comparing the amount of extramitochondrial DNA and the amount of mitochondrial DNA to the amount of extramitochondrial DNA and the amount of mitochondrial DNA in a biological sample from a second subject known to be free of a risk or presence of a disease associated with altered mitochondrial function, and therefrom determining the risk or presence of the disease.

Another aspect of the invention provides a method of regulating a telomere by administering to a subject a nucleic acid molecule comprising all or a portion of SEQ ID NO:1 or a complementary portion thereto. In one embodiment, the administered nucleic acid molecule comprises an exmtDNA sequence. In another aspect, the invention provides a method of regulating a telomere by administering to a subject a nucleic acid molecule comprising all or a portion of SEQ ID NO:3 or a complementary portion thereto.

These and other aspects of the present invention will become evident upon reference to the following detailed description and attached drawings. In addition, various references are set forth herein which describe in more detail certain aspects of this invention, and are therefore incorporated by reference in their entirety.

BRIEF DESCRIPTION OF THE DRAWINGS

FIG. 1 depicts the nucleotide sequence of SEQ ID NO:1.

FIG. 2 depicts the nucleotide sequence of SEQ ID NO:2 and amino acid sequences of SEQ ID NOs: 13–25.

FIG. 3 depicts the nucleotide sequence of SEQ ID NO:3 and human mtDNA sequence of SEQ ID NO:26.

DETAILED DESCRIPTION OF THE INVENTION

The present invention is directed generally to compositions and methods for diagnosing the risk or presence of a disease associated with altered mitochondrial function in a subject, and to compositions and methods for the identification of agents that may be suitable for treating a disease associated with altered mitochondrial function. The invention utilizes a ratio, r, that may be useful for pharmacogenomic purposes, for example to stratify patient populations according to the suitability of particular therapeutic agents for use in such populations. The ratio r is the ratio of the amount of exmtDNA in a biological sample relative to the sum of the amount of exmtDNA plus mtDNA in the sample. As expressed quantitatively, the ratio r may be calculated using the formula:

$$r=x/(x+y)$$

wherein x is the amount of exmtDNA in a sample, and y is the amount of mtDNA in the sample.

In various aspects of the invention, as elaborated more fully herein, quantification of x and y provide, through calculation of r, parameters useful in diagnosis of a disease associated with altered mitochondrial function and in screening assays for agents that may be suitable for the treatment of such a disease.

As discussed above, "altered mitochondrial function" may refer to any condition or state, including those that accompany a disease, where any structure or activity that is directly or indirectly related to a mitochondrial function has been changed. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Also as discussed above, altered mitochondrial function may include (but need not be limited to) altered respiratory or metabolic activity in some or all cells of a biological source. For example, markedly impaired ETC activity may be an example of altered mitochondrial function, as may be generation of increased ROS or defective oxidative phosphorylation. As further examples, altered mitochondrial membrane potential, induction of apoptotic pathways and formation of atypical chemical and biochemical crosslinked species within a cell, whether by enzymatic or non-enzymatic mechanisms, may all be regarded as indicative of altered mitochondrial function. Without wishing to be bound by theory, alterations in the ratio r are believed to reflect chemical changes within affected cells that quantitatively influence recoveries of exmtDNA and/or mtDNA. For example, biochemical crosslinking events may result in the formation of DNA aggregates, DNA adducts or other molecular species that affect DNA recoveries following extraction procedures.

According to the present invention, alterations in the ratio r as defined above provide a novel and useful parameter for diagnosing the risk or presence of a disease associated with altered mitochondrial function in a subject, and for identifying agents that may be suitable for treating a disease associated with altered mitochondrial function. As discussed above, a number of diseases, including several degenerative diseases, are associated with alterations in mitochondrial function. Further, detection of an appropriate parameter of altered mitochondrial function can provide preclinical evidence for a risk of or predisposition to a disease.

Determination of the ratio r involves quantification of exmtDNA (x) and mtDNA (y) that may be based on strong but not necessarily absolute nucleotide sequence conservation when corresponding portions of mtDNA and exmtDNA are compared, as discussed herein. In most preferred embodiments of the invention, determination of r is accomplished by detecting minor nucleotide sequence differences in highly conserved mtDNA and exmtDNA regions, as elaborated below. The invention provides compositions and methods that include the use of nucleic acid molecules, or portions thereof, having nucleotide sequences that are found in the human mtDNA sequence SEQ ID NO:2 (Anderson et al., *Nature* 290:457, 1981) and fragments of SEQ ID NO:2 that are suitable for use as oligonucleotide primers in nucleic acid primer extension or amplification techniques, as hybridization probes for the detection of complementary nucleotide sequences in a sample or for any number of additional uses that are well known to those familiar with the art. ExmtDNA may be nuclear DNA, including chromosomal and non-chromosomal DNA, or non-nuclear extramitochondrial DNA that may be from any subcellular compartment, provided it is not mtDNA.

Nucleic acid sequences within the scope of the invention include isolated DNA and RNA sequences that specifically hybridize under conditions of moderate or high stringency to exmtDNA nucleotide sequences, including exmtDNA sequences disclosed herein or fragments thereof, and their complements. As used herein, conditions of moderate stringency, as known to those having ordinary skill in the art, and as defined by Sambrook et al., *Molecular Cloning: A Laboratory Manual,* 2nd Ed. Vol. 1, pp. 1.101–104, Cold Spring Harbor Laboratory Press (1989), include use of a prewashing solution for the nitrocellulose filters 5×SSC, 0.5% SDS, 1.0 mM EDTA (pH 8.0), hybridization conditions of 50% formamide, 6×SSC at 42° C. (or other similar hybridization solution), and washing conditions of about 50–60° C., 0.5×SSC, 0.1% SDS. Conditions of high stringency are defined as hybridization conditions as above, and with washing at 60–68° C., 0.2×SSC, 0.1% SDS. In other embodiments, hybridization to an exmtDNA nucleotide sequence may be at normal stringency, which is approximately 25–30° C. below Tm of the native duplex (e.g., 5×SSPE, 0.5% SDS, 5×Denhardt's solution, 50% formamide, at 42° C. or equivalent conditions), at low stringency hybridizations, which utilize conditions approximately 40° C. below Tm, or at high stringency hybridizations, which utilize conditions approximately 10° C. below Tm. The skilled artisan will recognize that the temperature, salt concentration, and chaotrope composition of hybridization and wash solutions may be adjusted as necessary according to factors such as the length and nucleotide base composition of the probe. (See also, e.g., Ausubel et al., *Current Protocols in Molecular Biology,* Greene Publishing, 1987.)

An "isolated nucleic acid molecule" refers to a polynucleotide molecule in the form of a separate fragment or as a component of a larger nucleic acid construct, that has been separated from its source cell (including the chromosome it normally resides in) at least once, preferably in a substantially pure form. Isolated nucleic acids may be nucleic acids having particular disclosed nucleotide sequences or may be regions, portions or fragments thereof. Those having ordinary skill in the art are able to prepare isolated nucleic acids having the complete nucleotide sequence, or the sequence of any portion of a particular isolated nucleic acid molecule, when provided with the appropriate nucleic acid sequence information as disclosed herein. Nucleic acid molecules may be comprised of a wide variety of nucleotides, including DNA, RNA, nucleotide analogues such as phosphorothioates or peptide nucleic acids, or other analogues with which those skilled in the art will be familiar, or some combination of these.

The present invention, as described herein, provides exmtDNA sequences and isolated exmtDNA nucleic acid molecules. exmtDNA may be isolated from genomic DNA, typically by first generating an appropriate DNA library through techniques for constructing libraries that are known in the art (see Sambrook et al., *Molecular Cloning: A Laboratory Manual,* Cold Spring Harbor Press, 1989) or purchased from commercial sources (e.g., Clontech, Palo Alto, Calif.). Briefly, genomic DNA libraries can be constructed in chromosomal vectors, such as YACs (yeast artificial chromosomes), bacteriophage vectors, such as pBeloBAC11, λEMBL3, λgt10, cosmids, or plasmids. Alternatively, isolated exmtDNA may be prepared by preferentially amplifying exmtDNA sequences present in biological samples using, for example, DNA amplification methodologies such as PCR or other amplification techniques that are well known in the art, with suitable oligonucleotide primers complementary to exmtDNA sequences as disclosed herein.

In one embodiment, known mtDNA sequences derived from SEQ ID NO:2 (Anderson et al., *Nature* 290:457, 1981) may be utilized to design oligonucleotide hybridization probes suitable for screening genomic libraries. Preferably, such oligonucleotide probes are 18–30 bases in length and have sequences that, under the hybridization conditions selected, hybridize to complementary exmtDNA sequences lacking nucleotide substitutions, insertions or deletions ("mutations") relative to the corresponding region of the mtDNA sequence of SEQ ID NO:2.

Portions of an exmtDNA sequence and the mtDNA sequence of SEQ ID NO:2 are regarded as "corresponding" nucleic acid sequences, regions, fragments or the like, based on the convention for numbering mtDNA nucleic acid positions according to SEQ ID NO:2 (Anderson et al., *Nature* 290:457, 1981), wherein an exmtDNA sequence is aligned with the mtDNA sequence of SEQ ID NO:2 such that at least 70%, preferably at least 80% and more preferably at least 90% of the nucleotides in a given sequence of at least 20 consecutive nt's of a sequence are identical. In certain preferred embodiments, an exmtDNA sequence is greater than 95% identical to a corresponding mtDNA sequence. In certain particularly preferred embodiments, an exmtDNA sequence is identical to a corresponding mtDNA sequence. Those oligonucleotide probes having sequences that are identical in corresponding regions of mtDNA and exmtDNA may be identified and selected following hybridization target DNA sequence analysis, to verify the absence of mutations in the target exmtDNA sequence relative to the primer mtDNA-derived sequence.

To facilitate hybridization detection, the oligonucleotide may be conveniently labeled, generally at the 5' end, with a reporter molecule, such as a radionuclide, e.g., $^{32}$P, enzymatic label, protein label, fluorescent label, biotin or other suitable labeling moieties known in the art. Such libraries are then generally plated as phage or colonies, depending upon the vector used. Subsequently, a plate replica to which the colonies or phage have been transferred, such as a nitrocellulose or nylon membrane or the like, is probed to identify candidate clones that contain the exmtDNA sequence. Such candidates may be verified as containing exmtDNA by any of various means including, for example, DNA sequence analysis or hybridization with a second, non-overlapping probe selected as described above to hybridize with target exmtDNA sequences lacking nucleotide substitutions, deletions or insertions relative to the corresponding portion of the mtDNA sequence of SEQ ID NO:2.

Once a library is identified as containing exmtDNA, the exmtDNA can be isolated by amplification. Briefly, when using genomic library DNA as a template, amplification primers are designed based upon known mtDNA sequences (SEQ ID NO:2) and primer "walking" is used to select primers that anneal to exmtDNA regions that are identical to mtDNA sequences. The primers preferably have a GC content of about 50% and contain restriction sites to facilitate cloning. Primers do not have self-complementary sequences, nor do they contain complementary sequences at their 3' end (to prevent primer-dimer formation). The primers are annealed to genomic DNA and sufficient amplification cycles are performed to yield a product readily visualized by gel electrophoresis and staining. The amplified fragment is purified and inserted into a vector, such as λgt10 or pBS(M13+), and propagated. Confirmation of the nature of the fragment is obtained by DNA sequence analysis.

As an example of detection of mtDNA-like sequences in a DNA library, an oligonucleotide having a nucleotide sequence present in a portion of any human mtDNA gene, preferably one of the human mtDNA encoded genes NADH dehydrogenase subunit 1 (ND1), NADH dehydrogenase subunit 2 (ND2) or cytochrome c oxidase 3 (CO3) and more preferably one of the human mtDNA encoded genes CO, CO2, ATPase 8 or ATPase 6, may be labeled and used as a probe on a human genomic DNA library. An initial hybridization at normal stringency may yield candidate clones or fragments. If no hybridization is initially observed, varying degrees of stringency may be used. (See Sambrook et al., Ausubel et al., supra, and other well-known sources for stringency conditions.)

Where it is advantageous to use oligonucleotide primers according to the present invention, such primers may be 10–60 nucleotides in length, preferably 15–35 nucleotides and still more preferably 18–30 nucleotides in length. Primers as described above for use in isolating exmtDNA from genomic DNA may also be useful in the present invention for quantifying mtDNA and exmtDNA by any of a variety of techniques well known in the art for determining the amount of specific nucleic acid target sequences present in a sample based on specific hybridization of a primer to the target sequence. Optionally, in certain of these techniques, hybridization precedes nucleotide polymerase catalyzed extension of the primer using the strand containing the target sequence as a template, and/or ligation of oligonucleotides hybridized to adjacent target sequences, and embodiments of the invention using primer extension are particularly preferred. For examples of references on such quantitative detection techniques, including those that may be used to detect nucleotide insertions, substitutions or deletions in a portion of an exmtDNA sequence site near an oligonucleotide primer target hybridization site that corresponds to a portion of the mtDNA sequence of SEQ ID NO:2, and further including those that involve primer extension, see U.S. Pat. No. 5,760,205 and the references cited therein, all of which are hereby incorporated by reference, and see also, for example, Botstein et al. (*Am. J. Hum. Gen.* 32:314, 1980), Gibbs et al. (*Nucl. Ac. Res.* 17:2437, 1989), Newton et al. (*Nucl. Ac. Res.* 17:2503, 1989), Grossman et al. (*Nucl. Ac. Res.* 22:4527, 1994), and Saiki et al. (*Proc. Nat. Acad. Sci.* 86:6230, 1989), all of which are hereby incorporated by reference. A particularly useful method for this purpose is the primer extension assay disclosed by Fahy et al. (*Nucl. Acids Res.* 25:3102, 1997) and by Ghosh et al. (*Am. J. Hum. Genet.* 58:325, 1996), both of which references are hereby incorporated in their entireties, as is Krook et al. (*Hum. Molec. Genet.* 1:391, 1995) which teaches modification of primer extension reactions to detect multiple nucleotide substitutions, insertions, deletions or other mutations. Other examples of useful techniques for quantifying the presence of specific nucleic acid target sequences in a sample include but need not be limited to labeled probe hybridization to the target nucleic acid sequences with or without first partially separating target nucleic acids from other nucleic acids present in the sample.

Examples of other useful techniques for determining the amount of specific nucleic acid target sequences present in a sample based on specific hybridization of a primer to the target sequence include specific amplification of target nucleic acid sequences and quantification of amplification products, including but not limited to polymerase chain reaction (PCR, Gibbs et al., *Nucl. Ac. Res.* 17:2437, 1989), transcriptional amplification systems, strand displacement amplification and self-sustained sequence replication (3SR, Ghosh et al, in Molecular Methods for Virus Detection, 1995 Academic Press, NY, pp. 287–314), the cited references for which are hereby incorporated in their entireties. Examples of other useful techniques include ligase chain reaction, single stranded conformational polymorphism analysis, Q-beta replicase assay, restriction fragment length polymorphism (RFLP, Botstein et al., *Am. J. Hum. Gen.* 32:314, 1980) analysis and cycled probe technology, as well as other suitable methods that will be known to those familiar with the art.

In a particularly preferred embodiment of the invention, primer extension is used to quantify exmtDNA and mtDNA present in a biological sample. (Ghosh et al., *Am. J. Hum. Genet.* 58:325, 1996) This embodiment may offer certain advantages by permitting both exmtDNA and mtDNA to be simultaneously quantified using a single oligonucleotide primer capable of hybridizing to a complementary nucleic acid target sequence that is present in a defined region of mtDNA and in a corresponding region of a exmtDNA sequence. Without wishing to be bound by theory, the use of a single primer for quantification of exmtDNA and of mtDNA is believed to avoid uncertainties associated with potential disparities in the relative hybridization properties of multiple primers and may offer other advantages. Where such a target sequence is situated adjacent to an exmtDNA nucleotide sequence position that is a nucleotide substitution, insertion or deletion relative to the corresponding mtDNA sequence position, primer extension assays may be designed such that oligonucleotide extension products of primers hybridizing to mtDNA are of different lengths than oligonucleotide extension products of primers hybridizing to exmtDNA. Accordingly, the amount of exmtDNA in a sample and the amount of mtDNA in the sample may be determined by quantification of distinct extension products that are separable on the basis of sequence length or molecular mass, for purposes of calculating the ratio r as described above.

Sequence length or molecular mass of primer extension assay products may be determined using any known method for characterizing the size of nucleic acid sequences with which those skilled in the art are familiar. In a preferred embodiment, primer extension products are characterized by gel electrophoresis. In another preferred embodiment, primer extension products are characterized by mass spectrometry (MS), which may further include matrix assisted laser desorption ionization/time of flight (MALDI-TOF) analysis or other MS techniques known to those having skill in the art. See, for example, U.S. Pat. Nos. 5,622,824, 5,605,798 and 5,547,835, all of which are hereby incorporated by reference in their entireties. In another preferred embodiment, primer extension products are characterized by liquid or gas chromatography, which may further include high performance liquid chromatography (HPLC), gas chromatography-mass spectrometry (GC-MS) or other well known chromatographic methodologies.

Any exmtDNA sequence or portion of an exmtDNA sequence that corresponds to the human mtDNA sequence of SEQ ID NO:2 or a portion thereof or several portions thereof may be useful in this embodiment of the invention. Examples of human exmtDNA sequences that are useful in this and other embodiments of the invention are disclosed in SEQ ID NO:1 and in SEQ ID NO:3. Nucleotide positions at which exmtDNA and mtDNA differ are provided in Table 1 and Table 2, in which the identities of nucleotides at particular sequence positions in SEQ ID NO:2 and the corresponding positions in SEQ ID NO:1 and SEQ ID NO:3, respectively, are presented. Portions of SEQ ID NO:2 that include nucleic acid sequences encoding the mitochondrial ETC enzymes cytochrome c oxidase 1 (CO 1), cytochrome c oxidase 2 (CO 2), ATP synthetase subunit 8 (ATPase 8) and ATP synthetase subunit 6 (ATPase 6) may be particularly useful, and in preferred embodiments of the invention these sequences comprise isolated nucleic acid molecules that have nucleotide sequences identical or complementary to corresponding nucleic acid sequences present in exmtDNA of SEQ ID NO:1 and/or SEQ ID NO:3. Portions of SEQ ID NO:2 that include nucleid acid sequences encoding the mitochondrial tRNAs, including mitochondrial isoleucyl, glutaminyl, methionyl, aspartyl, cysteinyl, tyrosinyl and lysyl tRNAs may also be particularly useful, and in preferred embodiments of the invention these sequences comprise isolated nucleic acid molecules that have nucleotide sequences identical or complementary to corresponding nucleic acid sequences present in exmtDNA of SEQ ID NO:1 and/or SEQ ID NO:3.

TABLE 1

| mt Gene Region | Nucleotide position | Human mtDNA SEQ ID NO:2 | Human exmtDNA SEQ ID NO:1 |
|---|---|---|---|
| NDI | 4048 | G | A |
|  | 4104 | A | G |
| tRNA$^{Ile}$ | 4312 | C | T |
|  | 4318 | C | T |
| tRNA$^{Gln}$ | 4375 | C | G |
|  | 4382 | C | A |
|  | 4398 | C | T |
| tRNA$^{Met}$ | 4456 | C | T |
| ND2 | 4496 | C | T |
|  | 4736 | T | C |
|  | 4769 | A | G |
|  | 4856 | T | C |
|  | 4904 | C | T |
|  | 4914 | C | T |
|  | 4940 | C | T |
|  | 4958 | A | G |
|  | 4985 | G | A |
|  | 4991 | G | A |
|  | 5041 | T | C |
|  | 5147 | G | A |
|  | 5320 | C | T |
|  | 5351 | A | G |
|  | 5387 | C | T |
|  | 5426 | T | C |
|  | 5471 | G | A |
|  | 5474 | A | G |
|  | 5498 | A | G |
| tRNA$^{Cys}$ | 5821 | G | A |
| tRNA$^{Tyr}$ | 5840 | C | T |
| CO1 | 6023 | G | A |
|  | 6221 | T | C |
|  | 6242 | C | T |
|  | 6266 | A | C |
|  | 6299 | A | G |
|  | 6366 | G | A |
|  | 6383 | G | A |
|  | 6410 | C | T |
|  | 6452 | C | T |
|  | 6483 | C | T |
|  | 6512 | T | C |
|  | 6542 | C | T |
|  | 6569 | C | A |
|  | 6641 | T | C |
|  | 6935 | C | T |
|  | 6938 | C | T |
|  | 7146 | A | G |
|  | 7232 | C | T |
|  | 7256 | C | T |
|  | 7316 | G | A |
| tRNA$^{Asp}$ | 7521 | G | A |
| CO2 | 7650 | C | T |
|  | 7705 | T | C |
|  | 7810 | C | T |
|  | 7868 | C | T |
|  | 7891 | C | T |

TABLE 1-continued

| mt Gene Region | Nucleotide position | Human mtDNA SEQ ID NO:2 | Human exmtDNA SEQ ID NO:1 |
|---|---|---|---|
|  | 7912 | G | A |
|  | 8021 | A | G |
|  | 8065 | G | A |
|  | 8140 | C | T |
|  | 8152 | G | A |
|  | 8167 | T | C |
|  | 8196–8197 | AC | deletion |
|  | 8203 | C | T |
| ATPase8 | 8392 | G | A |
|  | 8455 | C | T |
|  | 8461 | C | T |
|  | 8503 | T | C |
|  | 8545 | G | A |
| ATPase6 | 8545 | G | A |
|  | 8655 | C | T |
|  | 8677 | A | C |
|  | 8701 | A | G |
|  | 8718 | A | G |
|  | 8860 | A | G |
|  | 8943 | C | T |
|  | 9060 | C | A |
|  | 9075 | C | T |
|  | 9103 | C | T |
|  | 9168 | C | T |
|  | 9175 | C | T |
| CO3 | 9254 | A | G |
|  | 9325 | T | C |
|  | 9329 | G | C |
|  | 9335 | C | T |
|  | 9434 | A | G |
|  | 9540 | T | C |
|  | 9545 | A | G |
|  | 9548 | G | A |
|  | 9559 | G | C |
|  | 9629 | A | G |

TABLE 2

| mt Gene Region | Nucleotide position | Human mtDNA SEQ ID NO:2 | Human exmtDNA SEQ ID NO:3 |
|---|---|---|---|
| tRNA$^{Lys}$ | 8310 | T | C |
|  | 8311 | T | C |
|  | 8336 | T | C |
|  | 8345 | C | T |
|  | 8348 | A | T |
|  | 8349 | C | T |
|  | 8351 | C | T |
| ATPase8 | 8371 | C | A |
|  | 8374 | A | G |
|  | 8383 | T | C |
|  | 8386 | C | T |
|  | 8392 | G | A |
|  | 8395 | C | T |
|  | 8396 | A | G |
|  | 8398 | C | T |
|  | 8401 | A | C |
|  | 8404 | T | C |
|  | 8410 | C | A |
|  | 8419 | T | C |
|  | 8422 | A | G |
|  | 8423 | C | T |
|  | 8428 | C | T |
|  | 8450 | T | C |
|  | 8459 | A | C |
|  | 8463 | A | G |
|  | 8467 | C | T |
|  | 8470 | A | G |
|  | 8473 | T | C |
|  | 8474 | C | A |
|  | 8485 | G | A |
|  | 8486 | C | T |

TABLE 2-continued

| mt Gene Region | Nucleotide position | Human mtDNA SEQ ID NO:2 | Human exmtDNA SEQ ID NO:3 |
|---|---|---|---|
| | 8487 | C | T |
| | 8488 | C | T |
| | 8491 | A | T |
| | 8503 | T | C |
| | 8506 | T | C |
| | 8508 | A | G |
| | 8509 | C | T |
| | 8512 | A | G |
| | 8539 | C | T |
| ATPase8/6 | 8541 | G | A |
| | 8557 | G | A |
| | 8562 | C | T |
| | 8566 | A | G |
| | 8568 | C | A |
| ATPase6 | 8584 | G | A |
| | 8591 | T | C |
| | 8592 | G | A |
| | 8598 | T | C |
| | 8610 | T | C |
| | 8611 | C | T |
| | 8614 | T | C |
| | 8617 | A | G |
| | 8622 | C | A |
| | 8634 | T | C |
| | 8661 | C | T |
| | 8674 | A | C |
| | 8676 | C | T |
| | 8677 | A | C |
| | 8682 | A | C |
| | 8687 | C | T |
| | 8697 | G | A |
| | 8703 | C | G |
| | 8709 | C | T |
| | 8714 | C | T |
| | 8718 | A | G |
| | 8730 | A | G |
| | 8733 | T | C |
| | 8743 | G | A |
| | 8745 | A | T |
| | 8749 | T | C |
| | 8751 | A | G |
| | 8754 | C | T |
| | 8775 | C | T |
| | 8788 | C | T |
| | 8793 | T | C |
| | 8810 | C | T |

In another particularly preferred embodiment of the invention, DNA in a biological sample containing exmtDNA and/or mtDNA is first amplified by methodologies well known in the art and described above, such that the amplification products may be used as templates in a method for quantifying the amount of exmtDNA and mtDNA present in the sample. Accordingly, it may be desirable to employ oligonucleotide primers that are complementary to target sequences that are identical in, and common to, mtDNA and exmtDNA, for example PCR amplification templates and primers prepared according to Fahy et al. (*Nucl. Acids Res.*, 25:3102, 1997) and Davis et al. (*Proc. Nat. Acad. Sci. USA* 94:4526, 1997; see also Hirano et al., *Proc. Nat. Acad. Sci. USA*. 94:14894, 1997, and Wallace et al., Proc. Nat. Acad. Sci. USA 94:14900, 1997.)

Biological samples containing exmtDNA and mtDNA may comprise any tissue or cell preparation in which exmtDNA and mtDNA may be present. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromasomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. In certain preferred embodiments of the invention, the subject or biological source may be suspected of having or being at risk for having a disease associated with altered mitochondrial function, and in certain preferred embodiments of the invention the subject or biological source may be known to be free of a risk or presence of such as disease.

In certain other preferred embodiments where it is desirable to determine whether or not a subject or biological source falls within clinical parameters indicative of Alzheimer's disease (AD), signs and symptoms of AD that are accepted by those skilled in the art may be used to so designate a subject or biological source, for example clinical signs referred to in McKhann et al. (*Neurology* 34:939, 1984, National Institute of Neurology, Communicative Disorders and Stroke and Alzheimer's Disease and Related Disorders Association Criteria of Probable AD, NINCDS-ADRDA) and references cited therein, or other means known in the art for diagnosing AD.

In certain aspects of the invention, biological samples containing mtDNA and exmtDNA may be obtained from the subject or biological source before and after contacting the subject or biological source with a candidate agent, for example to identify a candidate agent capable of effecting a change in the value of the ratio r, defined above, relative to the value of r before exposure of the subject or biological source to the agent.

In a most preferred embodiment of the invention, the biological sample containing mtDNA and exmtDNA may comprise a crude buffy coat fraction of whole blood, which is known in the art to comprise further a particulate fraction of whole blood enriched in white blood cells and platelets and substantially depleted of erythrocytes. Those familiar with the art will know how to prepare such a buffy coat fraction, which may be prepared by differential density sedimentation of blood components under defined conditions, including the use of density dependent separation media, or by other methods.

In another most preferred embodiment of the invention, the amount of exmtDNA and mtDNA in a biological sample may be quantified by first heating the sample in water to lyse cells contained therein, and then extracting cellular DNA from the lysed cells using an aqueous DNA extraction procedure. "Heating" may involve treating the cells for various times, typically 1–120 minutes, at a high temperature that is at least 80° C., preferably at least 90° C., more preferably at least 95° C. and most preferably in a boiling water bath. Based on the compositions and methods disclosed in the present application, the ordinarily skilled artisan will be able to readily determine optimal times and temperatures for heating samples to practice the invention without undue experimentation. As used herein, an "aqueous DNA extraction" method refers to preparation of DNA from such a boiled cell lysate without subjecting the lysate to sodium dodecylsulfate(SDS)/proteinase K treatments and/or without fractionating the lysate using a phenol-chloroform two-phase separation extraction step. Those skilled in the art will be familiar with various standard procedures for preparing and handling DNA without the use of SDS/ proteinase K and/or phenol-chloroform.

According to certain embodiments of the invention, the particular cell type or tissue type from which a biological sample is obtained may influence qualitative or quantitative aspects of the exmtDNA and/or mtDNA contained therein relative to exmtDNA and/or mtDNA obtained from distinct cell or tissue types of a common biological source. As described above, some diseases associated with altered mitochondrial function may manifest themselves in particular cell or tissue types. For example, AD is primarily a neurodegenerative disease that particularly effects changes in the central nervous system (CNS). It is therefore within the contemplation of the invention to quantify exmtDNA and mtDNA in biological samples from different cell or tissue types as may render the advantages of the invention most useful for a particular disease associated with altered mitochondrial function, and the relevant cell or tissue types will be known to those familiar with such diseases.

In order to determine whether a mitochondrial alteration may contribute to a particular disease state, it may be useful to construct a model system for diagnostic tests and for screening candidate therapeutic agents in which the nuclear genetic background may be held constant while the mitochondrial genome is modified. It is known in the art to deplete mitochondrial DNA from cultured cells to produce $\rho^0$ cells, thereby preventing expression and replication of mitochondrial genes and inactivating mitochondrial function. See, for example, International Publication Number WO 95/26973, which is hereby incorporated by reference in its entirety, and references cited therein. It is further known in the art to repopulate such $\rho^0$ cells with mitochondria derived from foreign cells in order to assess the contribution of the donor mitochondrial genotype to the respiratory phenotype of the recipient cells. Such cytoplasmic hybrid cells, containing genomic and mitochondrial DNAs of differing biological origins, are known as cybrids.

"$\rho^0$ cells" are cells essentially completely depleted of mtDNA, and therefore have no functional mitochondrial respiration/electron transport activity. Such absence of mitochondrial respiration may be established by demonstrating a lack of oxygen consumption by intact cells in the absence of glucose, and/or by demonstrating a lack of catalytic activity of electron transport chain enzyme complexes having subunits encoded by mtDNA, using methods well known in the art. (See, e.g., Miller et al., *J. Neurochem.* 67:1897–1907, 1996.) That cells have become $\rho^0$ cells may be further established by demonstrating that no mtDNA sequences are detectable within the cells. For example, using standard techniques well known to those familiar with the art, cellular mtDNA content may be measured using slot blot analysis of 1 µg total cellular DNA probed with a mtDNA-specific oligonucleotide probe radiolabeled with, e.g., $^{32}$P to a specific activity $\geq$900 Ci/gm. Under these conditions $\rho^0$ cells yield no detectable hybridizing probe signal. Alternatively, any other method known in the art for detecting the presence of mtDNA in a sample may be used that provides comparable sensitivity.

"Mitochondrial DNA depleted" cells ("mtDNA depleted cells") are cells substantially but not completely depleted of functional mitochondria and/or mitochondrial DNA, by any method useful for this purpose. MtDNA depleted cells are preferably at least 80% depleted of mtDNA as measured using the slot blot assay described above for the determination of the presence of $\rho^0$ cells, and more preferably at least 90% depleted of mtDNA. Most preferably, mtDNA depleted cells are depleted of >95% of their mtDNA.

Mitochondria to be transferred to construct model systems in accordance with the present invention may be isolated from virtually any tissue or cell source. Cell cultures of all types may potentially be used, as may cells from any tissue. However, fibroblasts, brain tissue, myoblasts and platelets are preferred sources of donor mitochondria. Platelets are the most preferred, in part because of their ready abundance, and their lack of nuclear DNA. This preference is not meant to constitute a limitation on the range of cell types that may be used as donor sources.

For example, platelets may be isolated by an adaptation of the method of Chomyn (*Am. J. Hum. Genet.* 54:966–974, 1994). However, it is not necessary that this particular method be used. Other methods are easily substituted. For instance, if nucleated cells are used, cell enucleation and isolation of mitochondria isolation can be performed as described by Chomyn et al., *Mol. Cell. Biol.* 11:2236–2244, 1991. Human tissue from a subject suspected of having or being at risk for having a disease associated with altered mitochondrial function, or from a subject known to be free of a risk or presence of such a disease, may be the source of donor mitochondrial DNA.

After preparation of mitochondria by isolation of platelets or enucleation of donor cells, the mitochondria may be transplanted into $\rho^0$ cells or mtDNA depleted cells using any known technique for introducing an organelle into a recipient cell, including but not limited to polyethylene glycol (PEG) mediated cell membrane fusion, cell membrane permeabilization, cell-cytoplast fusion, virus mediated membrane fusion, liposome mediated fusion, particle mediated cellular uptake, microinjection or other methods known in the art. For example by way of illustration and not limitation, mitochondria donor cells (~1×10$^7$) are suspended in calcium-free Dulbecco's modified Eagle (DME) medium and mixed with $\rho^0$ cells (~0.5×10$^6$) in a total volume of 2 ml for 5 minutes at room temperature. The cell mixture is pelleted by centrifugation and resuspended in 150 µl PEG (PEG 1000, J.T. Baker, Inc., 50% w/v in DME). After 1.5 minutes, the cell suspension is diluted with normal $\rho^0$ cell medium containing pyruvate, uridine and glucose, and maintained in tissue culture plates. Medium is replenished daily, and after one week medium lacking pyruvate and uridine is used to inhibit growth of unfused $\rho^0$ cells. These or other methods known in the art may be employed to produce cytoplasmic hybrid, or "cybrid", cell lines.

As a non-limiting example, cybrid model systems may be useful for diagnosing a patient suspected of having or being at risk for a disease associated with altered mitochondrial function. According to this example, the patient's mitochondria are used to construct cybrid cells as described above. These cybrid cells may then be propagated in vitro and used to provide a biological sample for the determination of the ratio r, which can be compared to an r value calculated from samples of a control cybrid cell line constructed with mitochondria from a subject known to be free of disease. Where it may be desirable to compare the influence upon r of mitochondria from different sources, both cybrid cell lines may be constructed from the same $\rho^0$ cell line to provide a constant background environment. These and similar uses of model systems according to the invention for determining the risk for or presence of a disease associated with altered mitochondrial function will be appreciated by those familiar with the art and are within the scope and spirit of the invention.

As another non-limiting example, cybrid model systems may be useful for identifying agents suitable for treating a disease associated with altered mitochondrial function. According to this example, a cybrid cell line may be a biological source in which the ratio r is calculated as described above, before and after cybrid cells are contacted with a candidate agent for treating disease. Such a cybrid cell line may be used to screen candidate agents by identifying those agents capable of effecting a change in the value of r relative to the value of r before exposure to the agent. The present invention thus provides model systems for selecting therapeutic agents that may be suitable for the treatment of diseases associated with altered mitochondrial function. These and similar uses of model systems according to the invention for the screening and identification of agents that influence the ratio r defined above, will be appreciated by those familiar with the art and are within the scope and spirit of the invention.

In addition, although the present invention is directed primarily towards model systems for diseases in which the mitochondria have metabolic alterations, it is not so limited. Conceivably there are disorders wherein mitochondria contain structural or morphological defects or anomalies, and the model systems of the present invention are of value, for example, to find drugs that can address that particular aspect of the disease. Also, there are certain individuals that have or are suspected of having extraordinarily effective or efficient mitochondrial function, and the model systems of the present invention may be of value in studying such mitochondria. Moreover, it may be desirable to put known normal mitochondria into cell lines having disease characteristics, in order to rule out the possibility that mitochondrial alterations contribute to pathogenesis. All of these and similar uses are within the scope of the present invention, and the use of the phrase "mitochondrial alteration" herein should not be construed to exclude such embodiments.

According to the present invention, a ratio r as defined herein is determined in a biological sample, for example by calculation following quantification of mtDNA and exmtDNA using a technique based on specific oligonucleotide hybridization to a target sequence. This hybridization may be optionally followed by target template directed extension, such as in primer extension assays described herein. For certain diseases associated with altered mitochondrial function, calculation of r may have diagnostic usefulness. For example, where other clinical indicators of a disease associated with altered mitochondrial function are known, values for r in subjects known to be free of a risk or presence of such disease based on the absence of these indicators may be determined to establish a control range for r. The ratio may also be calculated in biological samples obtained from subjects suspected of having or being at risk for having a disease associated with altered mitochondrial function, and compared to the control range of r values determined in disease free subjects. Those having familiarity with the art will appreciate that there may be any number of variations on the particular subjects, biological sources and bases for comparing r values that are useful beyond those that are expressly presented herein, and these additional uses are within the scope and spirit of the invention.

For instance, determination of r in may take the form of a diagnostic assay performed on whole blood collected from a subject by routine venous blood draw, on buffy coat cells prepared from blood or on biological samples that are other cells, organs or tissue from a subject. Alternatively, in certain situations it may be desirable to construct cybrid cell lines using mitochondria from either control subjects or subjects suspected of being at risk for a disease associated with altered mitochondrial function. Such cybrids may be used to determine r for diagnostic purposes, or as biological sources for screening assays to identify agents that may be suitable for treating disease based on their ability to change the r value obtained from treated cells. In one embodiment of this aspect of the invention, therapeutic agents or combinations of agents that are tailored to effectively treat an individual patient's particular disease may be identified by routine screening of candidate agents on cybrid cells constructed with the patient's mitochondria.

The present invention provides compositions and methods that are useful in pharmacogenomics, for the classification and/or stratification of a subject or a patient population, for instance correlation of one or more traits in a subject with indicators of the responsiveness to, or efficacy of, a particular therapeutic treatment. In one aspect of the invention, measurement of r in a biological sample from a subject is combined with identification of the subject's apolipoprotein E (APOE) genotype to determine the risk for, or presence of, Alzheimer's disease (AD) in the subject. The apolipoprotein E type 4 allele (APOE-$\epsilon$4) allele is a genetic susceptibility factor for sporadic AD and confers a two fold risk for AD (Corder et al., Science 261:921, 1993; see also "National Institute on Aging/Alzheimer's Association Working Group Consensus Statement," Lancet 347:1091, 1996 and references cited therein, all of which are hereby incorporated by reference in their entireties.). Accordingly, in a preferred embodiment of the invention, the method for determining the risk for or presence of AD in a subject by comparing r values will further comprise determining the APOE genotype of the subject suspected of being at risk for AD. By using the combination of the methods for determining r, as disclosed herein, and methods known in the art for determining APOE genotype, an enhanced ability to detect the relative risk for AD is provided by the instant invention along with other related advantages. Similarly, where APOE genotype and risk for AD are correlated, the present invention provides advantageous methods for identifying agents suitable for treating AD where such agents affect r in a biological source.

As described herein, determination of r may be used to stratify an AD patient population. Accordingly, in another preferred embodiment of the invention, determination of r in a biological sample from an AD subject may provide a useful correlative indicator for that subject. An AD subject so classified on the basis of an r value may then be monitored using AD clinical parameters referred to above, such that correlation between r value and any particular clinical score used to evaluate AD may be monitored. For example, stratification of an AD patient population according to r values may provide a useful marker with which to correlate the efficacy of any candidate therapeutic agent being used in AD subjects. In a further preferred embodiment of this aspect of the invention, determination of r in concert with determination of an AD subject's APOE genotype may also be useful. These and related advantages will be appreciated by those familiar with the art.

In another aspect, the invention provides exmtDNA sequences that may be useful in the detection or regulation of telomeric events that are related to diseases, including diseases associated with altered mitochondrial function, or in the identification of agents that are suitable for the treatment of such diseases. Dynamic processes in the telomeric regions of chromosomes that involve specific nucleic acid sequences, and in particular that may involve particular nucleotide polymerase and nuclease activities, have been implicated in chromosomal events that may be related to cellular and molecular mechanisms of disease. See, for example, Fossel, J. Amer. Med. Assoc. 279:1732 (1998); LaBranche et al., Nat. Genet. 19:199 (1998); Shay, Cancer J. Sci. Am. 4:526 (1998); Nowak et al., Cancer J. Sci. Am. 4:148 (1998); Iwama et al., Hum. Genet. 102:397 (1998), all of which are hereby incorporated by reference. In one embodiment of the invention, nucleic acid sequences are provided that may be used to monitor telomeric events, including but not limited to telomerase activity. As disclosed herein, nucleic acids having exmtDNA sequences may be used to increase or decrease telomeric processes, for instance by destabilizing or stabilizing telomers. Without wishing to be bound by theory, because telomeric structure is related to cellular growth potential and/or senescence, nucleic acid based intervention in regulation of telomeric structure may provide effective means for the detection or treatment of related disease processes. The present invention provides identification of human exmtDNA sequences in human chromosomal telomeric regions, and other related advantages.

The following examples are offered by way of illustration, and not by way of limitation.

EXAMPLES

Example 1

Cloning of exmtDNA from Peripheral Blood Lymphocyte Genomic DNA Library

Peripheral blood lymphocytes were separated from the peripheral blood mononuclear cell fraction of freshly drawn venous blood from healthy human volunteers and the DNA extracted by standard techniques. Plasmid isolation, production of competent cells, transformation and manipulations using cloning vectors were performed essentially as described (Sambrook et al., *Molecular Cloning, a Laboratory Manual,* Cold Spring Harbor Laboratory Press, Cold Spring Harbor, N.Y., 1989). The human lymphocyte DNA was partially digested with HindIII and inserted into the pBeloBAC11 vector (Genome Systems, Inc., St. Louis, Mo. with insert sizes ranging from 50 kb to over 240 kb to create a human genomic library. This library was screened by PCR using the following primers, which are complementary to mtDNA sequences in the CO1 encoding region of SEQ ID NO:2 but have single-base substitutions at the 3' end. Details of PCR reaction conditions are provided in U.S. Pat. No. 5,565,323, which is hereby incorporated by reference, using 30 cycles instead of 25 cycles at 95° C. and with a single reaction being performed instead of five separate reactions.

| | |
|---|---|
| 5'-CCTTACACCTAGCAGGTA | SEQ ID NO:4 |
| 5'-ACGCCGATGAATATGATAGC | SEQ ID NO:5 |

A single positive clone was identified having a genomic DNA insert that included exmtDNA and was expanded, with the DNA then being purified using Magnum KB-100 columns (Genome Systems, St. Louis, Mo.). Portions of the insert were amplified with internal PCR primers complementary to human mtDNA sequences (Anderson et al., *Nature* 290:456, 1981) and sequenced using Prism DyeDeoxy terminator chemistry (Perkin-Elmer, Foster City, Calif.) according to the manufacturer's instructions. Sequence information at the junctions of exmtDNA and adjoining non-mtDNA in the positive pBeloBAC clone was obtained using the BigDye Terminator cycle sequencing kit (Perkin-Elmer) according to the supplier's recommendations. The products of sequencing reactions were purified by ethanol precipitation or by using CentriSep spin columns (Princeton Separations, Princeton, N.J.), then electrophoretically separated using an Applied Biosystems Model 373A DNA sequencing system (Applied Biosystems Division of Perkin-Elmer, Foster City, Calif.). Sequence Navigator software (Applied Biosystems) was used to analyze exmtDNA sequence data, and nucleotide insertions, deletions or substitutions were identified by comparing exmtDNA sequences to published human mtDNA sequence data. (SEQ ID NO:2, Anderson et al., *Nature* 290:456, 1981)

The insert contained the 5,844 base pair contiguous exmtDNA sequence of SEQ ID NO:1 (nucleotide positions 481–6337 in FIG. 1), which corresponded to and exhibited 98% sequence homology with nucleotide positions 3911–9755 of the human mtDNA sequence of SEQ ID NO:2. There were 89 nucleotide positions at which substitutions were detected, as indicated in Table 1. The complete ~5.8 kb exmtDNA sequence is in a single reading frame relative to the corresponding region of the human mitochondrial genome (SEQ ID NO:2) with the exception of a two base pair deletion at nucleotide positions 8196–8197. Starting at the 5' terminus (nt 481 in FIG. 1) and proceeding in the 3' direction, the exmtDNA sequence includes DNA sequences corresponding, in order, to a truncated ND1 gene, complete ND2 and CO1 genes, a CO2 gene with the above noted two base pair deletion, complete ATP synthetase subunit 8 and ATP synthetase subunit 6 genes, and a truncated CO3 gene of the published human mtDNA sequence of SEQ ID NO:2 (Anderson et al., *Nature* 290:456, 1981). The non-mitochondrial DNA sequences on either side of the 5,844 base pair exmtDNA sequence (nucleotides 1–480 and 6338–6744) did not display homology to any nuclear DNA sequences listed in the GenBank database.

Example 2

Detection of exmtDNA in RHO-0 Cells

In order to verify that presumptive exmtDNA sequences originated from nuclear and not mitochondrial DNA present in the DNA preparation from which the human genomic library was constructed, two established cell lines were depleted of mtDNA using ethidium bromide to generate ρα cells (Miller et al., *J. Neurochem.* 67:1897, 1996) and assayed for the presence of exmtDNA sequences. Briefly, ρ0118/5 and 064/5 SH-SY5Y neuroblastoma cells and 0A431 epidermal carcinoma cells were produced and maintained as described (Miller et al., 1996). Cells were harvested and DNA was extracted with DNAzol (Molecular Research Center, Inc., Cincinnati, Ohio) according to the manufacturer's instructions. The recovered DNA was amplified by PCR and analyzed by primer extension assay using primers specific for a sequence region containing the nucleotide at position 7146 of the mtDNA sequence (SEQ ID NO:2), which corresponds to a nucleotide substitution in the exmtDNA sequence. (Table 1 and SEQ ID NO:1) PCR primers and reaction conditions and primer extension assays were as described in Fahy et al. (*Nucl. Acids Res.* 25:3102, 1997), which is hereby incorporated by reference in its entirety. Primer extension products corresponding to a region of the exmtDNA sequence of SEQ ID NO:1 and including a nucleotide corresponding to the guanosine residue at position 7146 or its complement were detected in p0 cells that contained no detectable mtDNA as described herein and in Miller et al. (*J. Neurochem* 67:1897, 1996).

Example 3

Absence of Detectable Transcripts of exmtDNA Sequences in RT-PCR Assay

The reverse transcription-polymerase chain reaction (RT-PCR; Rappolee et al., *Science* 241:708, 1991; Chelly et al., Nature 333:858, 1988; Brenner et al., *BioTechniques* 7:1096, 1989) technique was employed to determine whether the novel 5.8 kb exmtDNA sequence cloned from a human genomic DNA library is transcribed. The buffy coat fraction of freshly drawn human venous blood was prepared using Accuspin devices (Sigma, St. Louis, Mo.) according to the manufacturer's instructions and total RNA was extracted from isolated buffy coat cells with Trizol reagent (GibcoBRL, Bethesda, Md.) as recommended by the supplier. First strand cDNA was synthesized from poly-A+ mRNA using the SuperScript™ preamplification system (GibcoBRL) with oligo(dT) as primer according to the manufacturer's instructions. PCR was conducted using this cDNA as template and primers complementary to portions of the CO2 mtDNA sequence (SEQ ID NO:2) as described in Fahy et al. (*Nucl. Ac. Res.* 25:3102, 1997). The corresponding region of exmtDNA (SEQ ID NO:1) contains nucleotide substitutions at positions 7650 and 7868, relative to mtDNA (Table 1). Amplicons were purified and analyzed by the primer extension assay as described in Fahy et al. such that readily distinguishable products are predicted depending on whether or not the primer has hybridized to a target sequence adjacent to a sequence having the substitutions. Based on quantitative analysis of fluorescent band intensities of the primer extension products, mRNA encoding human CO2 gene products of mtDNA (SEQ ID NO:2) was detectable, but no MRNA encoding products from the corresponding exmtDNA region of SEQ ID NO: 1 was detected, indicating that the exmtDNA sequence is not expressed.

Example 4

Primer Extension Assay to Quantify exmtDNA and mtDNA

A competitive primer extension approach was used to simultaneously detect both mtDNA and exmtDNA sequences with a fluorophor-labeled primer and a selected mix of deoxynucleotides (dNTPs) and dideoxynucleotides (ddNTPs). The exmtDNA and mtDNA compete as templates in the primer extension reaction and are distinguished by differential extension of the primer. Thus, to determine the relative quantities of defmed portions of mtDNA (SEQ ID NO:2) and exmtDNA (SEQ ID NO:1) using the nucleotide substitution at position 7650 (Table 1) with the nucleotide combination of dATP, dTTP and ddGTP, the primer is extended by one base when the template is mtDNA. When exmtDNA is present as template, the primer is extended by three bases. The proportion of numtDNA in relation to mtDNA is estimated by comparing the ratio of fluorescence intensities of the gel-separated extension products with a standard curve generated from known mtDNA/numtDNA mixtures. (Fahy et al., *Nucl. Ac. Res.* 25:3102, 1997)

Thermo Sequenase™, dNTPs and ddNTPs were purchased from Amersham (Cleveland, Ohio). Calf intestine alkaline phosphatase and biochemical reagents were obtained from Boehringer Mannheim (Indianapolis, Ind.) and QIAquick PCR purification kits from Qiagen (Chatsworth, Calif.). Accuspin™ Tubes and HISTO-PAQUE® 1077 were purchased from Sigma (St. Louis, Mo.) and EDTA vacutainers from Beckton Dickinson (San Jose, Calif.). UlTma™ DNA polymerase, AmpliTaq® DNA polymerase and reagents for DNA synthesis were purchased from Perkin Elmer (Foster City, Calif.). Oligonucleotides were synthesized on an Applied Biosystems 394 DNA/RNA synthesizer (Perkin Elmer) using standard phosphoramidite chemistry. 5' Fluorescein-labeled oligonucleotide primers were obtained by using the 6-FAM Amidite reagent in the last step of the automated synthesis. Tritylated and fluorescein-labeled oligonucleotides were purified by reverse phase chromatography using an acetonitrile gradient in 0.1 M triethylammonium acetate, pH 6.8 running buffer. The oligonucleotides migrated as single bands on a 15% denaturing polyacrylamide gel. The homogeneity of the fluorescein-labeled oligonucleotides was independently assessed by electrophoresis on an Applied Biosystems Model 373 Sequencing System.

After IRB approval and informed consent, fresh venous blood samples were drawn from 837 patients with clinical diagnosis of probable Alzheimer's disease (AD mean age= 74.7±1.1 years) and 191 controls (67±1 years; cognitively normal age-matched N=114; cortico-basal ganglionic degeneration N=2; Pick's disease N=1; Parkinson's disease N=24; non-insulin dependent diabetes mellitus N=29; insulin dependent diabetes mellitus N=6; Leigh's syndrome, N=2, Machado Joseph Disease N=2; idiopathic renal glycosuria N=1; progressive supranuclear palsy N=1; sporadic amyotropic lateral sclerosis N=6; familial sporadic amyotropic lateral sclerosis N=1; familial Alzheimer's disease N=2). AD patients met the National Institute of Neurological, Communicative Disorders and Stroke and Alzheimer's Diseases and Related Disorders Association (NINCDS-ADRDA) criteria of probable Alzheimer's disease (McKhann et al., *Neurology* 34:939, 1984).

Blood samples were collected in EDTA vacutainers and kept at 4° C. for no more than 24 h. The platelet/white blood cell fraction was isolated with Accuspin™ Tubes (Sigma Diagnostics, St. Louis, Mo.) using the following procedure. Three ml of HISTOPAQUE® 1077 (Sigma) were added to the upper chamber of each Accuspin™ Tube and the device was centrifuged at 1000 g for 30 s. Two to three ml of blood were then introduced into the upper chamber and separated by centrifugation at 1000 g for 10 min at room temperature. After centrifugation, the plasma and white blood cell layers were transferred to a new tube and the white blood cells were sedimented by centrifugation at 7,000 g for 10 min. The white cell pellet was resuspended in 0.4 ml of a solution containing 0.9% sodium chloride/1 mM EDTA and stored at −80° C. until use.

Frozen white blood cells (0.2 mL) were thawed and were sedimented by centrifugation at 12,000 g for 5 min. The white cell pellet was washed twice with 0.6 ml of Dulbecco's Phosphate Buffered Saline (PBS; GibcoBRL, Bethesda, Md.) and resuspended in 0.2 ml of water. The cells were lysed by incubation in a boiling water bath for 10 min. After cooling to room temperature, the cellular debris was sedimented by centrifugation at 14,000 g for 2 min. The supernatant was transferred to a new vial and the approximate concentration of the crude DNA preparation was estimated from its $A_{260}$ absorbance. The DNA sample was stored at −80° C.

Primer extension reaction templates were prepared by PCR amplification of cellular DNA. The reactions were carried out in a total volume of 50 μl using the primer pair sets described below. Following amplification, the PCR products were analyzed by electrophoresis on a 0.8% agarose gel. Reactions for analyzing exmtDNA to mtDNA ratios contained ~1 μg of cellular DNA, 2.5 U of AmpliTaq® DNA polymerase, 20 pmol each of the light strand primer 5'-CATGCAGCGCAAGTAGGTCTACAAGAC-3' (SEQ ID NO:6) and the heavy strand primer

5'-TGTTATGTAAAGGATGCGTAGGGATGG-3' (SEQ ID NO:7)

and 10 nmol of each dNTP in PCR buffer (10 mM Tris. HCl, pH 8.3, 50 mM KCl, 2 mM $MgCl_2$). After an initial denaturation step at 95° C. for 10 s in a Gene Amp PCR System 9600 thermal cycler (Perkin Elmer), amplification was carried out for 30 cycles under the following conditions: 95° C. for 1 min, 60° C. for 1 min, 72° C. for 1 min. After the last cycle, reaction tubes were kept at 72° C. for 4 min to ensure extension of incomplete strands to the full length 255 base pair size product.

Residual nucleotides that persisted after the PCR reaction were dephosphorylated by adding 1 unit of calf intestine alkaline phosphatase (CAP) in 5 µL of 10×CAP buffer (100 mM Tris. HCl, pH 8.3, 10 mM $MgCl_2$, 10 mM $ZnCl_2$) to the PCR reaction mixture and incubating for 30 min at 37° C. in thermal cycler. Then 1.1 µL of 0.25 M EDTA, pH 8.0 was added and the alkaline phosphatase was denatured at 75° C. for 10 min.

Double-stranded PCR products were separated from primers, nucleosides and enzymes using QIAquick™ columns (Qiagen, Chatsworth, Calif.) and the buffers provided by the manufacturer. Thus, 250 µl of buffer PB were added to the PCR reaction mixture and mixed. A Qiaquick™ spin column (Qiagen) was placed in a 2 ml collection tube and the sample was loaded. The sample was centrifuged for 30–60 s at 14000 g and the flow through was discarded. The adsorbed PCR product was washed with 750 µl of buffer PE, and eluted with 50 µl of 10 mM Tris. HCl, pH 8.5. The purified product solution was dried in a Savant SpeedVac Concentrator and then reconstituted in 20 µl of water.

The fluorescein-labeled primer for analysis of the AD-associated mutation at nucleotide position 7650 was
TATGAGGGCGTGATCATGAAAG (SEQ ID NO:8)
using dATP and dTTP plus dideoxyGTP (ddGTP) to generate primer extension products of 23 and 25 nucleotides in length from mtDNA and exmtDNA templates, respectively.

Stock solutions of each dNTP and ddNTP were prepared by mixing equimolar amounts of the nucleotides with $MgCl_2$ and diluting the mixture to the desired concentration with 10 mM Tris, 1 mM EDTA, pH 8.0 (TE). The fluorescein-labeled primers were diluted in TE to provide final stock concentrations of 40 fmol/µl. One µl of the purified PCR-amplified DNA fragment was used as template for each assay.

Primer extension reactions were performed in a total volume of 8 µL. The thermostable enzyme, UITma™ DNA polymerase (Perkin-Elmer, Foster City, Calif.) was used in primer extension assays for analyzing exmtDNA to mtDNA ratios. The reactions contained template, 20 fmol fluorescein-labeled primer, 400 µM ddNTPs/25 µM dNTPs of the appropriate nucleotide combination and 0.6 unit of enzyme in buffer containing 10 mM Tris-HCl, pH 8.8, 10 mM KCl, 0.002% Tween 20, 2 mM $MgCl_2$. Each set of primer extension assays included control reactions with mtDNA and exmtDNA templates.

The products of the primer extension reaction were analyzed on an ABI 373 Sequencer using a 12% denaturing polyacrylamide gel and Tris borate/EDTA as running buffer. Prior to electrophoresis, the samples in loading dye were denatured for 3 min at 85° C. Three µl aliquots of the standards (primer with no added template, reaction products from control DNA templates) and each unknown reaction mixture were then loaded and electrophoresed according the manufacturer's instructions. Fluorescent band intensities associated with the primer extension products were estimated by the GENESCAN™ 672 software program (Perkin Elmer, Applied Biosystems Division). Quantitative analysis was carried out by correlating the fluorescent band intensities of mtDNA and exmtDNA-derived extension products from unknown samples with those from mtDNA and exmtDNA control templates.

Example 5

Primer Extension Assay Using DNA Isolated from Affinity Isolated Mitochondria

Mitochondria were immunoaffinity isolated from cultured cells and then DNA was extracted from the isolated organelles, to determine whether detectable exmtDNA was present. Normal SH-SY5Y neuroblastoma cells, and normal and $\rho^0$ A431 epidermal carcinoma cells were produced and maintained as described (Miller et al., *J. Neurochem.* 67:1897, 1996). Cells were harvested by scraping in MSB (0.21 M mannitol, 0.07 M sucrose, 0.05 M Tris-HCl, 0.01 M EDTA, pH 7.4; $10^7$ cells/ml) and lysed by three freeze-thaw cycles. Cellular debris was removed by centrifugation at 1000×g for 5 min. The mitochondria enriched supernatants were used for subsequent immunopurification steps. The buffy coat fraction of whole blood containing white blood cells and platelets as described above was also prepared and lysed by freeze-thaw as was done with the cultured cells, to produce a mitochondrial fraction for immunopurification.

Monoclonal anti-mitochondrial antibody MAB 1273 (Chemicon International, Temecula, Calif.) was added to the mitochondria enriched fractions for 2 hr. Antibody-mitochondria complexes were isolated using a secondary antibody bound to magnetic beads (Dynal Inc., Great Neck, N.Y.) according to the manufacturer's instructions. After extensive washing of the bead-bound antibody-mitochondria complexes with PBS/0.1% BSA, mtDNA was extracted from the complexes using DNAzol reagent (Molecular Research Center, Inc., Cincinnati, Ohio) according to the manufacturer's recommendations. Quantification of mtDNA and exmtDNA was performed using the competitive primer extension assay described above in Example 4. No DNA could be amplified from the DNA extracted from immunopurified mitochondria from the $\rho^0$ A431 cell line, consistent with the depletion of mtDNA that is characteristic of the $\rho^0$ state. Primer extension results indicated that no exmtDNA sequences were present in the DNA extracted from mitochondria of blood buffy coat cells, SH-SY5Y cells or A431 cells, confirming that exmtDNA sequences are of extramitochondrial origin.

Example 6

Determination of ApoE Genotype by Primer Extension Assay

Primer extension assay procedures, essentially as described above in Example 4 but with the modifications indicated here, were used to determine APOE genotype in a panel of 837 clinically diagnosed AD individuals and 191 control subjects (cognitively normal age matched individuals, patients with non-insulin dependent diabetes mellitus (NIDDM) and neurological controls). The APOE allele distribution in the AD population an controls in the study is shown in Table 3.

TABLE 3

APOE Genotype Distribution

| APOE allele | Control (N = 191) | AD (N = 837) |
|---|---|---|
| 2/2 | 1 | |
| 2/3 | 16 | 33 |
| 2/4 | 3 | 22 |
| 3/3 | 112 | 295 |
| 3/4 | 56 | 403 |
| 4/4 | 3 | 84 |

DNA isolation and preparation of primer extension reaction templates by PCR were essentially as described above in Example 4, except that for APOE analysis, a modification of the protocol of Livak and Hainer (1994) was used. Thus, for template preparation by PCR each reaction contained ~1 μg of cellular DNA, 2.5 U of AmpliTaq® DNA polymerase, 20 pmol each of the forward primer 5'-GGCACGGCTGTCCAAGG-3' (SEQ ID NO:9) and
the reverse primer
5'-CCCGGCCTGGTACACTG-3' (SEQ ID NO:10)

and 10 nmol of each dNTP in PCR buffer (10 mM Tris. HCl, pH 8.3, 50 mM KCl, 1.5 mM $MgCl_2$ supplemented with 5% DMSO). After an initial denaturation step at 95° C. for 10 s in a Gene Amp PCR System 9600 thermal cycler (Perkin Elmer), amplification was carried out for 25 cycles under the following conditions: 95° C. for 1 min, 55° C. for 1 min, 72° C. for 1 min. The PCR product obtained after amplification was 226 base pairs in length.

The fluorescein-labeled primers and nucleotide combinations for primer extension analysis of Apo-E alleles are shown in Table 4.

TABLE 4

| Gene | Primer Sequence (5'→3') | Primer size | Extension Product sizes | dNTP | ddNTP |
|---|---|---|---|---|---|
| APOE Codon 112 | GCGGACATGGAGGACGTG (SEQ ID NO:11) | 18 | 19, 20 | T | G, C |
| APOE Codon 158 | CGATGCCGATGACCTGCAGAAG (SEQ ID NO:12) | 22 | 23, 24 | T | G, C |

Thermo Sequenase™ (Amersham, Cleveland, Ohio) DNA polymerase catalyzed reactions for Apo-E allele analysis were performed with 20 fmol fluorescein-labeled primer, 25 μM each of the appropriate ddNTP/dNTP combination and 0.64 unit of enzyme in buffer containing 10 mM Tris-HCl, pH 9.5, 5 mM KCl, 0.002% Tween 20, 2 mM $MgCl_2$. Each set of primer extension assays included Apo-E allelic DNA controls. After an initial denaturation step at 95° C. for 2 min, the reaction conditions comprised 20 cycles of 95° C. for 20 s and 55° C. for 40 s. The samples were concentrated to ~1 μl by heating open reaction tubes at 94° C. for 7 min. After the concentration step, 8 μl of loading dye (0.5% blue dextran in 83% formamide/8.3 mM EDTA, pH 8.0) was added.

The products of the primer extension reaction were analyzed as described above in Example 4. The Apo-E allele composition of unknown DNA samples was deduced by comparing the electrophoretic pattern of primer extension products with those from Apo-E allele DNA standards. APOE genotype distribution is shown in Table 3.

Example 7

Correlation of exmtDNA:mtDNA Ratio with Risk for AD

Primer extension assays as described in Example 4 were used to quantify the amounts of mtDNA and exmtDNA in blood samples from a panel of 837 clinically diagnosed AD individuals and 191 control subjects (cognitively normal age matched individuals, patients with non-insulin dependent diabetes mellitus (NIDDM) and neurological controls). For each subject, a ratio r was calculated using the formula:

$$r=x/(x+y)$$

wherein x is the amount of exmtDNA in a sample, and y is the amount of mtDNA in the sample.

The values for r were multiplied by 100 to give ranges of values according to which the patient population was stratified as shown in Table 5. Within each stratified range, the ratio of the number of subjects diagnosed with AD (McKhann et al., *Neurology* 34:939, 1984) to the number of subjects not having AD was determined, showing a correlation of increasing r value with increasing risk for AD (Table 5).

TABLE 5

Relative Risk for AD:by r Value

| r × 100 | # of AD subjects:# of Non-AD subjects |
|---|---|
| >15 | 1.42 |
| >20 | 1.8 |
| >25 | 2.2 |
| >30 | 2.0 |

Example 8

Increased Predictive Value of exmtDNA:mtDNA Ratio in Subjects Having at Least One APoE4 Allele Determination of the value r according to Example 7 was combined with determination of APOE genotype according to Example 6 using the patient populations characterized in Examples 6 and 7 to ascertain the relationship of APOE genotype to relative risk for AD, and to demonstrate the increased correlative value of APOE genotype combined with increasing r values with relative risk for AD. The relative risk for AD as a function of APOE genotype using the APOE alleles 2, 3 or 4 alone is shown in the bottom line of Table 6. The remainder of Table 6 shows the relative risk of AD as a function of APOE genotype and r value when subjects are stratified according to r as in Example 7. The relative risk for AD increases as a function of increasing r. In particular individuals with one APOE4 allele, and especially subjects who are homozygous for the APOE4 allele, exhibit increasing risk for AD as a function of increasing r, as shown in Table 6.

TABLE 6

Relative Risk for AD:by r value and ApoE Genotype
(# AD:# Non-AD) ApoE Genotype

| r × 100 | e2/3 | e3/3 | one e4 allele | e3/4 | e4/4 |
|---|---|---|---|---|---|
| >15 | 1.5 | 1.5 | 2.2 | 2.1 | 7.1 |
| >20 | 2.0 | 1.9 | 3.7 | 3.1 | 9.0 |
| >25 | 1.7 | 1.8 | 5.3 | 3.0 | >9.0 |
| >30 | 2.5 | 2.0 | 4.6 | 3.0 | >9.0 |
| independent of r | 0.5 | 0.6 | 1.9 | 1.7 | 6.3 |

Example 9

Identification of Agents that Alter VAlue of R

In this example, an agent suitable for treating AD is identified based on its ability to lower the value of r as defined above. A blood sample is obtained from a patient diagnosed with AD (McKhann et al., *Neurology* 34:939, 1984) and a ratio r is calculated using the formula:

$$r = x/(x+y)$$

wherein x is the amount of exmtDNA in a sample, and y is the amount of mtDNA in the sample, where x and y are determined using the primer extension assay as described in Example 4. The candidate agent is then administered to the patient in a quantity and for a time sufficient to impart a therapeutically beneficial effect, and blood samples are periodically collected and processed using the primer extension assay as described in Example 4 to monitor alterations in the value r. Candidate agents are subjected to preliminary characterization for toxicity, bioavailability and modes of delivery prior to administration to a patient. An agent is selected that causes a reduction in the value for r, signifying an effect on the altered mitochondrial function in the patient that may underlie the differential extractability of exmtDNA and mtDNA that contributes to r values associated with increased risk for AD.

Example 10

Detection of exmtDNA Sequences in Telomeres

In this example, fluorescence in situ hybridization (FISH) is used to localize nucleic acid sequences that are present in SEQ ID NO:1 to the telomeric region of at least one human chromosome. The methods of Cannizzaro et al. (Methods Mol. Biol. 75:313, 1997) and references cited therein, all of which are incorporated hereby in their entireties, are used to conduct FISH. Human cell lines are grown to confluence on coverslips and then fixed and permeabilized for FISH analysis of metaphase chromosomes. The cloned pBeloBAC insert containing SEQ ID NO:1 as described above is excised from the plasmid vector and fluorescein labeled as described, and used to probe the fixed and permeabilized cells. Metaphase cells are evaluated by fluorescent laser scanning confocal microscopy and subchromosomal localization of the fluorescent probe to telomeric regions is observed. Cytological methods are used to prepare metaphase spreads of human peripheral blood leukocytes as described in the cited references, and the chromosomes are doubly labeled using suitable reporter moieties for discerning two signals, one being quinacrine to identify each chromosome by its characteristic banding pattern and the other being the labeled SEQ ID NO:1 insert, to correlate a particular chromosome with telomeric hybridization of the insert. The nucleic acid insert of SEQ ID NO:1 is next fragmented with restriction endonucleases, and the separated fragments are labeled to generate a panel of probes representing distinct sequence portions of SEQ ID NO:1, to determine whether the portion of the insert hybridizing to telomeres corresponds to an exmtDNA sequence or a non-exmtDNA sequence present in the insert as it was cloned from the human genomic library, as described above in Example 1.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for determining the risk for or presence of a disease associated with altered mitochondrial function in a first subject suspected of having or being at risk for having such a disease, comprising:

quantifying, in each of a first and a second biological sample containing extramitochondrial DNA and mitochondrial DNA, (i) an amount y of a mitochondrial DNA sequence, and (ii) an amount x of an extramitochondrial DNA sequence that corresponds to the mitochondrial DNA sequence, said first biological sample being obtained from a first subject suspected of having or being at risk for having a disease associated with altered mitochondrial function and said second sample being obtained from a second subject known to be free of a risk or presence of a disease associated with altered mitochondrial function; and comparing a ratio r for each of the first and second biological samples using the formula:

$$r = x/(x+y)$$

and therefrom determining the risk or presence of the disease.

2. The method of claim 1 wherein the ratio r is calculated by a method comprising:

contacting a biological sample containing extramitochondrial DNA and mitochondrial DNA with an oligonucleotide primer having a nucleotide sequence that is complementary to a sequence present in said extramitochondrial DNA and present in said mitochondrial DNA, under conditions and for a time sufficient to allow hybridization of said primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA.

3. The method of claim 1 wherein the ratio r is calculated by a method comprising:

contacting a sample containing amplified extramitochondrial DNA and mitochondrial DNA with an oligonucleotide primer having a nucleotide sequence that is complementary to a sequence present in said amplified extramitochondrial DNA and present in said amplified mitochondrial DNA, under conditions and for a time sufficient to allow hybridization of said primer to the extramitochondrial DNA and to the mitochondrial DNA; and detecting hybridization of the primer to the extramitochondrial DNA and to the mitochondrial DNA, and therefrom quantifying the extramitochondrial DNA and the mitochondrial DNA.

4. The method of claim 1 wherein the ratio r is calculated by a method comprising:

contacting a biological sample containing extramitochondrial DNA and mitochondrial DNA with an oligonucleotide primer having a nucleotide sequence that is complementary to a sequence present in said extramitochondrial DNA and present in said mitochondrial DNA, under conditions and for a time sufficient to allow hybridization of said primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from said first product, and therefrom quantifying the extramitochondrial DNA and the mitochondrial DNA.

5. The method of claim 1 wherein the ratio r is calculated by a method comprising:

contacting a sample containing amplified extramitochondrial DNA and mitochondrial DNA with an oligonucleotide primer having a nucleotide sequence that is complementary to a sequence present in said amplified extramitochondrial DNA and present in said amplified mitochondrial DNA, under conditions and for a time sufficient to allow hybridization of said primer to the extramitochondrial DNA and to the mitochondrial DNA; and detecting hybridization and extension of the primer to the extramitochondrial DNA to produce a first product and hybridization and extension of the primer to the mitochondrial DNA to produce a second product distinguishable from said first product, and therefrom quantifying the extramitochondrial DNA and the mitochondrial DNA.

6. The method of claim 1 wherein the biological sample is treated by heating said sample in water to lyse cells contained in the sample, and then extracting cellular DNA from said lysed cells using an aqueous DNA extraction procedure.

7. The method of claim 6 wherein the sample comprises a crude buffy coat fraction of whole blood.

8. The method of claim 1, further comprising the step of determining the ApoE genotype of the first subject and correlating said genotype with the risk or presence of disease.

9. The method of claim 1 wherein the disease associated with altered mitochondrial function is selected from the group consisting of Alzheimer's Disease, Huntington's Disease, Parkinson's Disease, dystonia, schizophrenia, non-insulin dependent diabetes mellitus, mitochondrial encephalopathy, lactic acidosis, and stroke, myoclonic epilepsy ragged red fiber syndrome, and Leber's hereditary optic neuropathy.

10. The method of claim 1 wherein the ratio r for the biological sample is calculated by determining the presence in said sample of a nucleotide sequence selected from the group consisting of SEQ ID NO:1, a portion of SEQ ID NO:1, SEQ ID NO:3 and a portion of SEQ ID NO:3.

11. The method of claim 10 wherein the portion of the nucleotide sequence of SEQ ID NO:1 corresponds to a portion of the nucleotide sequence of SEQ ID NO:2 encoding a mitochondrial cytochrome c oxidase.

12. The method of claim 10 wherein the portion of SEQ ID NO:1 corresponds to a portion of a mitochondrial cytochrome c oxidase encoding sequence selected from the group consisting of a portion of a CO1 encoding sequence and a portion of a CO2 encoding sequence.

13. The method of claim 10 wherein the portion of the nucleotide sequence of SEQ ID NO:1 corresponds to a portion of the nucleotide sequence of SEQ ID NO:2 encoding a mitochondrial ATP synthetase subunit.

14. The method of claim 10 wherein the portion of SEQ ID NO:1 corresponds to a portion of a mitochondrial ATP synthetase subunit encoding sequence selected from the group consisting of a portion of a sequence encoding ATP synthetase subunit 6 and a portion of a sequence encoding ATP synthetase subunit 8.

15. The method of claim 10 wherein the nucleotide sequence of SEQ ID NO:1 corresponds to a portion of SEQ ID NO:2 selected from the group consisting of a portion of a sequence encoding ND1, a sequence encoding a portion of ND2 and a sequence encoding a portion of CO3.

16. The method of claim 10 wherein the portion of the nucleotide sequence of SEQ ID NO:3 corresponds to a portion of the nucleotide sequence of SEQ ID NO:2 encoding a mitochondrial ATP synthetase subunit.

17. The method of claim 10 wherein the portion of SEQ ID NO:3 corresponds to a portion of a mitochondrial ATP synthetase subunit encoding sequence selected from the group consisting of a portion of a sequence encoding ATP synthetase subunit 6 and a portion of a sequence encoding ATP synthetase subunit 8.

18. The method of claim 10 wherein the portion of the nucleotide sequence of SEQ ID NO:1 corresponds to a portion of the nucleotide sequence of SEQ ID NO:2 encoding a mitochondrial tRNA.

19. The method of claim 10 wherein the portion of the nucleotide sequence of SEQ ID NO:3 corresponds to a portion of the nucleotide sequence of SEQ ID NO:2 encoding a mitochondrial tRNA.

20. A method for determining the risk or presence of a disease associated with altered mitochondrial function in a first subject suspected of having or being at risk for having such a disease, comprising:

quantifying, in a first biological sample containing extramitochondrial DNA and mitochondrial DNA, wherein at least one of said extramitochondrial DNA and said mitochondrial DNA is from a first subject suspected of having or being at risk for having a disease associated with altered mitochondrial function, (i) an amount of a first mitochondrial DNA sequence and (ii) an amount of a first extramitochondrial DNA sequence that corresponds to the first mitochondrial DNA sequence; and comparing said amounts of the first mitochondrial DNA sequence and the first extramitochondrial DNA sequence that corresponds to the first mitochondrial DNA sequence to amounts, in a second biological sample from a second subject known to be free of a risk or presence of a disease associated with altered mitochondrial function, of a second mitochondrial DNA sequence and a second extramitochondrial DNA sequence that corresponds to the second mitochondrial DNA sequence, and therefrom determining the risk or presence of the disease.

* * * * *